US009681813B2

(12) United States Patent
Chenaux et al.

(10) Patent No.: US 9,681,813 B2
(45) Date of Patent: Jun. 20, 2017

(54) NEUROPHYSIOLOGICAL STIMULATION SYSTEM AND METHODS WITH WIRELESS COMMUNICATION

(75) Inventors: Fabrice Chenaux, Montmollin (CH); Jean-Sebastien Merette, Mont-St-Hillaire (CA)

(73) Assignee: DINNOS TECHNOLOGY, Avondale, PA (US)

( * ) Notice: Subject to any disclaimer, the term of this patent is extended or adjusted under 35 U.S.C. 154(b) by 1331 days.

(21) Appl. No.: 13/461,291

(22) Filed: May 1, 2012

(65) Prior Publication Data

US 2012/0259239 A1   Oct. 11, 2012

Related U.S. Application Data

(63) Continuation-in-part of application No. 12/845,784, filed on Jul. 29, 2010, now abandoned.

(Continued)

(51) Int. Cl.
*H01B 7/00* (2006.01)
*A61B 5/04* (2006.01)
(Continued)

(52) U.S. Cl.
CPC .......... *A61B 5/04001* (2013.01); *A61B 5/411* (2013.01); *A61B 5/4893* (2013.01); *A61B 5/6806* (2013.01); *A61B 5/0488* (2013.01)

(58) Field of Classification Search
CPC .......... H01R 4/00; H01R 9/00; H01R 9/0509; H01R 11/11; H01R 4/023; H01R 4/22; H02G 15/08; H02G 11/00; H02G 11/006; H02G 3/04; H02G 15/02; H02G 15/24; H02G 15/043; H02G 3/06; B60R 16/0207; B60R 16/0215; H01B 7/0045; H01B 7/06; H01B 11/00; H01B 12/00; H01B 5/00; H01B 9/00; H01B 11/18; H01B 9/04; H01B 11/06; H01B 11/002; H01B 11/005; H01B 11/08; H01B 11/085; H01B 11/10; H01B 11/008; H01B 11/1016; H01B 11/1025; H01B 11/1033; H01B 11/1041; H01B 11/105; H01B 11/1058; H01B 11/1075; H01B 11/1083; H01B 11/1091;
(Continued)

(56) References Cited

U.S. PATENT DOCUMENTS 3,435,401 A * 3/1969 Epstein ................... F24D 13/02
174/110 PM
3,845,771 A    11/1974 Vise
(Continued)

*Primary Examiner* — Pete Lee
(74) *Attorney, Agent, or Firm* — Roach Brown McCarthy & Gruber, P.C.; Kevin D. McCarthy

(57) ABSTRACT

The present invention provides methods and apparatus that allow the surgeon and the IONM specialist to continuously get a feedback on the relative proximity from the instruments to a nerve and on the health of this nerve. By having a coupling device that allows every instrument to be electrically stimulated, the surgeon, through the instruments, continuously sends a small electrical input into the patient's body and depending on the relative proximity between this electrical stimulation and a nerve, a neuromonitoring modality is recorded through electrodes placed on the patient. The characteristics of this response allow the IONM specialist to determine the health status and or location of the nerves.

21 Claims, 40 Drawing Sheets

Related U.S. Application Data

(60) Provisional application No. 61/273,017, filed on Jul. 29, 2009, provisional application No. 61/276,997, filed on Sep. 18, 2009.

(51) Int. Cl.
*A61B 5/00* (2006.01)
*A61B 5/0488* (2006.01)

(58) Field of Classification Search
CPC ...... H01B 11/1834; H01B 7/08; H01B 3/085; H01B 3/008; H01B 3/0381; H01B 3/082; H01B 3/084; H01B 7/0807; H01B 7/0823; H01B 7/083; H01B 7/0838; H01B 7/0846; H01B 7/0853; H01B 7/0861; H01B 7/0869; H01B 7/0876; H01B 7/0884; H01B 7/181; H01B 7/1815; H01B 7/182; H01B 7/1825; H01B 7/188; H01B 7/1885; H01B 17/325; H01B 3/47; H01B 3/48; H01B 3/485; H01B 3/50; H01B 3/52; H01B 3/54; H01B 3/545; H01B 7/02; H01B 3/28; H01B 5/16; H01B 12/02; H01B 12/04; H01B 12/06; H01B 12/08; H01B 12/10; H01B 12/12; H01B 12/14; H01B 12/16; H01B 1/00; G02B 6/02; G02B 6/44; H05K 1/118; H05K 2201/05; H05K 3/4046; A61B 5/04001; A61B 5/0488; A61B 5/411; A61B 5/6806; A61B 5/4893
USPC ........................................................ 174/72 A
See application file for complete search history.

(56) References Cited

U.S. PATENT DOCUMENTS

| | | |
|---|---|---|
| 4,144,877 A | 3/1979 | Frei |
| 4,198,985 A | 4/1980 | Abel |
| 4,207,904 A | 6/1980 | Greene |
| 4,250,894 A | 2/1981 | Frei |
| 4,337,496 A | 6/1982 | Laird |
| 4,370,696 A | 1/1983 | Darrell |
| 4,485,426 A | 11/1984 | Kerls |
| 4,488,726 A | 12/1984 | Murray |
| 4,510,939 A | 4/1985 | Brenman |
| 4,542,753 A | 9/1985 | Brenman |
| 4,609,845 A * | 9/1986 | Soni ...................... H01L 41/087 29/25.35 |
| 4,620,528 A | 11/1986 | Arraval |
| 4,765,343 A | 8/1988 | Brenman |
| 5,067,478 A | 11/1991 | Berlant |
| 5,070,862 A | 12/1991 | Berlant |
| 5,242,440 A | 9/1993 | Shippert |
| 5,283,722 A | 2/1994 | Koenen |
| 5,345,612 A | 9/1994 | Stein |
| 5,648,003 A | 7/1997 | Liang |
| 5,673,436 A | 10/1997 | Piper |
| 5,782,516 A | 7/1998 | Partida |
| 5,816,676 A | 10/1998 | Koenen |
| 5,947,922 A | 9/1999 | Macleod |
| 6,112,330 A | 9/2000 | Bryan |
| 6,120,501 A | 9/2000 | Long |
| 6,141,643 A | 10/2000 | Harmon |
| 6,235,027 B1 | 5/2001 | Herzon |
| 6,409,734 B1 | 6/2002 | Zapata |
| 6,466,817 B1 | 10/2002 | Kaula |
| 6,551,312 B2 | 4/2003 | Zhang |
| 6,567,990 B1 | 5/2003 | Spitznagle |
| 6,569,163 B2 | 5/2003 | Hata |
| 6,584,359 B1 | 6/2003 | Motoi |
| 6,592,235 B1 | 7/2003 | Mayo |
| 6,646,855 B2 | 11/2003 | Buening |
| 6,850,162 B2 | 2/2005 | Cacioli |
| 6,892,397 B2 | 5/2005 | Raz |
| 6,904,614 B2 | 6/2005 | Yamazaki |
| 7,012,797 B1 | 3/2006 | Delida |
| 7,128,741 B1 | 10/2006 | Isaacson |
| 7,207,949 B2 | 4/2007 | Miles |
| 7,470,236 B1 | 12/2008 | Kelleher |
| 2004/0154071 A1 | 8/2004 | Frahm |
| 2004/0260281 A1 | 12/2004 | Baxter |
| 2007/0118965 A1 | 5/2007 | Hoffman |
| 2007/0174947 A1 | 8/2007 | Schneider |
| 2009/0204176 A1 | 8/2009 | Miles |
| 2010/0010367 A1 | 1/2010 | Foley |
| 2010/0076144 A1* | 3/2010 | Moore .................... C08L 23/16 524/502 |
| 2011/0088945 A1* | 4/2011 | Yanagimoto ............ H05K 1/028 174/72 A |
| 2011/0301677 A1* | 12/2011 | Hendricks ................ A61N 1/05 607/116 |

\* cited by examiner

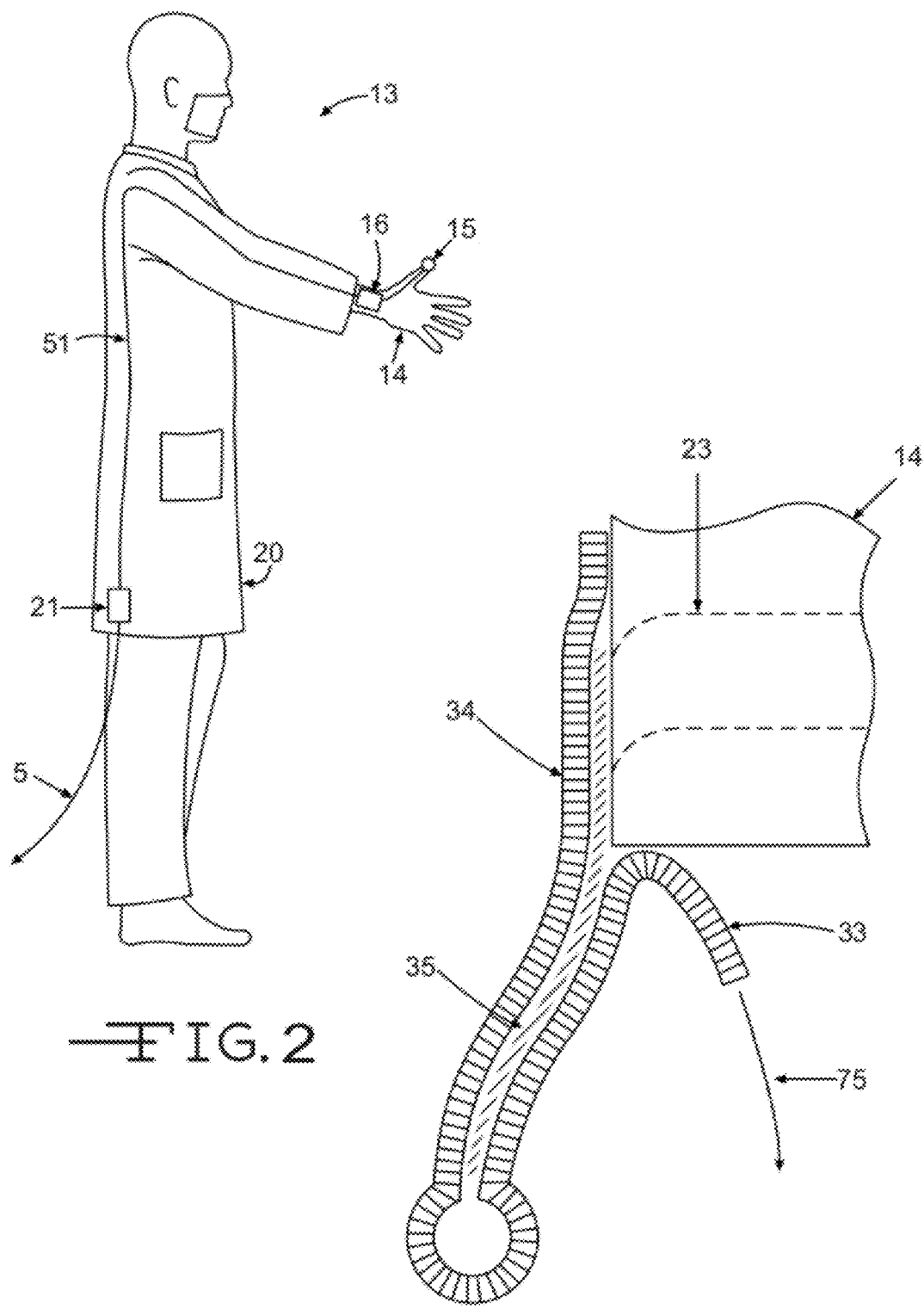

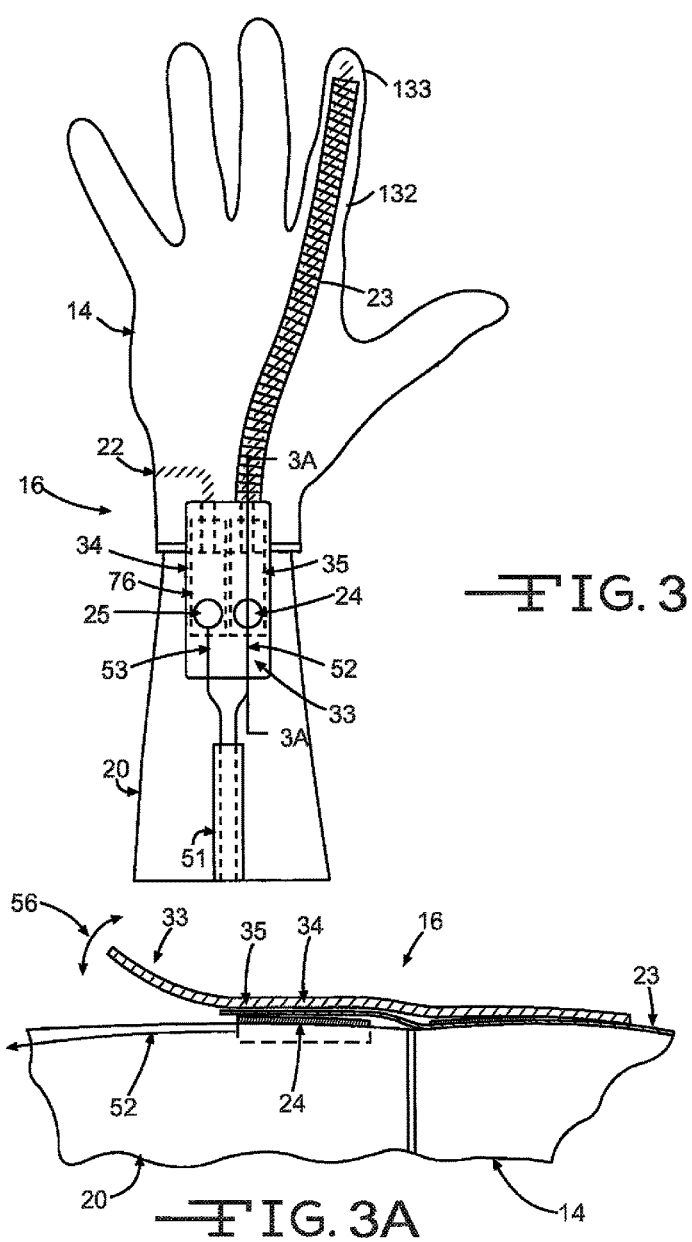

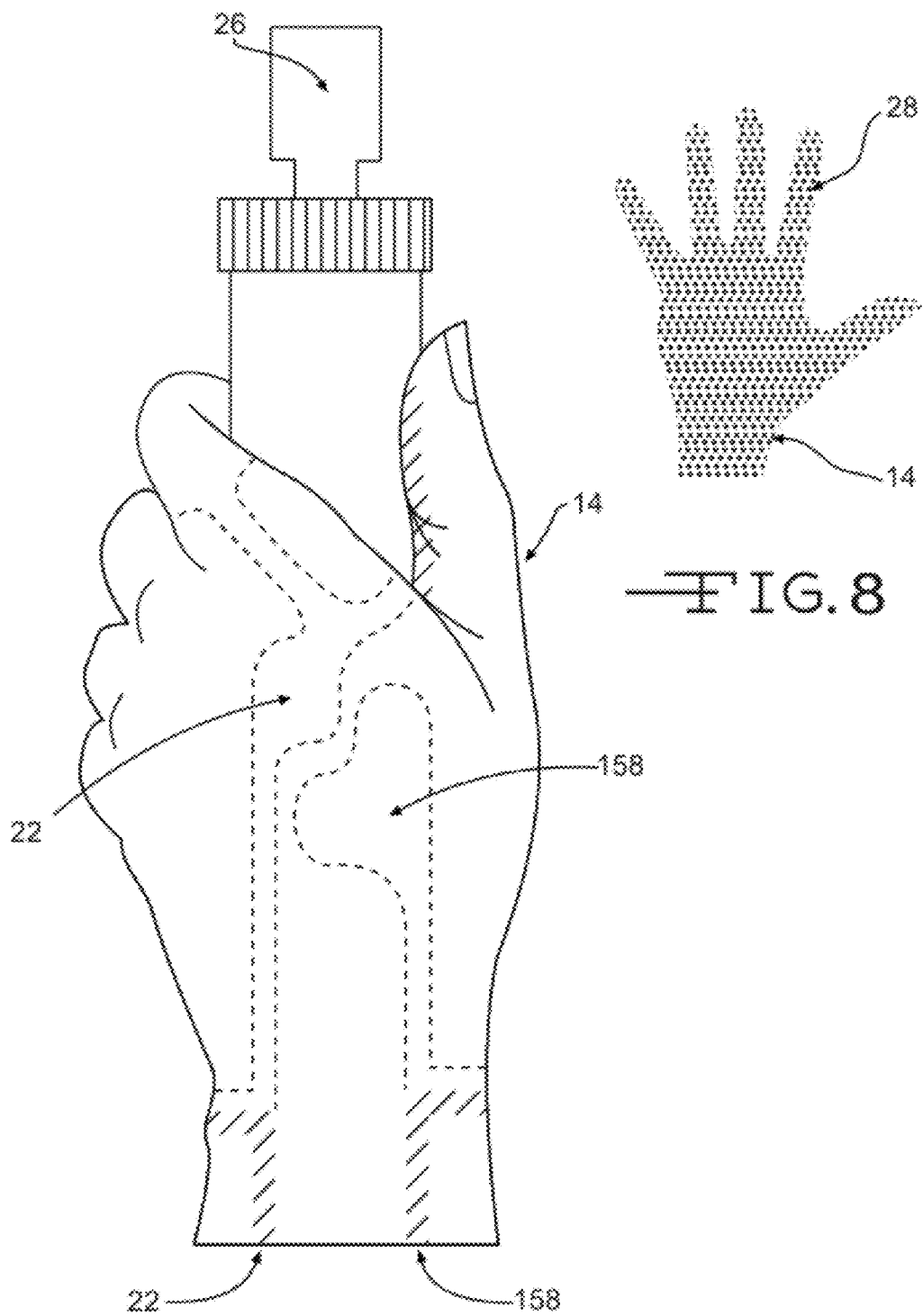

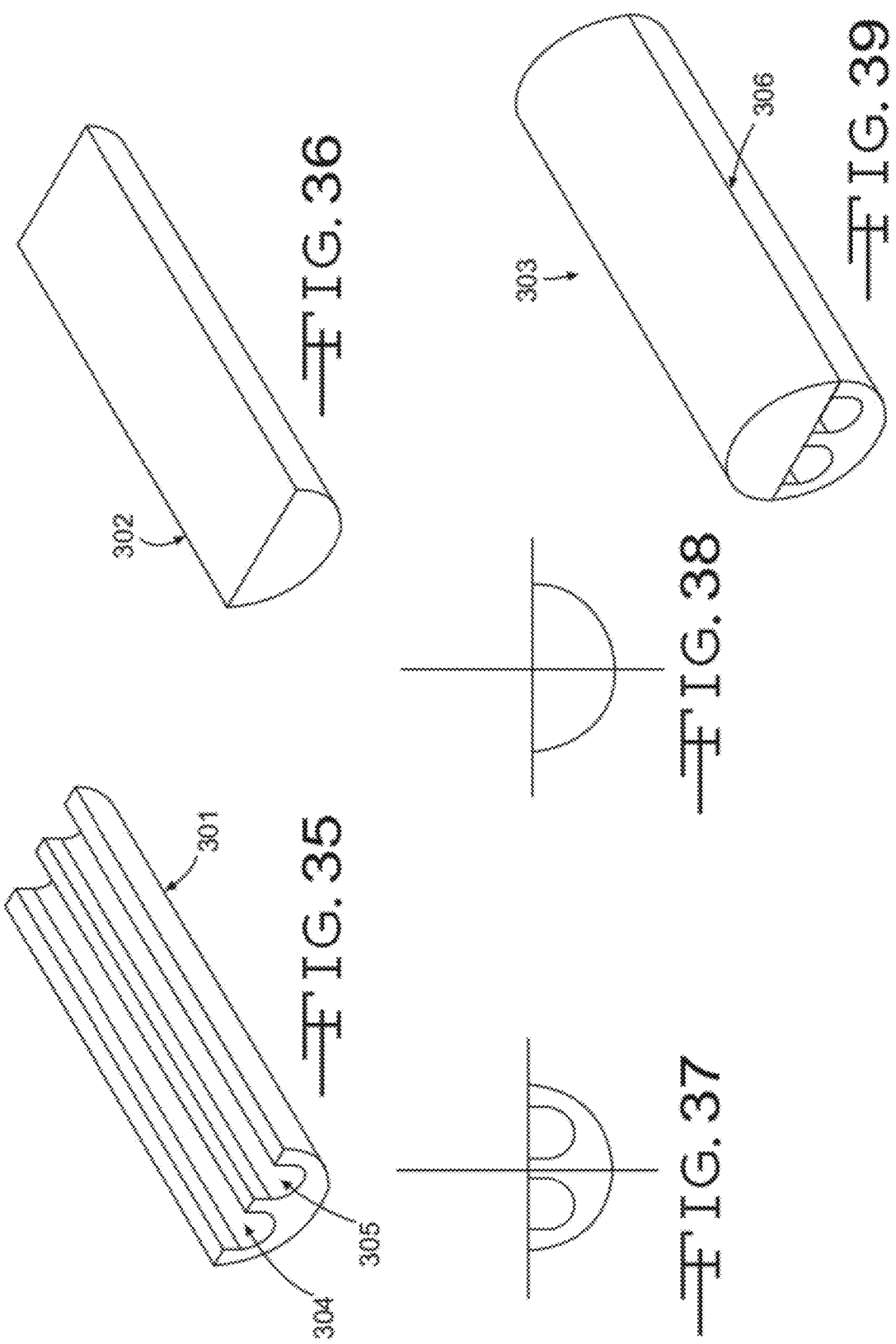

NEUROPHYSIOLOGICAL STIMULATION SYSTEM AND METHODS WITH WIRELESS COMMUNICATION

CROSS-REFERENCES TO RELATED APPLICATIONS

This application claims priority as a provisional application to U.S. patent application Ser. No. 12/845,784, filed on Jul. 29, 2010; which claims priority as a nonprovisional application of (a) U.S. provisional patent application number: U.S. 61/273,017 filed on Jul. 29, 2009; and (b) U.S. provisional patent application number: U.S. 61/276,997 filed on Sep. 18, 2009.

FIELD OF THE INVENTION

The present invention relates to a neuromonitoring system and surgical instrumentation combined with an improved technique for applying electrical stimuli on nerves or living tissues during a surgical intervention for the purpose of monitoring the status and location of nerves during surgery.

BACKGROUND OF THE INVENTION

Nerve injury is a major risk during a surgery. Minimally invasive surgical procedures with small incisions limit direct visualization of the targeted site and therefore reinforce the need of improved techniques for neurostimulation and neuromonitoring.

Intra-operative neuromonitoring (IONM) has been performed for a long time by the neurophysiologist practitioners and well known techniques like motor evoked potentials (MEP), transcranial motor evoked potentials (TcMEP), train of four (TOF), somatosensory evoked potentials (SSEP) and free-run electromyography (EMG) have been proven. These techniques help the IONM specialist to assess the nervous system of the patient during the surgery and more particularly give information on the health of targeted nerves in the proximity of the surgical site. However, these techniques have limitations and don't offer an immediate feedback on potential nerve damage that may occurred during specific actions performed by the surgeon. Usually, electrified probes are used by the surgeon to send stimulation current into the patient's tissues. The stimulation current flows through the tissues to a reference electrode placed in the near proximity of the surgical site. The amplitude of the current sent is set sufficiently high in order to reach and depolarize the nerves running into the stimulated tissues and potentials will be evoked in the related muscles. EMG signals or mechanical movements will be recorded on the neuromonitoring system via electrodes placed on or in the patient's muscles. In a typical method of nerve locating, the stimulation current is then lower and more probing is done towards the identified nerve until evoked potentials in the muscles are recorded again. This loop may be repeated several times until the stimulation current is down to an amplitude where the nerve depolarizes only when the probe is in contact with it. Since the IONM specialist doesn't have direct access and visualization of the surgical site, it's difficult for him to trigger and set the appropriate nerve stimuli in order to monitor the right parameter.

Surgical gloves are personal protection equipment designed to provide comfort and tactile sensitivity while protecting clinicians and patients during operating procedures in an operating room environment. The primary purpose of surgical gloves is to act as a protective barrier for surgeons and nurses to prevent possible transmission of diseases or pathogens during procedures while working with surgical instruments. Similar to medical examination glove, surgical glove standards are governed by the Food and Drug Administration (FDA) within the United States and other regulated entities around the world. Mechanical and biocompatible properties must follow the minimal requirements published in the applicable standards. Since the majority of surgical gloves are still made from natural rubber, latex allergy awareness has open ways for additional materials to be introduced in the manufacturing of surgical gloves. Many latex-free materials like polychloroprene, nitrile, vinyl or polyisoprene (synthetic rubber) are available. All surgical gloves are sterilized and package sealed in pairs for single use. The sterilization of surgical gloves is standard as surgical procedures often involve open wound operation. In contrast to medical exam gloves, surgical gloves are form fitted meaning every pair contains one glove shaped for the left hand and one glove shaped for the right hand. This is to ensure the highest level of comfort, tactile feeling and to help reduce fatigue from long surgical procedures. In contrast to medical examination gloves, surgical glove are sized in order to provide a better fitting glove which will be available for every surgeon.

In the U.S. Pat. No. 4,510,939; Brenman et al. describe the invention of a means for applying electrical stimuli to living tissue. This method uses a surgical glove on which electrodes and electrical conductors are mounted on the external surface of the glove with adhesive materials. At least one stimuli electrode and a second reference electrode are placed on the finger of the glove. This invention is only suitable for stimulating by palpation some localized internal cavities of the body but cannot be used for intra-operative neurostimulation since the electrical current flows from the stimuli electrode on the glove to the reference electrode on the glove. This keeps the electrical path local to the finger and would only depolarize a nerve if touching it with the glove or in near proximity. Despite the fact that the stimuli electrode and the reference electrode are too close to each other, Brenman's glove would need to be connected to a neuromonitoring system that can record electrical responses of the muscles and where stimulation currents can be adjusted in relation to those responses in order to perform nerve health assessment and nerve localization. Further, Brenman's invention would not be suitable for surgical glove since the adhesive material used for affixing the electrodes and electrical conductors would affect the mechanical strength and elongation properties of the glove in such a way that it would not pass the required standards for surgical gloves. Moreover, during many surgeries, areas that need to be stimulated are not accessible by palpation with fingers.

In the U.S. Pat. No. 3,845,771 from Vise and in the U.S. Pat. No. 6,551,312 from Zhang et al.; both Vise and Zhang described a method of transmitting electrical energy to wireless instruments through surgical gloves having electrical conductors. These inventions are limited to transmitting electrical energy to electrosurgical devices as electrocautery or electro-coagulation devices. Electrocautery or electro-coagulation requires currents in a range of 500 to 700 mA in order to produce localized heat when the current is concentrated in a small surface of contact. Therefore, Vise and Zhang's gloves require larger and thicker electrical contact pads in order to transmit the high currents needed to the instrument without producing heat. Having larger and thick pads on the glove is not suitable for surgical gloves where the surgeon needs to have high tactile feeling through the glove. Electrocautery or electro-coagulation usually operates at frequencies between 100 KHz and 5 MHz in order to minimize effects of muscle contraction or nerve stimulation. It is well known that it is impossible to perform neuromonitoring during electrosurgery due to the fact that electrosurgery uses high frequencies, including radiofrequencies, and high voltages to cut through and coagulate tissues, and this causes important noise perturbation of the neuromonitoring signals. Further, Vise and Zhang need to control the activation of the electrosurgical source of current by the use of a mechanical switch either on the instrument or in between the electrosurgical source and the glove in order to switch off the electrical current that flows through the electrical conductors of the glove and avoid important risks of electrocution or injury to the patient if the surgeon inadvertently touches the body of the patient. This is opposite to the present invention where the main advantage is to always send electrical stimulations through instruments without having to manually activate it.

The Spitznagle discloses, in the U.S. Pat. No. 6,567,990, electromyography (EMG) electrodes mounted on the examination gloves and used for measuring the electrical currents generated by muscles contraction. The glove of this invention is only used for sensing EMG signals which resolve from muscle movements and not to stimulate the muscle. Further, similar to the '939 glove of Brenman, there are two electrodes on the finger, one being active and the other being indifferent or the ground reference.

In the U.S. Pat. No. 7,207,949 of Miles et al., U.S. Pat. No. 6,466,817 of Kaula et al., U.S. Pat. No. 7,470,236 of Kelleher et al., these inventors disclosed a surgical access system equipped with electrodes to send stimulation currents through the instruments into the patient's body and a standalone neuromonitoring system for detecting and mapping the nervous system. This system's instruments are all connected to the stimulator through a wired electrical connector. It has been observed that the surgical team either inadvertently forgets to connect the electrical connector to the instrument being used or the surgeon switches between instruments rapidly and there is no time to interrupt the surgical procedure. As a result, no electrical stimulation is sent through the instruments and therefore, it is difficult if not impossible to monitor the nerve location.

In the U.S. Pat. No. 5,067,478, Berlant disclose a structure and method of manufacturing an electrode glove for applying electro-massage. This method requires the use of two gloves that are partially covered with an electrically conductive layer. To close the electrical circuit, the stimulating current flows from one glove into the patient's skin then back to the second glove. This invention is only suitable for stimulating large areas of the skin but cannot be used for intra-operative neurostimulation since the electrical current flows from one glove to the other glove. This would produce a large flow of current circulating through the skin that would not depolarize a nerve or would not be localized enough to give valuable information in order to monitor the nerve location or assess on the nerve health. Further, Berlant describes a manufacturing technique to make an electrical layer on a glove by dipping a former in a natural rubber compound and then over-dipping it in a natural rubber loaded with a non-metallic conductive material like carbon black. This technique would work if the thickness of the conductive layer is large enough and the concentration of the non-metallic conductive material dispersed in the natural rubber compound is high enough to reach the percolation point. However, it has been demonstrated and tested that the loading of non-metallic material necessary to make an electrically conductive layer having a resistivity of 2000 Ohms or lower is so high that the mechanical properties of the conductive layer like the elongation and the tensile strength would be weak and the conductivity would be lost when the glove is stretched. This technique would not be suitable to make surgical gloves that are designed to fit tightly a surgeon's hand and therefore need to be stretched during donning. The weaker mechanical properties of Berlant's conductive layer would not meet the standard requirements for a surgical glove. It has also been demonstrated that a high concentration of carbon black dispersed in rubber would leave black traces of carbon on all objects that are in contact with the glove, which would not be acceptable in a surgical environment.

In the U.S. Pat. No. 6,584,359, Motoi discloses stimulation gloves for resolving wrinkling, sagging and such of skin conditions. Similar to the '478 glove of Berlant, two gloves are used to generate a flow of alternative current squarewaves through large areas of the skin. Even if this way of stimulation is useful in providing a cosmetic effect on the skin, it would not depolarize nerves and gives valuable information for neuromonitoring purposes.

In the U.S. Pat. No. 6,904,614, Yamazaki et al. disclose a pulse health appliance with a glove that comprises a pair of electrodes in order to electrically stimulate an outside portion of the human body. This method uses a glove on which patch electrodes and electrical conductors are made of conductive woven cloth mounted on the external surface of the glove. At least one stimuli electrode and a second reference electrode are placed on the glove. This invention is only suitable for stimulating by palpation some localized external region of the body but cannot be used for intra-operative neurostimulation since the electrical current flows from the stimuli electrode on the glove to the reference electrode on the glove. This would produce a large flow of current circulating through the skin that would not depolarize a nerve or would not be localized enough to give valuable information in order to monitor the nerve location or assess on the nerve health.

In the U.S. Pat. No. 7,128,741, Isaacson et al. describe a method of transmitting electrical energy to wireless electrosurgical instruments through an electrode pad upon which the surgeon stands and through an electrical path disposed in the surgical gown and gloves. This invention is limited to transmitting electrical energy to electrosurgical devices as electrocautery or electro-coagulation devices. It is well known that it is difficult, if not impossible, to perform neuromonitoring during electrosurgery due to the fact that electrosurgery uses high frequencies, including radiofrequencies, and high voltages to cut through and coagulate tissues, and this causes important noise perturbation of the neuromonitoring signals. It would be extremely difficult to transmit neurostimulation signals through an electrode pad since the electrical signals have significantly smaller amplitude and undesirable artifacts would be generated and would affect the measurements. Further, Isaacson tries to control the activation or the operating modes of the electrosurgical device by wirelessly communicating signals from the instrument to the electrosurgical generator using a battery powered transmitter placed inside the electrosurgical instrument. As discussed above for Vise's '771 and Zhang's '312 patents, transmitting electrosurgical currents through the gown and glove presents an important risk of electrocution or injury to the patient if the surgeon inadvertently touches the body of the patient when using the electrocautery device. Another limitation of Isaacson's invention is that a battery assembled inside the electrosurgical instrument is required in order to supply power to the wireless transmitter which controls the electrosurgical generator. It is well known that steam sterilizable batteries are expensive and don't last long.

In the U.S. Pat. No. 6,141,643, Harmon describes a glove that has at least two electrical pads, one being positioned on the fingertip and the other being positioned on the palm portion. Both electrical pads are operatively connected to an output connector. Making a contact between the finger pad and the palm pad generates a signal. This invention relates to generating electrical signals for communication purposes using electrical contacts on a non-surgical glove and therefore far away from the surgical glove used for neurostimulation purposes described in the present invention. Further, Harmon's invention requires that at least one electrical pad and a second reference electrical pad are placed on the glove in order for an electrical current to flow through when both electrical pads are in contact.

In the U.S. published patent application 2010/0010367, Foley et al. disclose a method of adhering a small electrode on the fingertip of a standard surgical glove for locally stimulating tissues during anterior spine surgery and allowing IONM equipment to determine the health status and/or the location of the nerves. The lead wire that connects the electrode to the IONM system needs to be adhered or attached along the glove and the arm of the surgeon. Despite the fact that this electrode can send stimulation current by palpation into the body for IONM purpose, it is not suitable for transmitting stimulation currents to wireless instruments. Moreover, the electrode and the lead wire are add-ons to the surgical glove that affect the tactile feeling of the surgeon at the locations where the electrode and the lead wire are attached. It will also reduce the freedom of movement of the surgeon's hand during the procedure and may present an important risk of grabbing soft tissues when the surgeon's hand is inside the wound. It is well known that adhering something on a glove made out of cured rubber is very difficult and even more when the rubber is in contact with blood and body fluids. Therefore, there is a high probability that the electrode or the lead wire become loose after a short period of use and requires to being reattached or replaced and then increase the time of the procedure. A partially loosened lead wire may also involuntary grab instruments or other things that could be in the way during movements of the surgeon's arm. Moreover, during many surgeries, areas that need to be stimulated are not accessible by palpation with a finger and there is a need to use instruments.

What is needed is a neuromonitoring system that has a glove with a single stimulating electrode and an independent reference electrode in a spaced apart relationship on the glove at a surgical site in such a fashion that the electrical current flows from the glove to the reference electrode through the patient body.

Further, there is a need to quickly interconnect multiple wireless surgical instruments with an electrical source of stimulation to insure that the surgeon is constantly stimulating the surgical site to allow neuromonitoring to occur.

Still further, there is a need for a neuromonitoring system that has a glove with a single stimulating electrode for rapidly holding and electrically connecting to a wireless surgical instrument.

Yet still further, there is a need for a neuromonitoring system that has a glove with a single stimulating electrode for rapidly holding and electrically connecting to a wireless surgical instrument, where the stimulating electrode and its connection path are manufactured thin enough and completely integrated in the glove to not affect the mechanical properties of the glove and not change the tactile feeling of the surgeon.

Still yet further, there is a need for a neuromonitoring system that has a glove with a single stimulating electrode for rapidly holding and electrically connecting to a wireless surgical instrument, where the addition of the stimulating electrode, its connection path and the surgical instrument have an electrical resistivity below 2000 Ohms and where the surgical glove has mechanical and biocompatibility properties that meet the required standards for surgical gloves.

Further still yet, there is a need for a neuromonitoring system that has a glove for transmitting a low frequency, low voltage electrical stimulation that will not harm the tissue if the glove inadvertently touches the patient.

Still yet further, there is a need for a kit of electrically conductive surgical instrumentation and access tools that wirelessly work with a glove stimulator.

Further still yet, there is a need for a kit of electrically conductive surgical instrumentation and access tools that wirelessly work with a glove stimulator where the IONM specialist can remotely control the stimulation input.

DEFINITIONS

The meanings of the following terms used in the description of the present invention have been defined as the following:

End effector: portion of the instrument that is used to perform the intended function.

Wireless: means of connection made between the glove and an instrument without the use of a wire or a connector.

Electrically conductive open surface: surface that is electrically conductive and from which an electrical current can be transmitted when contact is made with another electrically conductive object.

SUMMARY OF THE INVENTION

The present invention provides methods and apparatus that allow the surgeon and the IONM specialist to continuously get feedback on the relative proximity of instrumentation to a nerve and the health of this nerve. By having a coupling device that allows every instrument to be electrically stimulated, the surgeon, through the instruments, continuously sends a small electrical input into the patient's body. Depending on the relative proximity between this electrical stimulation and a nerve, a neuromonitoring modality is recorded through electrodes placed on the patient. This modality is read and analyzed by the IONM specialist. The characteristics of this response allow the IONM specialist to determine the health status and or location of the nerves.

Traditional couplings between instruments and a power source take time to connect and reconnect and are often overlooked as the surgeon's main focus is accomplishing the surgical task at hand. Further, those instruments are not easily adaptable and need to be highly redesigned in order to integrate wired electrical connections, especially for rotational instruments like screwdrivers. Due to the fact that the neuromonitoring specialist is not in the sterile field to observe the lack of electrical continuity often the instruments go un-electrified and the neuromonitoring specialist sees no response indicating that there are no nerve complications when in fact the surgeon may be in the proximity of the nerve and causing damage. By integrating the power connection directly into the surgeon's glove, coupling steps are removed from the surgery allowing all of the instruments in use to be electrified without further thought from the surgeon.

Beside the fact that all instruments will have the option to be electrified, the surgeon can also directly stimulate with his finger. Instead of using a surgical probe to find a nervous system component, the surgeon can use the tip of his finger to stimulate and determine where those nervous system components are. Another novel aspect of this invention is the manner in which the glove is manufactured so that the conductive pathway does not influence the tactile feeling of the surgical glove like wires or patches.

This novel invention proposes a new coupling method between instruments and an electrically stimulating source in order to insure constant stimulation with low current when performing surgeries. By constantly stimulating into a patient's body, it is possible to get feedback on the health of the nerves through neuromonitoring modalities without any potential harm to the patient due to the currents used.

BRIEF DESCRIPTION OF THE DRAWINGS

FIG. 2 shows a side view of a person wearing a surgical gown and glove of the present invention.

FIG. 3 shows a top view of the electrical connection between the novel electrifiable surgical glove and the gown.

FIG. 3A is a cross sectional view of FIG. 3 of the present invention.

FIG. 3B is an alternate cross sectional view of FIG. 3A of the present invention.

FIG. 7 is a top view of a hand with the electrifiable surgical glove of an alternate embodiment demonstrating the detection of the electrical connectivity to a surgical instrument.

FIG. 8 is a bottom view of another alternate embodiment of the surgical glove of the present invention.

FIG. 35 shows the bottom half of a stretchable wire.

FIG. 36 shows the upper half of a stretchable wire.

FIG. 37 shows a cross section of the bottom half of a stretchable wire.

FIG. 38 shows a cross section of the upper half of a stretchable wire.

FIG. 39 shows the assembly of the two halves of a stretchable wire.

DETAILED DESCRIPTION OF THE INVENTION

Figure 1:
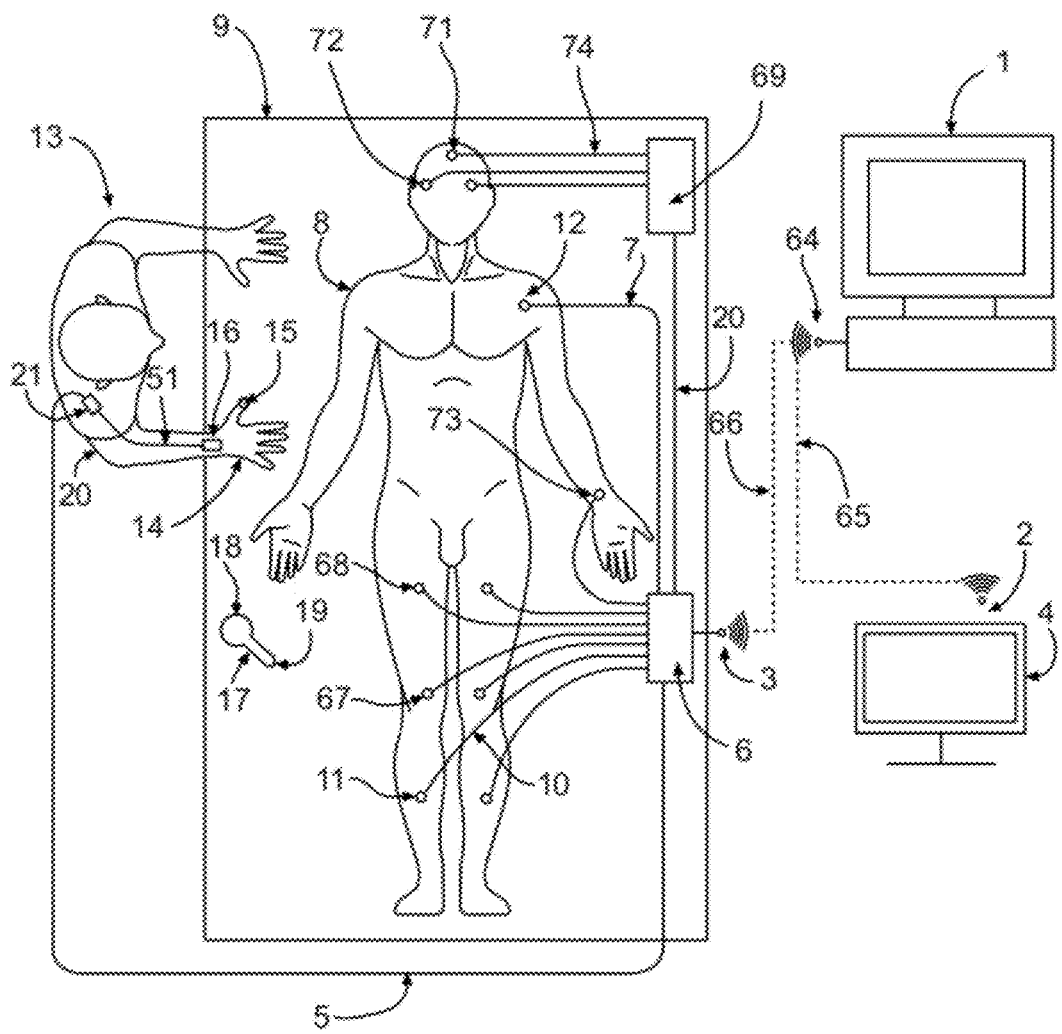
FIG. 1 shows a top view of an operating room with an exemplary set-up of the novel neuromonitoring system.

In FIG. 1, the surgeon 13 is illustrated next, and hopefully performing, to a patient 8, positioned on a surgical table 9, undergoing a lower lumbar spine surgery. Neuromonitoring and stimulation devices are installed on the patient to provide information to the IONM specialist through the neuromonitoring computer system 1. EMG electrodes 11 are placed on the lower limbs to monitor free-run EMG. Stimulating SSEP electrodes 67 are placed on the lower limbs to send an electric signal that will be used to measure the SSEP modality with the SSEP electrode 71 placed on the head of the patient. Stimulating TcMEP electrodes 72 are placed on the head of the patient and sent an electrical input that is measured with the TcMEP electrodes 68 placed on the lower limbs of the patient. Train-of-four input electrodes 73 are placed on the arm of the patient and used to measure the affects of the muscle relaxant. Although not all shown, anode electrodes or reference electrodes are present in order to complete the electrical circuits. Neuromonitoring modalities can be adapted, added or relocated depending on the type of surgery. Stimulating electrodes can be needle electrodes inserted into the skin or surface electrodes or alternately stimulation may be done by a wireless instrument 17. Sensing electrodes can be needle electrodes, surface electrodes or any other kind of mechanical, electrical or optical sensors such as accelerometers, gyros, strain gages, pressure sensors, fiber optics or acoustic sensors.

In a lower lumbar spine surgery, lower limb are monitored and neuromonitoring modalities are wired to the main connection box 6 through connection wires 10. Alternately multiple connection boxes may be used for instance one for the left side of the patient and another for the right side of the patient. Head neuromonitoring modalities are wired to the remote connection box 69 trough connection wires 74. The remote connection box 69 is wired to the main connection box 6 trough wire 70 or alternately wirelessly connected directly to the computer system 1. In another configuration, the remote connection box 69 may not be used and all the neuromonitoring wires 10, 74 would be connected to a single connection box 6. In the preferred embodiment, the main connection box 6 has a wireless connection 66 to the neuromonitoring computer system 1 through a wireless transmitter 3. The neuromonitoring computer system 1 has wireless connections to the main connection box 6 and the remote screen 4 through a wireless transmitter 64. Connection box 69 and connection box 6 are adapted to be placed under the surgical site preparation to avoid issues of sterilization, however it is contemplated that these boxes would be located within the surgical field. In a traditional set-up these junction boxes 6, 69 would be hardwired to the computer system 1. However it is desirable to eliminate wiring from the connection boxes to the computer eliminating electrical cords crossing the sterile field eliminating sources of unwanted noise and simplifying the concerns of signal contamination from electrosurgical devices. Alternately the invention should not be limited to wireless connectivity as wireless connection 65 and wireless connection 66 could both be hardwired should the IONM tech desire.

In the preferred embodiment, the remote screen 4 has a wireless connection 65 to the neuromonitoring computer system 1 through a wireless transmitter 2. The remote screen 4 is a display screen that can be positioned anywhere in the operating room, generally in a line of sight of the surgeon or for visualization by other members of the medical team or by the sales representative who are frequently assisting with surgical protocol information. The information displayed on this screen is either a supplementary feedback generated by the IONM specialist or real time information automatically generated by a computer algorithm computerized at the neuromonitoring computer system 1 such as nerve avoidance algorithms with color coded signals allowing the surgeon to see or hear his approach towards a nerve. The remote screen may also communicate such information as necessary for the surgeon to understand when he is in electrical contact with the surgical instrument 17, when he is sending stimulating current into the body and different useful information on status and modes of the neuromonitoring system.

The surgeon 13 wears an electrifiable surgical glove 14 that includes at least one electrical conductive open contact surface 15 to hold the instrument 17. The electrifiable surgical glove 14 is electrically connected to the gown 20 through an electrical sleeve connection 16. In turn, the electrical sleeve connection 16 is electrically connected to the gown electrical path 51 which then connects to the electrical gown connection 21. The main electrical path 5 connects to the gown 20 through the electric gown connection 21 to the main connection box 6 which contains pre-amplifiers for sensing electrodes and stimulators for generating electrical stimulation currents. Although not shown, a common electrode is usually placed on the patient's skin to provide a ground reference to the pre-amplifiers of the main connection box 6. The main electrical path 5 has at least one conductor to send an electrical stimulation current to the electrifiable surgical glove 14. In order to close the electrical circuit and provide a return path for the stimulation current, reference wire 7 is connected to main connection box 6 and is placed on or into the patient's skin through the reference electrode 12. This reference electrode is also called anode electrode, the cathode being the instrument 17 that sends the stimulations. The reference electrode 12 is usually placed in the near proximity of the surgical site, in the opposite side of the opening. Therefore, most of the nerves to monitor are located in between the reference electrode and the source of electrical stimulation in such a way that the current flows through a short portion of the patient's body. In all cases, the reference electrode is placed far away from the ground electrode of the electrosurgical device in order to attenuate potential artifacts. The electrical stimulation current flows through the electrified glove 14 via the electrically conductive wireless surgical instrument 17 into the patient's body, to the reference electrode 12.

Figure 1A:
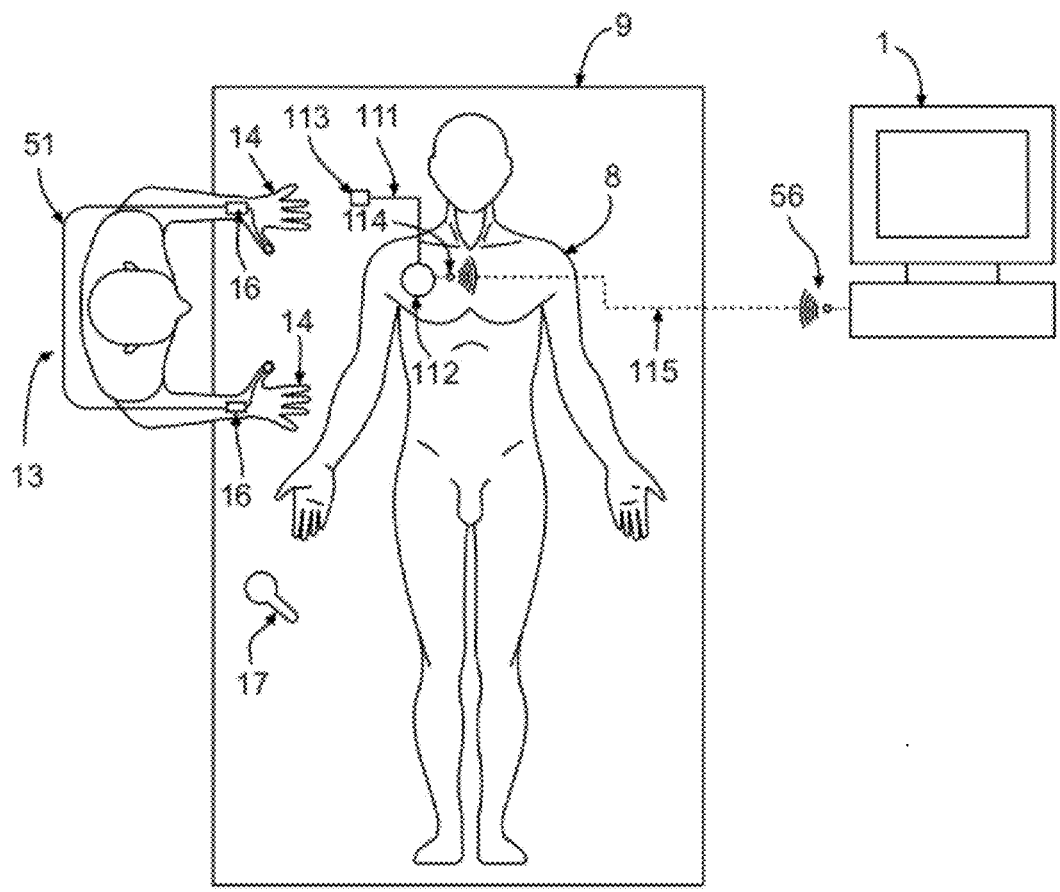
FIG. 1A shows a top view of an operating room with an alternate embodiment of the set-up of the novel neuromonitoring system.

An alternative glove connection to FIG. 1 is shown in FIG. 1A where the surgeon may wear two electrifiable gloves 14 that are electrically connected via the gown electrical path 51', which goes from one side of the surgeon's electrical sleeve connection 16 to the other side. A stimulator 112 having a reference electrode placed on or into the patient's skin and a wireless transmission 115 to the neuromonitoring computer system 1 is located on the patient as shown or alternately carried by the surgeon not shown. The stimulator has a wireless transmitter 114 in communication with the neuromonitoring computer system transmitter 64. In order to electrify the instrumentation the surgeon 13 closes the electrical circuit by holding the handle 113 of the remote wire 111 with one hand and the instrument 17 in the other hand. In this fashion the surgeon 13 is not in a wired connection with the surgical field and is free to move about unencumbered and may close the loop to stimulate in any location in relationship to the patient 8. The wireless stimulator 112 has a small battery that provides energy to the electronics to generate the electrical stimulations during the surgery and insure wireless communication with the computer system 1. Further, the wireless stimulator unit may be a single-use sterile device.

For either configuration shown in FIG. 1 or 1A in order to perform a surgical procedure, the surgeon 13 uses a wireless electrifiable surgical instrument 17 that has an electrically conductive handle 18. It is desirable to have a tactile feeling in the handle 18 while making it comfortable for the surgeon 13 to use and may be molded from an electrically conductive silicone or soft electrically conductive material such polyurethane or TPE. Alternatively it could also be made from metal, however to reduce the weight of the instrument it may be preferred to hollow out the metal handle 18. The handle 18 must then be in electrical contact with the instrument's end effector 19 so that an electrical current may be sent through it. An electrically insulating over-coating usually covers most of the body of the instrument. The end effector 19 is the only electrical conductive open surface of the distal portion of the instrument and has only a few square millimeters. In different embodiments, the instrument may have multiple end effectors. The small size of the open conductive surface is very important for getting accurate results on nerve location and nerve health assessment. To large of a surface would spread the stimulation current into wider areas of tissue and body fluids and stimulation current threshold needed for depolarizing a nerve from a certain distance would be affected and therefore wrong indication of safety would be given to the IONM specialist and surgeon. It is important that the currents being sent through these surgical gloves 14 and instrumentation 17 be relatively low, for instance below 200 milliamps of current, in comparison to electrosurgical devices like electrocautery or powered tools which operate at inherently higher more dangerous current levels. In this manor the surgeon 13 will be free to palpate the patient 8 with the glove 14 directly without exposing the patient or the surgical team any risk of being shocked. In this way the surgeon 13 is free to focus on the surgical procedure and to be continually stimulating the surgical site through various tools 17 and end effectors 19 or the glove 14 in order that the IONM or the surgeon may monitor the activity of the nerves to avoid injury and ensure patient safety during the procedure.

In FIG. 2, the gown electrical path 51 is isolated along the gown 20 and in a preferred embodiment delivered along with electrical connections 16 and 21 as part of the gown in a single-use sterile condition to the hospital. Alternatively the gown electrical path 51 and the electrical connections 16 and 21 may be delivered as an independent sterile item which is subsequently attached to an existing sterile gown 20 by some known attachment method such as a tape or an adhesive. The electrical gown connection 21 can use any electrical connector but preferably a connector that holds well but can be disconnected with a small tug as the surgeon 13 moves away from the surgical table 9. The connection 16 should also easily be connected to the glove 14 while the surgeon 13 is gowning and should also be easily removable should the surgeon decide to change gloves during the procedure.

In FIGS. 3, 3A and 3B the electrical sleeve connection 16 connects the electrifiable surgical glove 14 to the gown 20. In the preferred embodiment, there are two glove electrical conductive open contact surfaces 22, 23 on the electrifiable surgical glove. Those two glove electrical conductive open contact surfaces 22, 23 are electrically connected to the gown through electrically conductive adhesive tapes 35, 76 that connect to the electrical connection patches 24, 25 mounted on the gown. Connection patches 24, 25 connect to conductors 52, 53 that compose the gown electrical path 51. Electrically conductive adhesive tapes 35, 76 are part of the glove and mounted on an isolated strip 34. At the opening of the sterile single-use packaging containing the electrifiable surgical glove, the pull-protecting tab 33 covers the adhesive portion of the electrically conductive adhesive tapes 35, 76 as shown in FIG. 3B which is an alternate cross section for FIG. 3A. After the surgeon put his/her hand in the electrifiable surgical glove, the pull-protecting tab 33 is pulled (75) to unprotect the adhesive portion of the electrically conductive adhesive tapes 35, 76 and the electrical connection is made to electrical connection patches 24, 25. When the surgeon wants to remove his/her hand from the electrifiable surgical glove, the pull-protecting tab 33 is pulled away (56), which breaks the adhesion between the conductive adhesive tapes 35, 76 and the electrical connection patches 24, 25. Alternatively it is contemplated that the adhesive tapes 35, 76 could carry wires not shown which would replace the electrical conductivity of the tape. In this case the adhesive would simply act to hold the wires in electrical contact with the glove. The location of the electrical connection on the glove is important and placed in such a way that disturbance is minimized. It has been shown that the area of the top of the hand, between the wrist and the first joints of the fingers, is a good location but sometime in the way when the surgeon needs to insert his/her hand deep inside the wound. In the preferred embodiment, the electrical connection is made on the top of the hand, in the middle of the glove cuff, below the wrist joint. This portion of the glove is usually pulled over the gown cuff and would not affect the tactile feeling or reduce the freedom of movements of the surgeon. A little space between the electrical connection and the far end of the glove cuff is avoided, usually over 25 mm, in order to facilitate handling of the glove during donning. This portion of the glove is also the most stretched part and placing the electrical connection there would increase the risk of damaging them when putting the glove on the hand. Further, it is understood that the sleeve connection 16 is not limited to the described preferred embodiment and could be made of any other mechanical/electrical connection, including electrical conductive hook and loop tape (Velcro®). The sleeve connection 16 could also be placed all around the glove cuff.

Figure 3C:
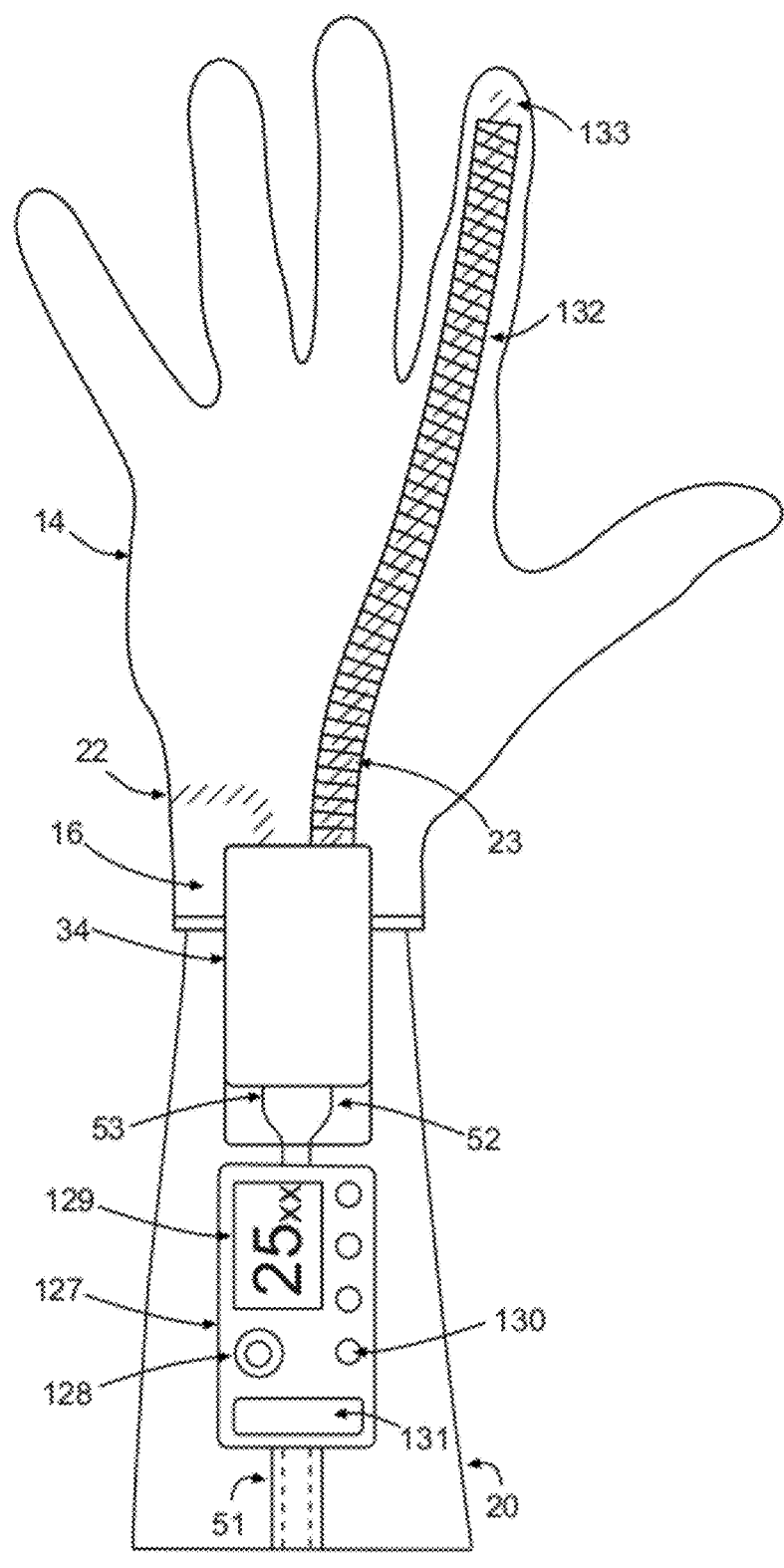
FIG. 3C shows an alternate embodiment of the electrical connection between the electrifiable surgical glove and the gown with an electronic I/O module that gives direct feedbacks to the surgeon.

In FIG. 3C, the electronic module 127 gives feedbacks to the surgeon on the status of the nervous system. The module includes lights 130 to indicate the proximity of the instrument to a nervous system component and could also, indicates if the electrifiable glove holds a surgical instrument. The module also includes a switch 131 that can turn on or off the electrical stimulation that is transmitted to the electrifiable glove. The digital screen 129 displays lettered or numbered feedback to the surgeons and the scroll wheel, trackball or joystick 128 is used to control and navigate through the menus and information displayed on the remote screen 4 shown on FIG. 1. The electronic module 127 can be placed on the electrifiable 14 glove, the gown 20 or the isolated strip 34 between the glove and the gown. The electronic module may also emit different sounds or vibrations to give feedbacks to the surgeon on the status of the nervous system. In a different embodiment, the electronic module that emits sounds may be placed in the collar of the surgical gown, closer to the surgeon's ears. In this configuration, the gown electrical path 51 may include additional electrical conductors that form a data bus, as example similar to the Universal Serial Bus (USB). In reference to the preferred embodiment described above, this data bus is connected and exchanges data with the neuromonitoring computer system 1 through the connection box 6.

Figure 4:
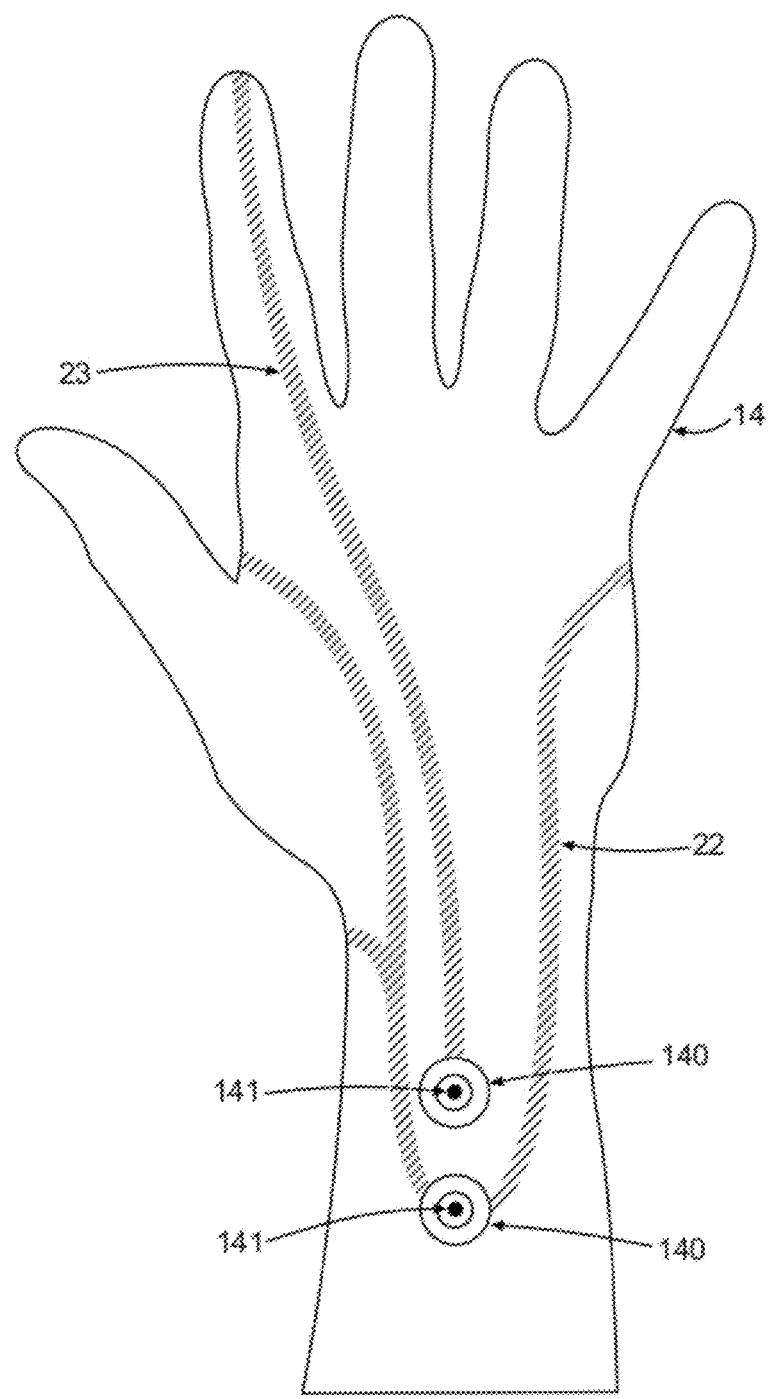
FIG. 4 is a top view of an alternate embodiment of the electrical connection between the surgical glove and the neuromonitoring computer system.

In FIG. 4, another embodiment of the electrical connection between the surgical glove 14 and the neuromonitoring computer system 1 is shown. Electrode patches 140 are fixed to the surgical glove, creating an electrical contact to the glove electrical conductive open contact surfaces 22, 23. The electrode patches 140 are made with an electrode male stud 141 that clips into the electrode clip 142 of the electrode connectors 145. As discussed, the electrical connection is made on the top of the hand, in the middle of the glove cuff, below the wrist joint in order to not affect the tactile feeling or reduce the freedom of movements of the surgeon and avoid excessive stretching of the electrode patches during donning.

Figure 4A:
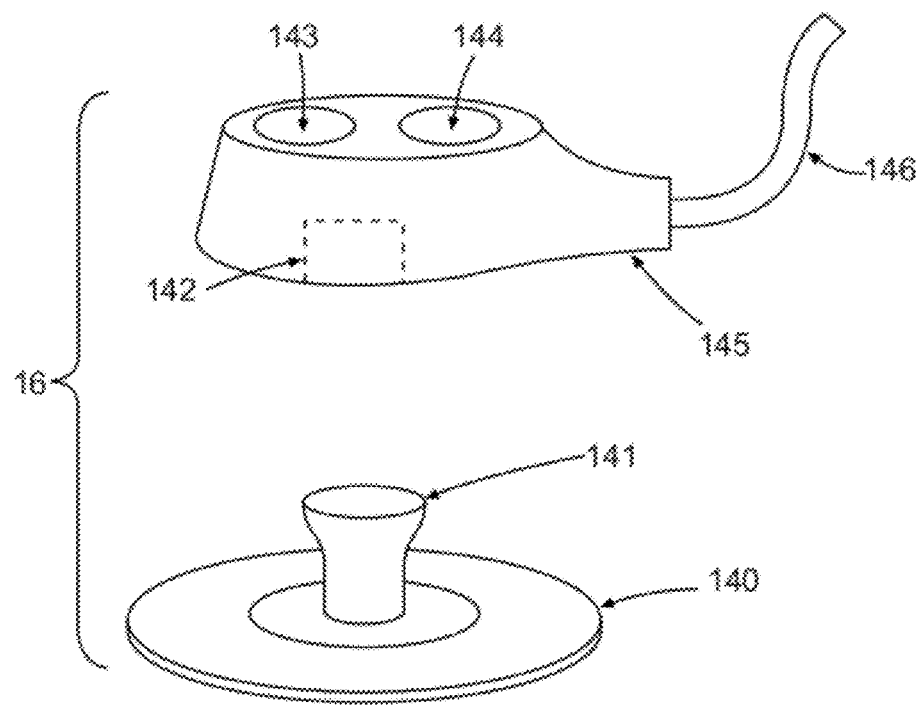
FIG. 4A is an isometric view of an assembly of the electrode patch and the electrode connector.
Figure 4B:
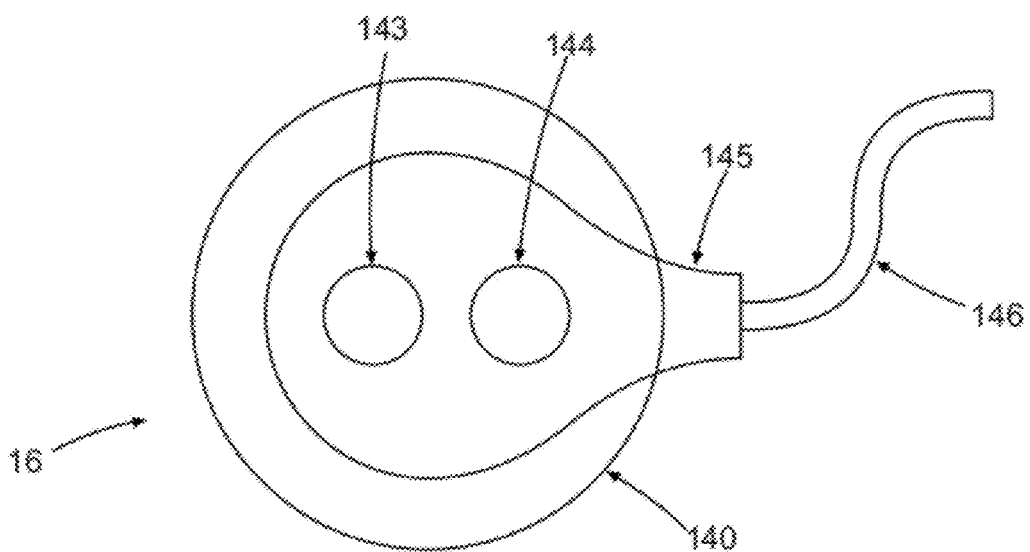
FIG. 4B is a top view of an assembly of the electrode patch and the electrode connector.

In FIG. 4A, an assembly of the electrical sleeve connection 16 that comprises at least one electrode patch 140 and the mating electrode connector 145 is shown. In order to create an electrical connection between the electrode patch 140 and the electrode connector 145, the electrode male stud 141 clips into the electrode clip 142. The electrode connector 145 has a wire 146 that is connected to the neuromonitoring computer system 1 and transmits the stimulation current to the electrode clip 142. In another embodiment, a light 143 and a switch 144 are mounted on the electrode connector 145. The light 143 informs the surgeon on the proximity of a surgical instrument to a nervous structure. The switch 144 allows the surgeon to turn on and off the stimulation current and also, to switch from the right side to the left side surgical glove and select which electrical path is stimulating. FIG. 4B shows a top view of FIG. 4A.

Figure 5:
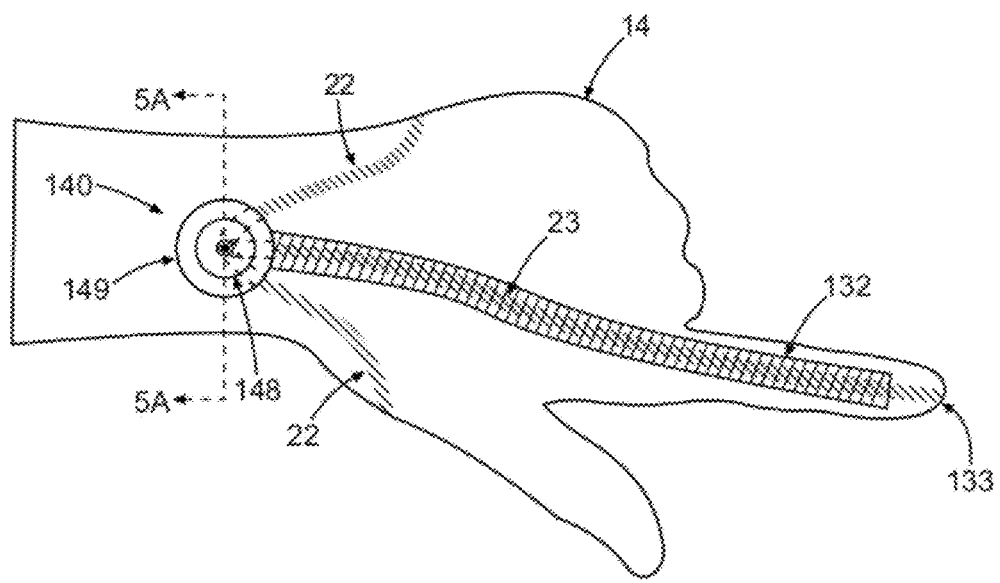
FIG. 5 is a top view of a bipolar electrical connection between the surgical glove and the neuromonitoring system.
Figure 5A:
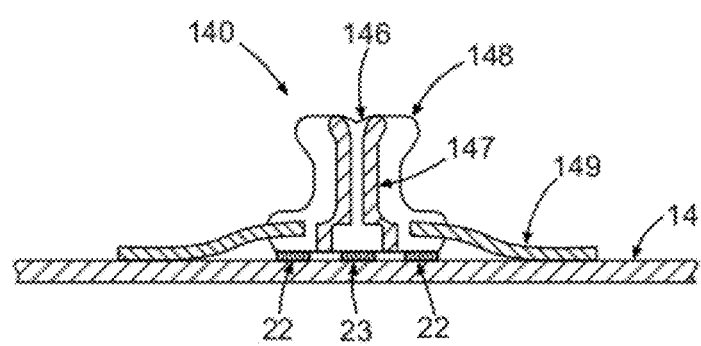
FIG. 5A is a cross section view of the bipolar electrical connector.

In FIG. 5, a bipolar electrode patch 140 is used to make the electrical connection between the surgical glove 14 and the neuromonitoring computer system 1. In this embodiment, only one electrode patch 140 is fixed to the surgical glove, creating both electrical contacts to the glove electrical conductive open contact surfaces 22 and 23. FIG. 5A shows a cross section of the electrode patch 140. The central portion of the male electrode stud 146 ensures the electrical connection with the conductive path 23. The outside portion 148 of the stud ensures the electrical connection with the conductive path 22. An isolative portion 147 in between the two poles ensures electrically independence of the electrical paths. An O-ring (not shown in the figure) may be used to seal the electrical connections between the stud and the connector from liquid or blood entering inside the connection and potentially short-cutting the electrical signals. The adhesive portion 149 of the electrode patch 140 is firmly attaching the bipolar electrode patch on the surgical glove 14. With the same idea of what is described in FIG. 4A, a bipolar electrode connector is clipped onto the male electrode stud to ensure electrical connections to the neuromonitoring computer system 1. As discussed before and still in the preferred embodiment, the electrical connection is made on the top of the hand, in the middle of the glove cuff, below the wrist joint in order to not affect the tactile feeling or reduce the freedom of movements of the surgeon and avoid excessive stretching of the connection during donning.

Figure 6:
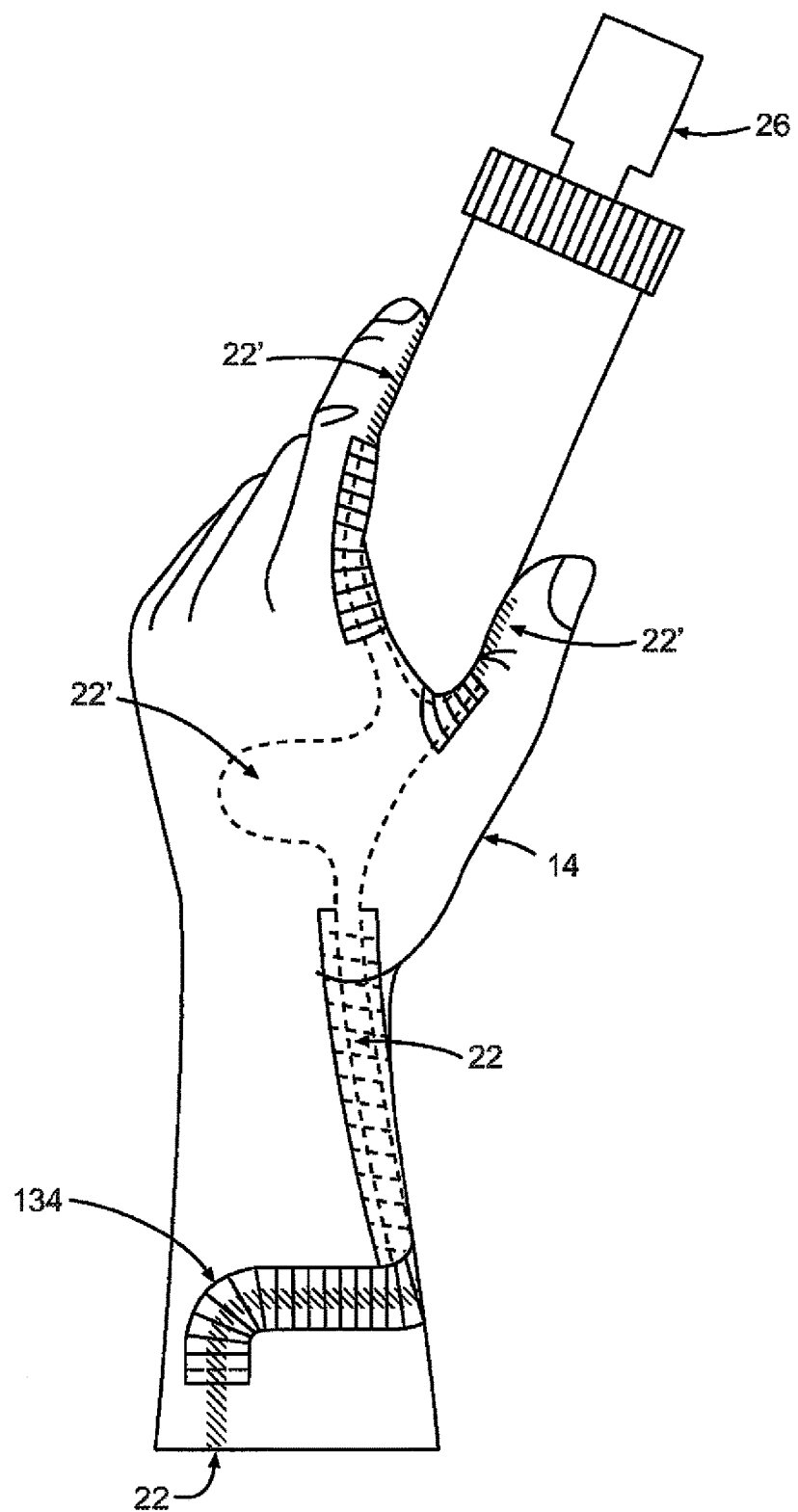
FIG. 6 is a right side view of a hand with the electrifiable surgical glove of the preferred embodiment demonstrating electrical connectivity to a surgical instrument.
Figures 6A, 6B:
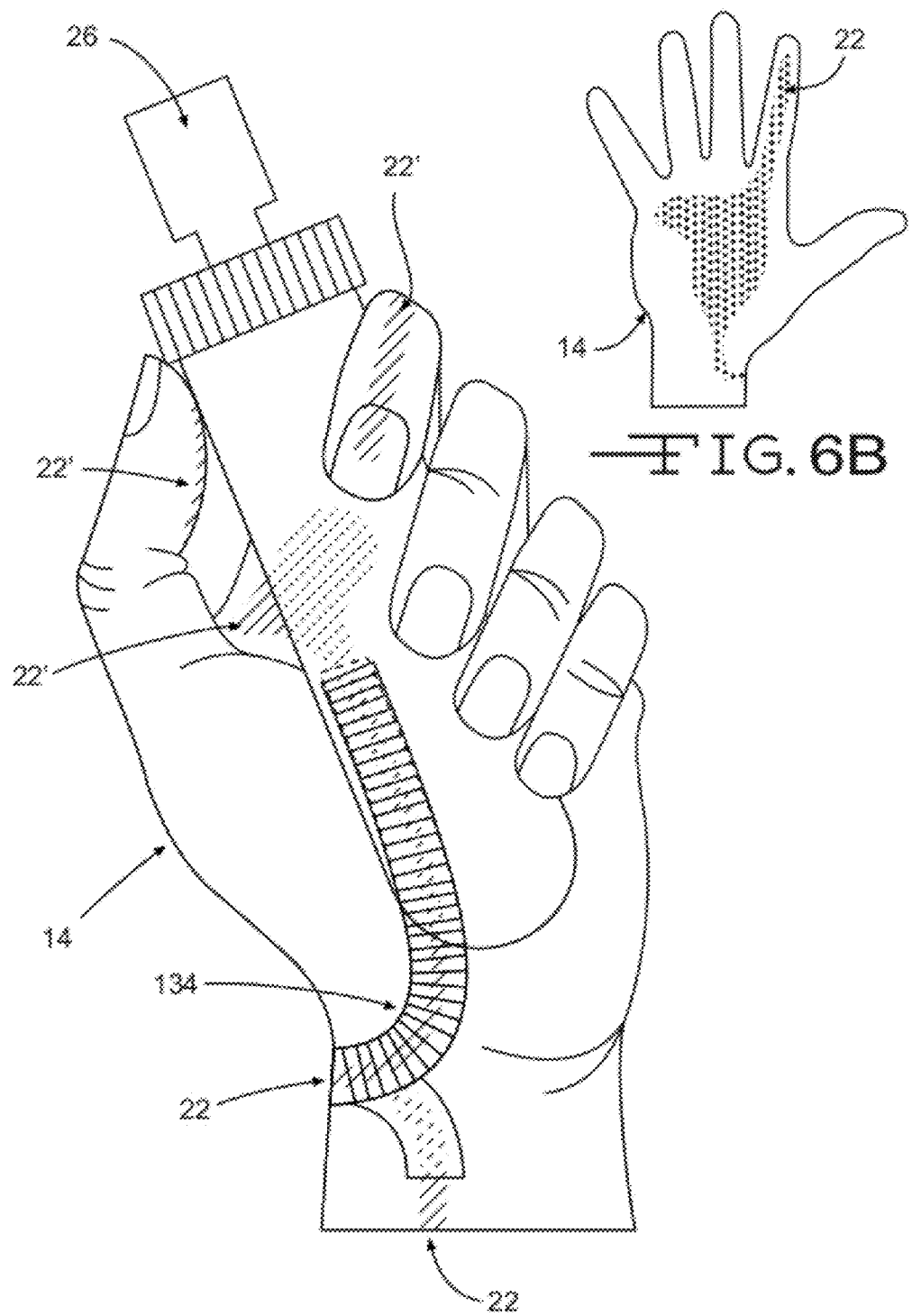
FIG. 6A is a bottom view of a hand with the electrifiable surgical glove of the preferred embodiment demonstrating electrical connectivity to a surgical instrument.
FIG. 6B is a bottom view of an alternate embodiment of the surgical glove of the present invention.

In the preferred embodiment shown in FIGS. 6 and 6A the electrifiable surgical glove 14 has at least one glove electrical conductive open contact surface 22 on its outside surface. The at least one glove stimulating conductive open contact surface 22 is used to transmit the stimulation current in the wireless instrument 26. The stimulation electrical current flows through the electrified glove via an electrically conductive wireless surgical instrument 26 into the patient's body to the reference electrode 12 also shown in FIG. 1. When the stimulation electrical current flows, the closing of the electrical circuit, between the glove electrical conductive open contact surface 22, the electrically conductive wireless instrument, the patient's body and the reference electrode 12, is detected by either the neuromonitoring computer system 1 or the main connection box 6, and the IONM specialist is informed that the instrument is connected to the glove and stimulating into the patient's body. Moreover, the feedback of the instrument stimulating can also be displayed on the remote screen 4. In order to limit the surface area of the electrical open conductive surface, an insulating coating 134 may partially cover the open conductive surface. In this way, the electrical open conductive surfaces 22' are mainly located where the wireless surgical instrument is touching the glove and chance to inadvertently send stimulation current into the patient's body is limited. Still in the preferred embodiment, the open conductive surfaces 22' are located on the palm side of the glove, on the internal face of the index and on the internal face of the thumb. All the other areas are over-coated with an isolative layer. It is understood that the disposition and shape of the glove electrical conductive open contact surface 22 is not limited to what is shown. FIG. 6B shows another pattern of the glove electrical conductive open contact surface 22 without any isolative over-coating. It is also understood that the electrifiable surgical glove can have more than one stimulating electrical conductive open contact surface 22 in order to make electrical contact with multiple electrical portions of a wireless instrument.

Figure 7A:
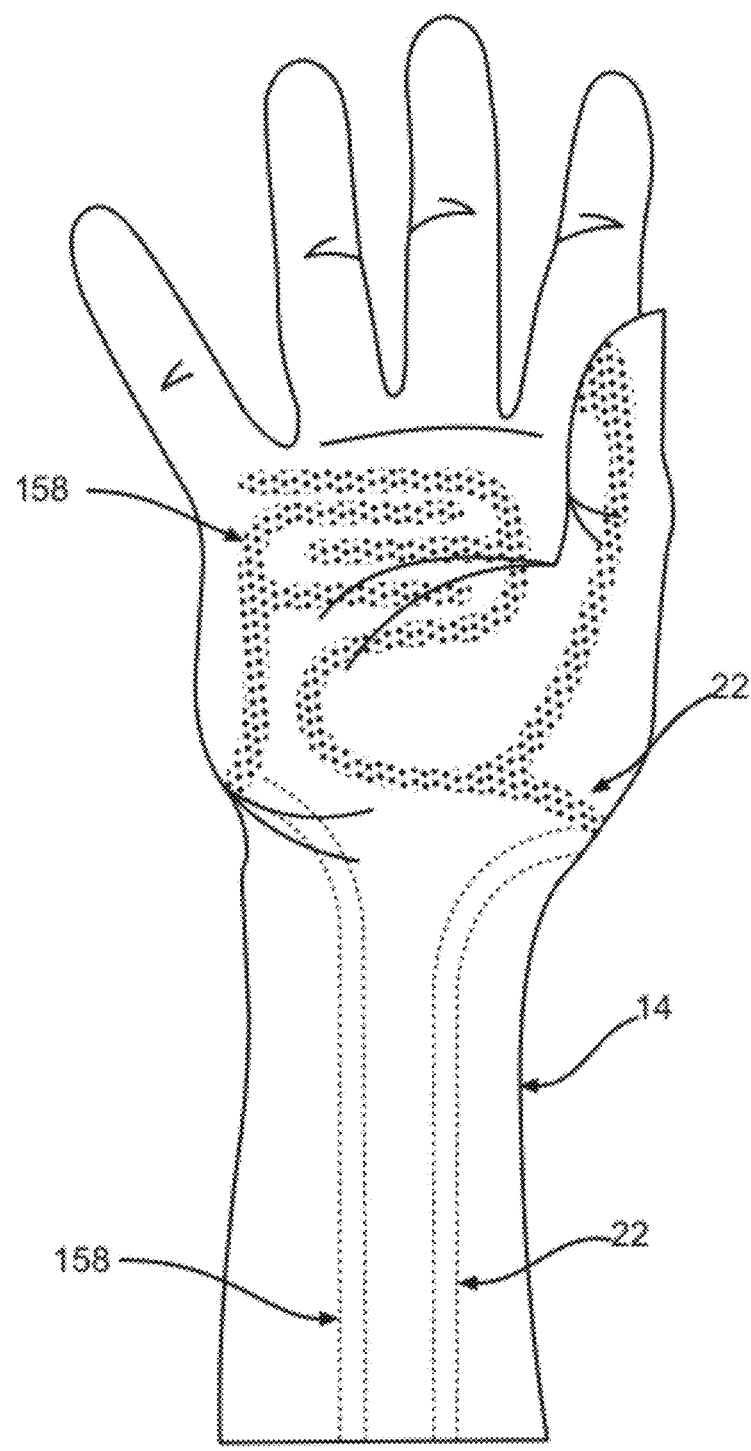
FIG. 7A is a top view of a hand with the electrifiable surgical glove of an alternate embodiment showing the electrical path for detection of the electrical connectivity to a surgical instrument.

In a different embodiment, the electrifiable surgical glove 14 shown in FIGS. 7 and 7A has a presence conductive open contact surface 158 that is used as an electrical switch that detects the presence of an electrically conductive wireless surgical instrument. The glove presence conductive open contact surface 158 is positioned in a way where it should not have contact with the patient while the instrument is in the surgeon's hand. When the surgeon closes his/her hand on the surgical instrument 26, the electrical circuit is closed between the two glove electrical conductive open contact surfaces 22, 158. So, when the electrical circuit is closed, an electrically conductive surgical instrument is in the hand of the surgeon. This is supplementary information to the IONM specialist who knows when an instrument is connected to the glove and ready to stimulate. Moreover, when the stimulation electrical current flows, the closing of the electrical circuit, between the glove stimulating conductive open contact surface 22, the electrically conductive wireless instrument, the patient's body and the reference electrode 12, is detected by either the neuromonitoring computer system 1 or the main connection box 6, and the IONM specialist is informed that the instrument is connected to the glove and stimulating into the patient's body. The automatic communication of this information to IONM specialist allows them to know if the stimulator is on and working without having to interrupt the surgeon's concentration. It also allows them to be prepared when to monitor nerve location since the instrument is likely in use while in the surgeon's hands. Moreover, the feedback on connectivity to the instrument and the instrument stimulation can also be displayed on the remote screen 4 should the surgeon want to check the connection without having to communicate with the IONM specialist. It is understood that the disposition and shape of the two glove electrical conductive open contact surfaces 22 and 158 are not limited to what is shown. It is also understood that the electrifiable surgical glove can have more than one stimulating electrical conductive open contact surface 22.

In a different embodiment shown in FIG. 8, the electrifiable surgical glove 14 has a full glove electrical conductive open contact surface 28. This full glove electrical conductive open contact surface 28 is used to transmit the stimulation current in the wireless instrument. The stimulation electrical current flows through the electrified glove via an electrically conductive wireless surgical instrument into the patient's body to the reference electrode 12. When the stimulation electrical current flows, the closing of the electrical circuit, between the glove electrical conductive open contact surface 28, the electrically conductive wireless instrument, the patient's body and the reference electrode 12, is detected by either the neuromonitoring computer system 1 or the main connection box 6, and the IONM specialist is informed that the instrument is connected to the glove and stimulating into the patient's body. Moreover, the feedback of the instrument stimulating can also be displayed on the remote screen 4.

Figure 9:
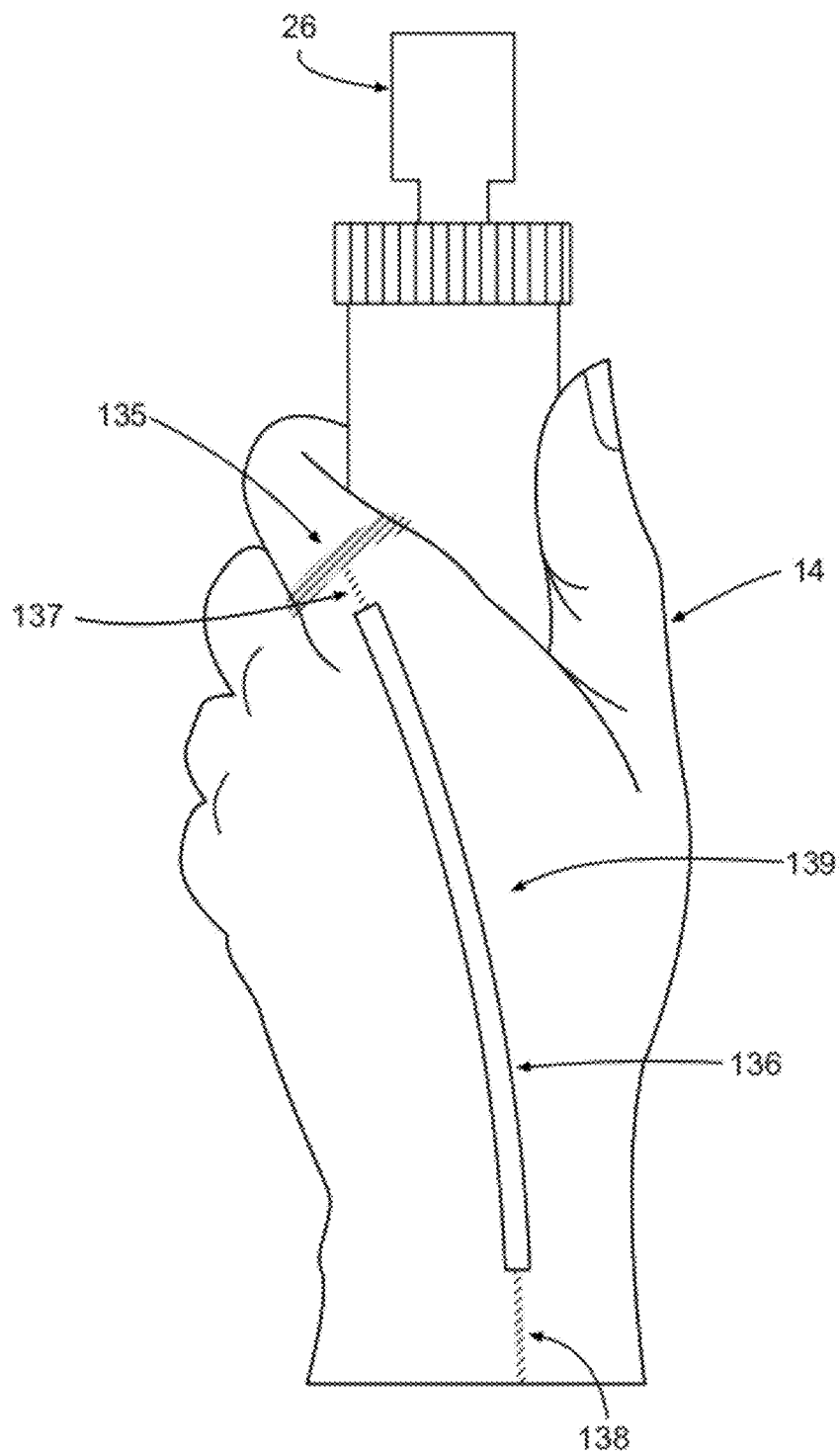
FIG. 9 is a right side view of another alternate embodiment of the surgical glove of the present invention.

In a different embodiment, the electrical conductive path may be mounted on a standard surgical glove that has been taken off its sterile packaging in the operating room and worn by the surgeon. The electrical conductive pad is supplied in a sterile condition and ready to be affixed on the surgical glove. As an example only, the electrical conductive path shown in FIG. 9 has an electrically conductive ring 135 which can be placed around a finger. It has been shown that a small ring around the finger would not disturb too much the freedom of movements of the surgeon's finger and not affect his/her tactile feeling. Moreover, the ring would be in most cases in contact with different kind of instruments that the surgeon may hold. The electrical conductor 139 has an elongated portion with two ends, one end 138 starts at the cuff side of the glove 14 and the second end 137 is connected to ring. An insulated portion 136 may be disposed between the two ends and may be used to affix the electrical conductor on the surface of the glove. The insulated portion 136 can be an adhesive tape that is stuck on the glove or any other kind of elements that will help the fixation of the electrical conductor 139 on the surface of the glove. This insulated conductor runs on the top or on the side of the finger and on the top of the hand to minimize the effect on the tactile feeling of the surgeon. The cuff end 138 is connected to the electrical sleeve connection 16 as described in the other embodiments. This electrically conductive ring 135 connected to the electrical conductor 139 and disposed around the finger, on the surface of the glove is used to transmit the stimulation current in the wireless instrument. The stimulation electrical current flows through an electrically conductive wireless surgical instrument into the patient's body to the reference electrode 12. When the stimulation electrical current flows, the closing of the electrical circuit, between the electrical conductor 139, the electrically conductive ring 135, the electrically conductive wireless instrument, the patient's body and the reference electrode 12, is detected by either the neuromonitoring computer system 1 or the main connection box 6, and the IONM specialist is informed that the instrument is connected to the glove and stimulating into the patient's body. Moreover, the feedback of the instrument stimulating can also be displayed on the remote screen 4. It is understood that the electrically conductive ring shown on this figure can be made of any other kind of electrically conductive open surface that is mounted somewhere on the surface of the glove in a location that would minimize the impact on the surgeon's tactile feeling. The electrical conductive path can be made of any electrically conductive material which can be a silicone based adhesive, a conductive polymer, a conductive fabric, or any other electrically conductive adhesive. In a different version, the electrical conductive path may be a conductive glove as describe in FIG. 6 with the fingers cut off as example. This partial glove can be worn over the standard surgical glove. The cuff end is connected to the electrical sleeve connection as described in the other embodiments. Since the partial glove doesn't act as the primarily protective barrier, its thickness can be reduced to a minimum to not affect the tactile feeling. In still a different embodiment, at least one finger cot having an electrically conductive open surface could be worn over the standard surgical glove. An electrical conductor having an insulated portion is used to connect the finger cot to the cuff end, as described previously. Since the finger cot doesn't act as the primarily protective barrier and limited mechanical strength is required, its thickness can be reduced to a minimum, in instance below 5 mils, and tactile feeling would not be affected too much.

Figure 10:
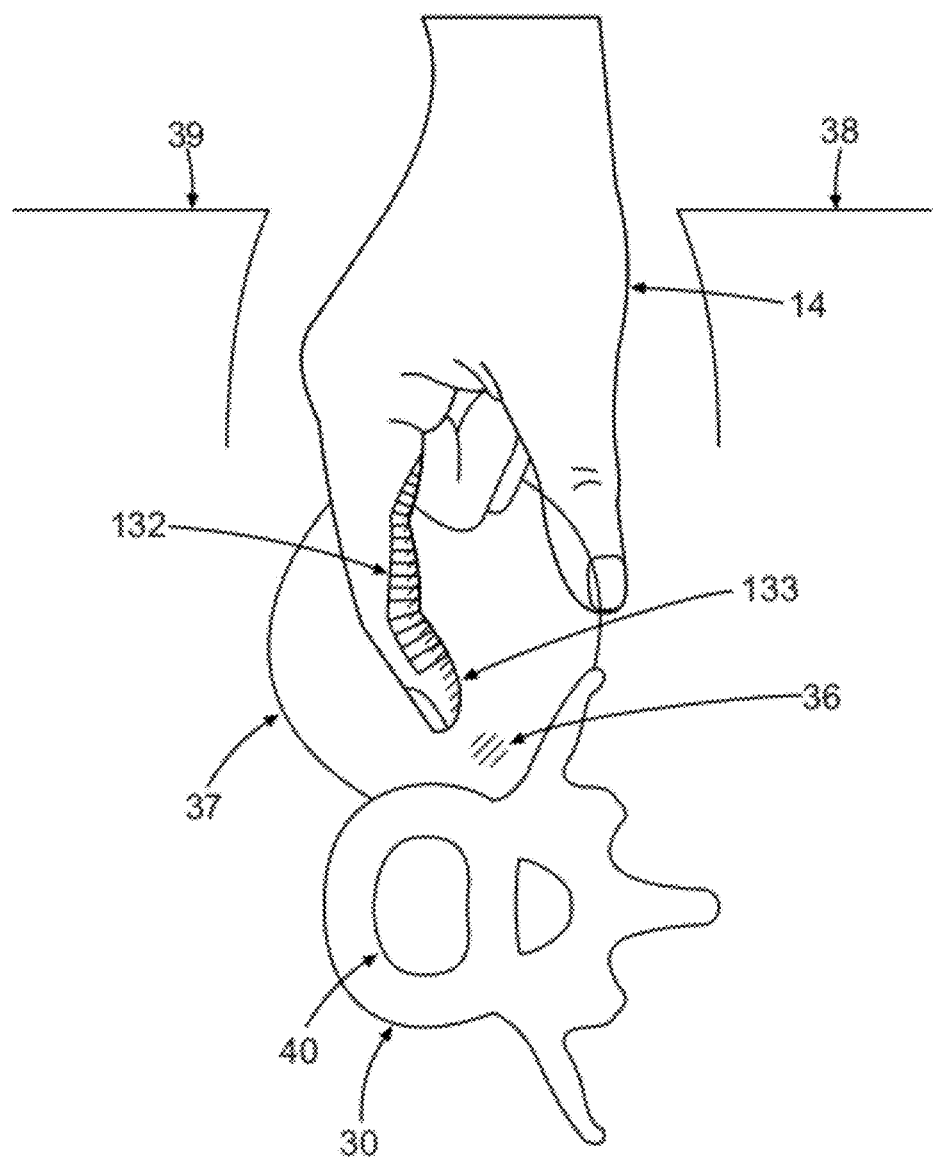
FIG. 10 is a side view showing the use of the novel surgical glove during a surgical procedure.

In FIG. 10, the electrifiable surgical glove 14 is used to determine the relative proximity and location of a nervous system component 36 by palpating the soft tissues 37 surrounding the vertebrae 30. The glove is inserted through an incision 39 on the skin 38 of the patient. The electrical stimulation current is sent from the stimulating electrical conductive open contact surface 133, usually located on the tip of the finger into the patient's body. The stimulation current flows through the tissues to the reference electrode placed in the near proximity of the surgical site. The amplitude of the current sent is set sufficiently high in order to reach and depolarize the nerves running into the stimulated tissues and potentials will be evoked in the related muscles. EMG signals will be recorded on the neuromonitoring system via electrodes placed on or in the patient's muscles. In a typical method of nerve locating, the stimulation current is then lower and more palpating is done towards the identified nerve until evoked potentials in the muscles are recorded again. This loop may be repeated several times until the stimulation current is down to an amplitude where the nerve depolarizes only when the stimulating finger is in contact with it. Once this threshold value is found, any variation of the neuromonitoring modalities informs the IONM specialist and the surgeon on the relative proximity of the nervous system component 36. In the preferred embodiment, the variations of modalities are treated by a computer algorithm in relation with the stimulation current and direct information on relative proximity and location is displayed on the remote screen 4. Pre-defined threshold values can be set in the system and color lights are displayed on the remote screen or sounds can signal to indicate the relative proximity between the glove stimulating electrical conductive open contact surface 133 and the nervous system component.

Figure 10A:
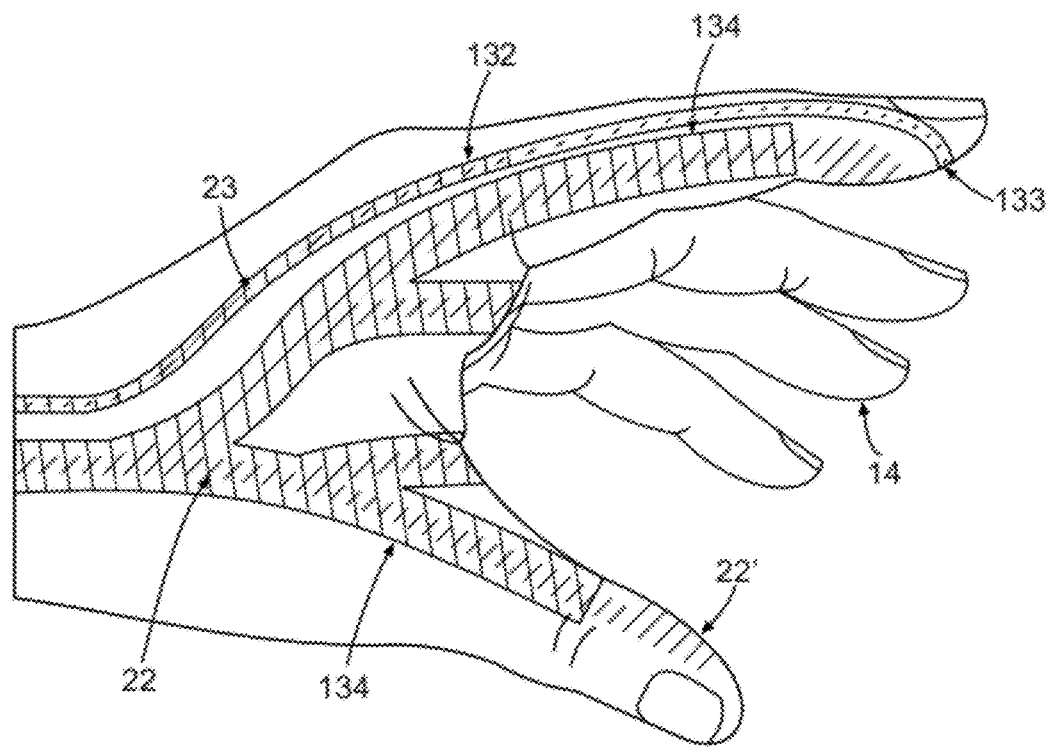
FIG. 10A is a closer view of an alternate embodiment of the surgical glove.
Figure 10B:
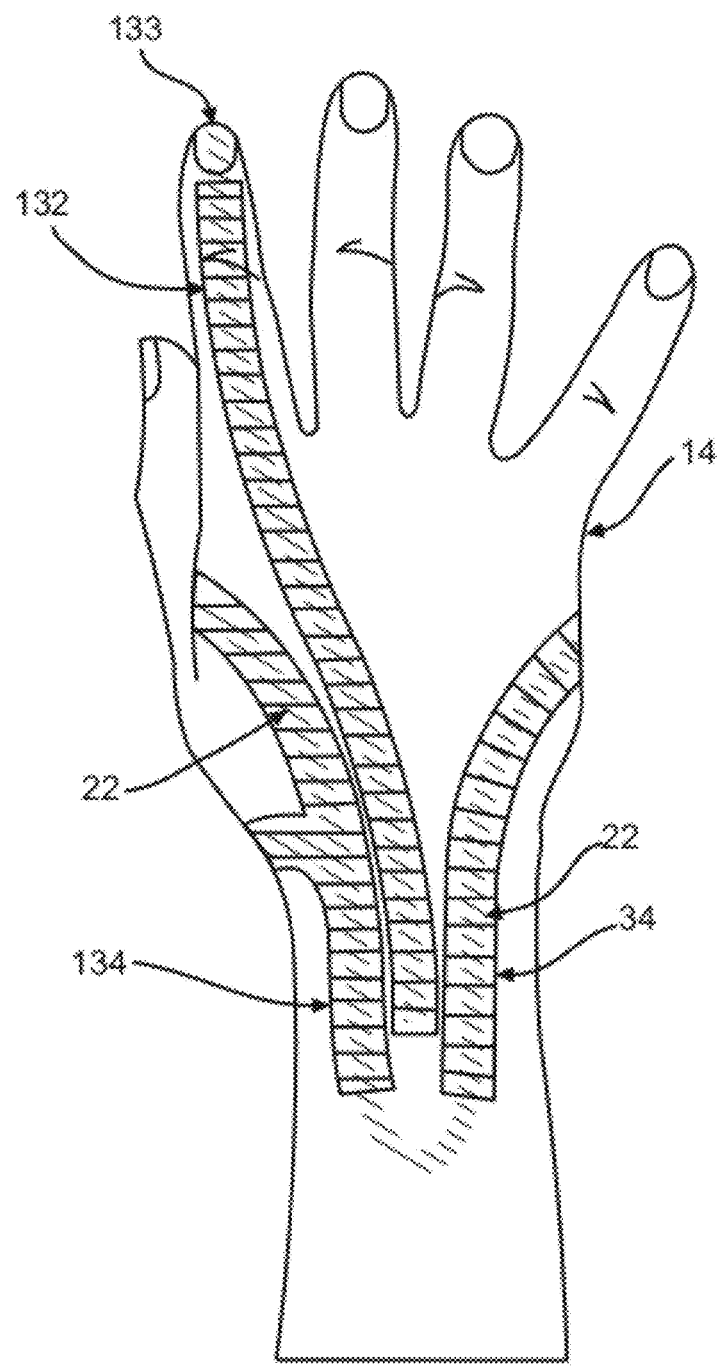
FIG. 10B is a bottom view of a hand with the electrifiable surgical glove of an alternate embodiment.
Figure 10C:
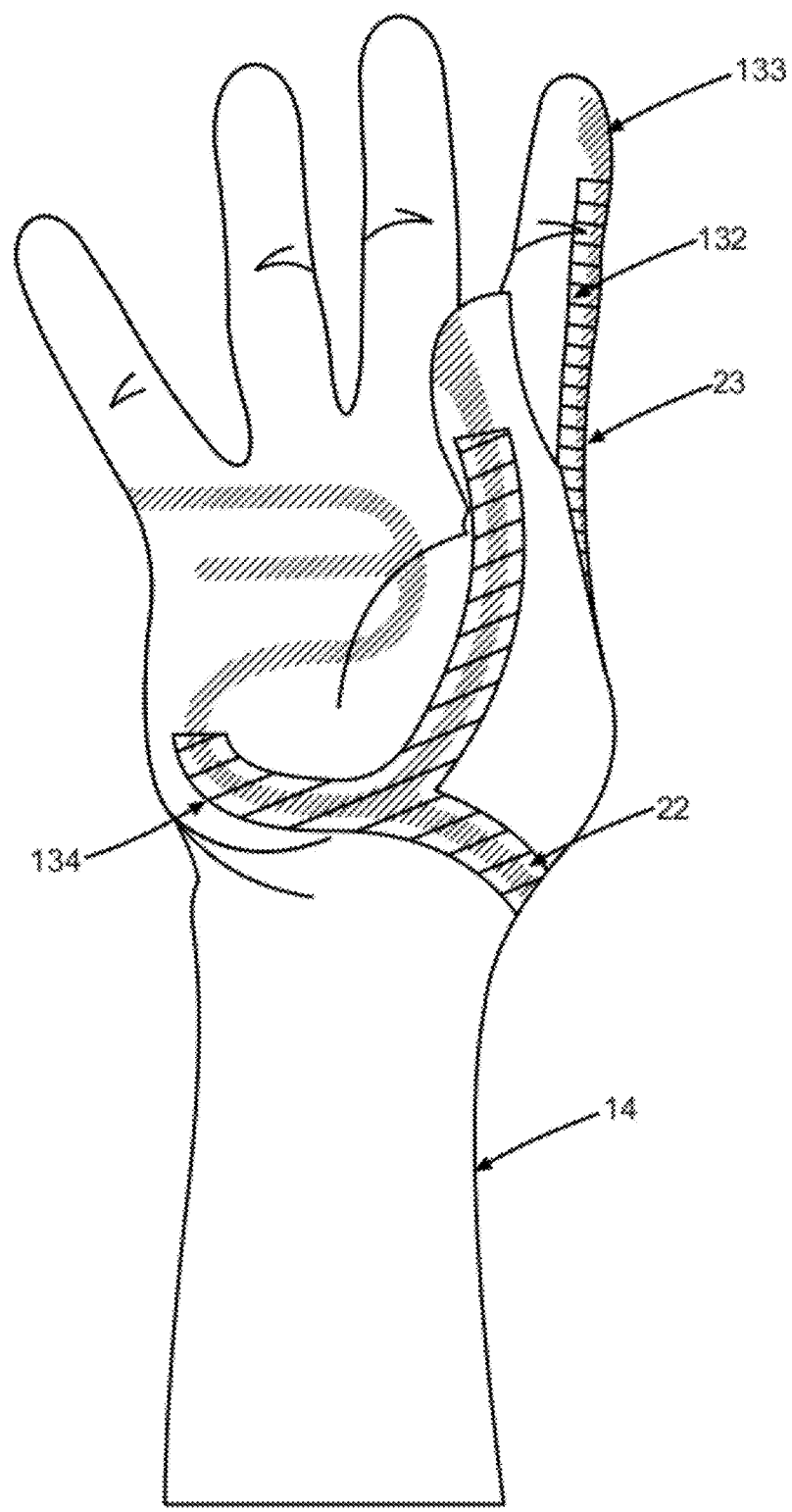
FIG. 10C is a top view of a hand with the electrifiable surgical glove of an alternate embodiment.

FIG. 10A shows a different embodiment of the electrifiable surgical glove 14 that is used to perform the palpating of the soft tissues. The electrifiable surgical glove has two electrical paths. The first path is the electrical conductive open contact surface 23 that is over-coated with an isolated electrical path 132 to only leave a small spot electrically open 133. The stimulation patch 133 is used to concentrate the electrical stimulation to a small area in order to focus this stimulation be able to determine the proximity of this patch to a nervous system component. The second path is the conductive open surface contact 22 described above that is used to connect the electrical stimulation to a surgical instrument. In a still different embodiment, those two paths can be used to perform a bipolar stimulation. In this mode, the electrical stimulation current flows from the stimulation electrical path 133 through the patient's body and then back to the second electrical conductive open surface 22. The electrical conductive open surface 22 acts as the reference electrode instead of the reference electrode 12 previously placed on the patient which would be disabled in this configuration. FIGS. 10B and 10C show the glove electrical conductive open contact surfaces 22 going from the palm side of the hand towards the back of the hand passing along both side of the hand and joining back together on the glove's cuff. This ensures electrical redundancy if one of the two paths along the side of the hand becomes not conductive due to abnormal wear. In a preferred embodiment and as shown in the figures, protective electrical insulating over-coating 134 covers areas of the glove that will not be in contact with instruments. This protective electrical insulating over-coating may be transparent, but still in a preferred embodiment, color pigments of the same color as the glove material are used in order to hide the electrical non-conductive surfaces. This color differentiation between the conductive surface and the insulated surface gives intuitive indication to the surgeon where and how to hold instruments in order to insure electrical connection. Glove electrical conductive open contact surface 23 can also run over the top surface of the index or be on the side of the index. A protective electrically insulating over-coating 132 covers most of the conductive path to only leave an electrical conductive open surface 133 of a few square millimeters at the tip of the finger. The small size of the open conductive spot is very important for getting accurate results on nerve location and nerve health assessment. To large of a spot would disperse the stimulation current into larger areas of tissue and body fluids and stimulation current threshold that was previously set for depolarizing a nerve from a certain distance would be affected and therefore wrong indication of safety would be given to the IONM specialist and surgeon. Still referring to the same figures, both electrical conductive open contact surfaces end on the top side of the hand in a location that does not bother or limit the surgeon's wrist movements. Electrical sleeve connections not shown on these figures are fixed on the ends of the electrical conductive open contact surfaces as described in the FIGS. 3, 4 and 5. It is understood that the electrical conductive open surface pattern and placement, the protective insulating over-coating pattern and placement could vary from what is shown on the figures and the electrical sleeve connection could be positioned anywhere around the glove's cuff.

In the electrifiable surgical glove embodiments shown in FIGS. 6B, 8, 10A, 10B, 10C, the physical aspect of the glove electrical conductive open contact surfaces 22, 23, 28, 133 and the electrical insulating over-coating 132 and 134 is a novelty of this invention. In all embodiments, the tactile feeling of the novel electrifiable surgical glove does not modify the actual surgical gloves tactile feeling. As described in the prior art, a natural rubber surgical glove is usually made by dipping a ceramic former into a coagulant bath. This coagulant bath is generally obtained by mixing water with calcium nitrate, calcium carbonate and some dispersants and thickeners. The calcium nitrate is used to initiate the coagulation process of the latex and the calcium carbonate is acting as a mold release. Once dried, the former is dipped into the latex compound, which is the base material of the glove. This compound is usually a water-based rubber like natural rubber. Other glove materials like nitrile, polyisoprene, polychloroprene (also known under DuPont's trade name Neoprene) or vinyl are manufactured with similar concepts. The dipping process may be repeated several times in order to build up the appropriate thickness. At this stage, the layer being on the ceramic former is called gel latex. Then, multiple dipping in different baths are made for leaching, cleaning and eventually coating the glove. A final curing process at an elevated temperature occurs in order to give to the rubber its final mechanical properties. The thickness of a surgical glove is usually between 8 and 15 mils (thousandth of an inch) depending on the material used and the level of robustness is wanted. This range of thickness along with the elasticity of the material is important in order to give a maximal tactile sensitivity to the surgeon without compromising the efficiency of the protective barrier and the mechanical properties of the glove. Thicker gloves similar to those used in commercial applications would highly reduce the tactile feeling and therefore compromise the dexterity of the surgeon. One of the key aspects of the present invention is to not affect the tactile sensitivity of the glove when creating the electrical conductive pathways. Most surgeons wear two pairs of gloves to increase the protection barrier and reduce the risk of contamination if the outer glove is cut. Since all human hands are different, surgical glove are sized but even being sized, the materials (latex, nitrile, polyisoprene, polychloroprene or vinyl) need to be stretchable in order to be able to insert the hand in the glove and also, to get a tight fit between the hand and the glove, which gives the tactile feeling that is critical for any surgeries. Therefore, any addition to the surgical glove material needs to be stretchable and have similar mechanical properties like strength, elongation and resilience. In order to keep similar properties, different materials, processes and layers combinations can be used. Moreover, a wide range of conductive materials can be used to conduct electricity. Any conductive biocompatible material can be used, like metals, polymers, carbon particles or carbon nanotubes. The two main embodiments that will be described below are either integrating the conductive layer into the glove during its manufacturing process or integrating the conductive layer over the glove once the glove has been completely cured.

In one embodiment of the present invention, integrating the conductive layer during the glove manufacturing process can be made of two different ways: creating a glove material that is intrinsically conductive or adding a conductive layer within the glove. To create a glove material that is intrinsically conductive, conductive filler has to be integrated into the glove material compound. As mentioned previously, the conductivity of the glove needs to be below 2000 Ohms, so the quantity of conductive filler needs to be relatively important. The challenge is that by adding a certain quantity of filler, the glove material loses its mechanical properties. Therefore, only a few fillers can fulfill this function. Fillers like polyaniline (PANI) are polymers that are intrinsically conductive and by nature, have some elastic properties that can be similar to a surgical glove. So, the right conductive filler can be added to the glove material compound and the ceramic former is then dipped into the compound to create the fully conductive glove. Then, the glove material without filler can be put over the first layer by ways of airbrushing, spraying, dispensing or partial over-dipping in order to insulate the appropriate locations of the glove. Another option is to incorporate the conductive layer as an initial step of the manufacturing process of the surgical glove. Conductive coating can be pre-deposited on the hand former used to manufacture surgical glove prior to over dip it into the glove material. A short drying period may be observed between the dips in order to not contaminate the second compound. By doing so, the conductive coating bonds to the glove material during the final curing process and creates a strong adherence. In a third option, the conductive layer can be added on the glove material, after the initial dipping in the base non-conductive material, when it's still in a gel state. After a short period of drying but still during the gel phase, the conductive layer is added to the gel glove. This conductive layer is a compound made of a polymer, a conductive filler, and other additives like dispersant, rheology modifier, surfactant, defoamers and the like. The conductive layer can be added in many ways like over-dipping, spraying, airbrushing, dispensing. Then, using the glove material or a polymer, the isolative layer is added over the appropriate areas. This isolative layer can also be sprayed, dispensed, airbrushed, partially over-dipped or other means of adding material on selective areas.

In another embodiment, the conductive material is put on the surgical glove after it has been cured. The prior art mentions the potential to coat gloves using vapor deposition processes. We have found that the electrical connection done using these processes only work in an un-stretched state. Once a glove is coated with a physical vapor deposition (PVD) process, the coated particles form miniature islands when stretched and continuous electrical contact is not possible. Therefore when using vapor deposition, we suggest the following process: forming a surgical glove from a base material, expand the surgical glove to a maximum usable size, hold the glove in the expanded state, coat the glove with a second conductive material using vapor deposition process or any other coating process, allow the glove to cure if necessary which depends on the material used to coat, release the glove, sterilize and package.

In a preferred embodiment, both conductive material and isolative layers are coated on the finished surgical glove, after it has been cured. These coatings need to be well bonded and integrated on the surface of the base rubber glove in order to resist to abrasion and contact to fluids and blood that occurs during surgeries. It has been experimented that most of the materials having a good primarily bonding on rubber gloves have tendency to easily delaminate after a stretch of the base rubber. This is mostly due to a difference in the mechanical properties such as elongation, modulus of elasticity and resilience of the rubber and the coatings. In instance, when stretching the base rubber, if the coating deforms differently, a shear stress occurs between the two materials and breaks the bond between the two layers. Therefore, it is important that all the coatings used, electrically conductive or not, have the ability of following the deformations of the base rubber glove without affecting it. As a requirement, the ultimate elongation required by the standards for synthetic rubber surgical gloves is 650% before aging. It has been experimented that a surgical glove during the donning process can be stretched up to 300%. In order to fit tightly on the surgeon's hands and insure a good tactile feeling, it has also been experimented that a glove could be stretched up to 50% when worn. Talking more particularly about the electrically conductive layer, these two values mean that the electrically conductive coating needs to still be conductive after a stretch of 300% and has to still be electrically conductive when stretched 50%. The conductive coating is made out of a carrier, which is a resin in the families of acrylic, styrene, urethane, silicone, vinyl, chloroprene or the like, a conductive filler such as metals, carbon black, intrinsically conductive polymer, carbon nanotubes and different additives like a dispersant helping the dispersion of the conductive particles into the resin, rheology modifier, surfactants, etc. Many experiments have been done with many different combinations of products and it has been figured out that one of the most efficient conductive filler tested was the silver flakes. Silver is often use in the medical field for its antimicrobial properties and does not present any biocompatibility issue. The flat, rough and irregular geometry of the silver flakes allows them to interlace with each other and forms long and more robust electrically conductive chains, even when stretched. This particular geometry also gives them good grip when mixed and dried into elastomeric materials. The average size of the flakes plays an important role in the electrical conductivity and optimal results were obtained with average flakes size between 5 and 15 microns. In order to keep acceptable mechanical properties of the conductive coating, the lowest concentration of filler is wanted. This can be achieved by measuring the electrical resistivity of the material at different concentration of filler and reporting the data on a graph. The resulting graph is called the percolation curve. Another series of experiments have been made by measuring the tensile strength of the conductive coating at different concentration of filler and reporting the data on a graph. Both percolation curve and tensile strength curve were used to determine that the optimal concentration of filler giving an electrical resistivity below 2000 Ohms after 300% of stretch, remains conductive at 50% of stretch and has an ultimate tensile strength up to 650% was between 30 and 60%, depending on which resin was used. The second important element for obtaining those performances is the choice of the resin. All electrically conductive coatings become non-conductive over a certain amount of stretch. When released after stretching, the coating takes time to recover and regain its conductivity. During this recovery process, the broken islands of silver flakes created during the stretch move inside the resin to slowly recreate a uniform conductive film. Since the conductive coating is bonded on or integrated in between different layers of rubber and polymer, the resilience of the different materials may affect the recovery of the conductive coating. If the conductive coating is forced to recover too quickly, the disposition of the flakes changes and the electrical conductivity may be lost. If plastic deformation in one of the materials surrounding the conductive layer or a plastic deformation of the resin occurs, electrical conductivity may be lost too. Optimum electrically conductive properties during stretching are obtained when the molecules of the resin holding a silver flake are elastic enough to follow the deformation of the substrate without breaking apart while staying bonded to it. Resins in the styrene family have given the best results and met the requirements previously described. The third important element for obtaining good electrically conductive coatings is the dispersion of the conductive filler into the resin. Depending on the shape of the filler particles, in instance if the filler is flakes, the surface tension in the resin forces the flakes to stay on the surface. A dispersant agent comprising surfactants is necessary in order to modify the surface tension and improve the dispersion, the separation and the wetting rate of the silver particles when mixed into the resins. Viscosity and pH of the solution need to be precisely controlled in order to obtained good and constant electrical properties. A good and homogenous dispersion of the conductive filler into the resin improves the electrical conductivity of the compound for a given concentration of filler. Since the lowest concentration of conductive filler is wanted in order to obtain the best mechanical properties of the coating and to not affect too much its bonding property with the base rubber glove, the use of a dispersant agent is necessary in the compounding of a stretchable electrically conductive coating. Since metallic fillers have a volumetric mass higher than the resins, the metallic particles once dispersed have tendency to settle down. Active stirring of the compound is important before and during the coating process. Quick drying of the coating also avoids the conductive particles to settle down once applied on the base rubber glove. The thickness of the conductive coating plays also a key role in the electrical and mechanical performances of the layer. A thick layer gives a more robust and more conductive coating. Moreover, a thin layer is desirable in order to not affect the tactile feeling of the surgeon. Conductive layers having a thickness between 1 and 3 mils (thousandth of an inch) have given the best compromise between mechanical and electrical properties and met the requirements previously described. It has been demonstrated that even with good bonding properties, the electrically conductive coating might present a risk of delaminating off the base glove or wearing out too quickly under aggressive abrasions. It is well known that surgical gloves are exposed to aggressive abrasion when the surgeon uses certain instruments or touches sharp bones. Therefore, a protective coating being thin enough to conduct the electricity through it but strong enough and adhering well to the base glove material has been developed and over-coated on the conductive coating. As discussed before, this protective coating must have similar mechanical properties than the glove material and the conductive coating. Polymers in the urethane family have given the best results but may be selected in the families of acrylic, styrene, silicone, vinyl, chloroprene or the like. The protective coating has a thickness under 1 mil in order to not affect the tactile feeling of the surgeon and still be electrically conductive through it. Finally, as already described in different embodiments of the present invention, an electrically non-conductive coating is needed to partially cover and insolate the electrically open conductive path made on the glove. Color pigments may be mixed in the isolative coating in order to differentiate electrically conductive and electrically non-conductive areas of the glove. Best results have been obtained by using the same polymer than the protective coating with a higher concentration of solids and by making a layer thickness between 1 and 3 mils. Other polymers may be used, selected in the same families than those mentioned previously. The protective layer can be applied on the conductive coating only in the areas that are not insulated. Depending on the manufacturing process used, it could be easier to apply the protective coating over the complete electrically conductive layer and then partially insulate the appropriate areas over the first two layers. An interesting aspect that relates to bonding has been discovered during the multiple experimentations. The electrically conductive layer could be made using both water-based and solvent-based resins and similar electrical and mechanical performances are obtained. Moreover, it has been demonstrated that the best adherence results with the base glove material were obtained with the solvent-based resins. The presence of solvent slightly bites into the base glove material, improves the dispersion of the conductive filler and shortens the drying time of the compound avoiding the conductive particles settling down and therefore improves the bonding properties. Complete drying of the first layer was performed before applying the over-coating. Protective and isolative layers could also be made using both water-based and solvent-based polymers. Moreover, it has been tested that a solvent-based polymer, when coated over the first electrically conductive layer, has tendency to re-disperse its silver particles and therefore modify the electrical properties of the conductive layer. This is produced by the solvent being in the second layer partially re-dissolving the initial layer and the surface tension forces the silver flakes to migrate on the surface. Further, experimentations have been done using a first electrically conductive layer having a water-based resin with an over-coating of solvent-based polymer. In this case, the over-coating has tendency of delaminating the first layer from the base glove material. Finally, the best results were obtained by using solvent-based resins for the electrically conductive layer and a water-based polymer for the protective and isolative layers. The solvents are selected for their ability to dissolve the resins used, their efficiency for biting into the base glove material without weakening it too much and finally for controlling the evaporation and drying rates of the coating in function of the manufacturing process for applying the coating. Best results were obtained with a blend of toluene, methyl-ethyl-ketone and heptanes. The electrically conductive coating and the protective and insolating coatings can be applied on the glove by different manufacturing processes like spraying or airbrushing, paint brushing, sponge brushing, dispensing, etc. Continuous stirring of the conductive coating is important to keep the filler particles dispersed in solution. Drying the coating after each layer is also important to obtain good bonding properties. In this preferred embodiment, the conductive coating, the protective coating and finally the isolative coating are applied on a cured surgical glove. In a different embodiment, the glove is stretched during the application of at least one coating. This improves the electrical conductivity properties when the glove is stretched beyond the limits previously discussed.

Figure 11:
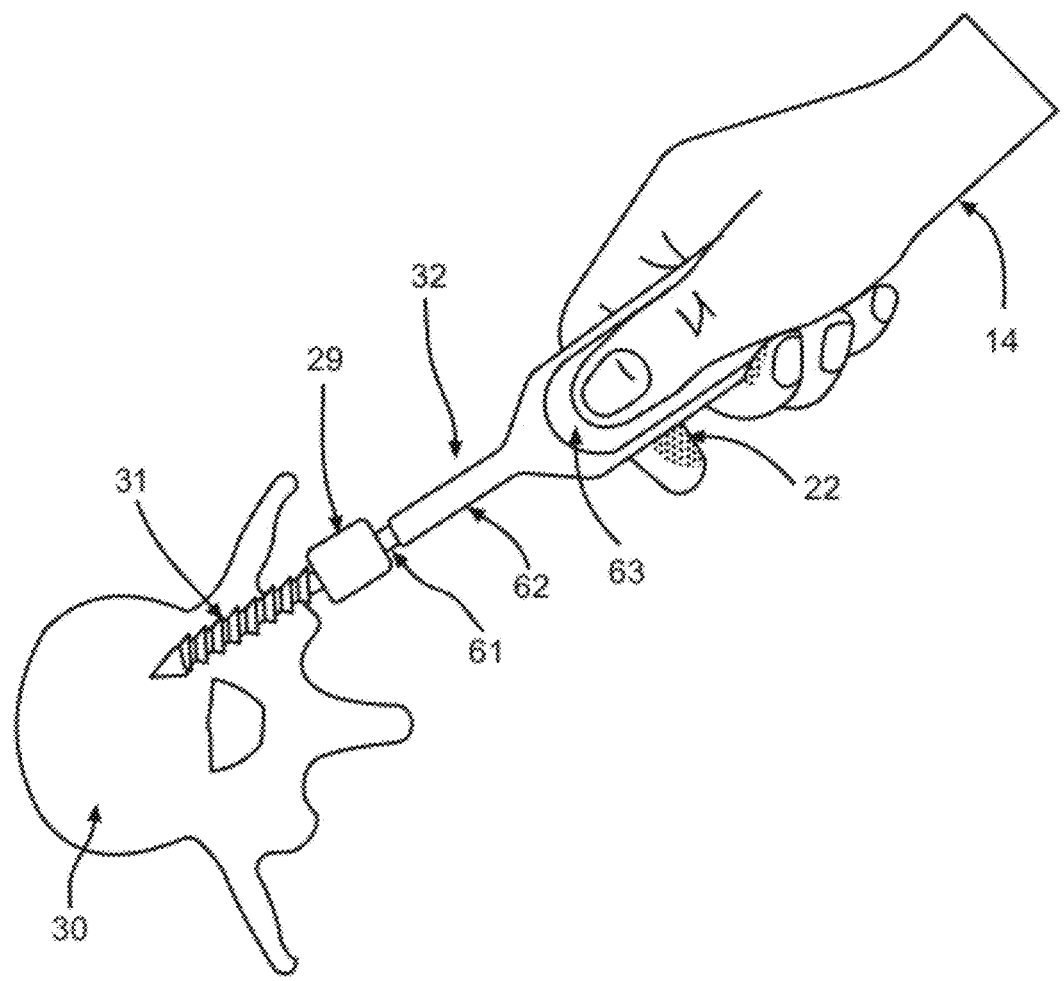
FIG. 11 is an isometric view showing the use of the novel surgical glove during a surgical procedure.

In FIG. 11, the electrifiable surgical glove 14 holds an electrically conductive wireless screwdriver 32 to thread a pedicle screw 29 into the pedicle canal 31 of a vertebra 30. By having a screwdriver that connects to the glove, a stimulation current flows from the glove electrical conductive open contact surface 22, through the screwdriver electrical contact 63, to the isolated portion of the screwdriver 62, to the end effector 61, to the pedicle screw 29, to the vertebrae 30 and finally to the reference electrode 12. The readings from the neuromonitoring modalities can determine in a real time manner when screwing the screw if there is a breach in the pedicle canal of the vertebrae. It is understood that the screwdriver handle can be a modular fixed or ratcheting handle where a screwdriver shaft is affixed into it by a quick coupling mechanism. The proximal portion of the screwdriver shaft and the distal portion of the wireless modular handle quick coupling both have electrically open conductive surfaces that are in contact when the shaft is coupled with the modular handle. Other instruments like drill bits, taps, scrappers, all having an electrically conductive end effector, an insulated core and a proximal electrically open conductive surface, may be connected to the modular quick coupling handle and electrically stimulated when the surgical glove holds the handle.

Figure 12:
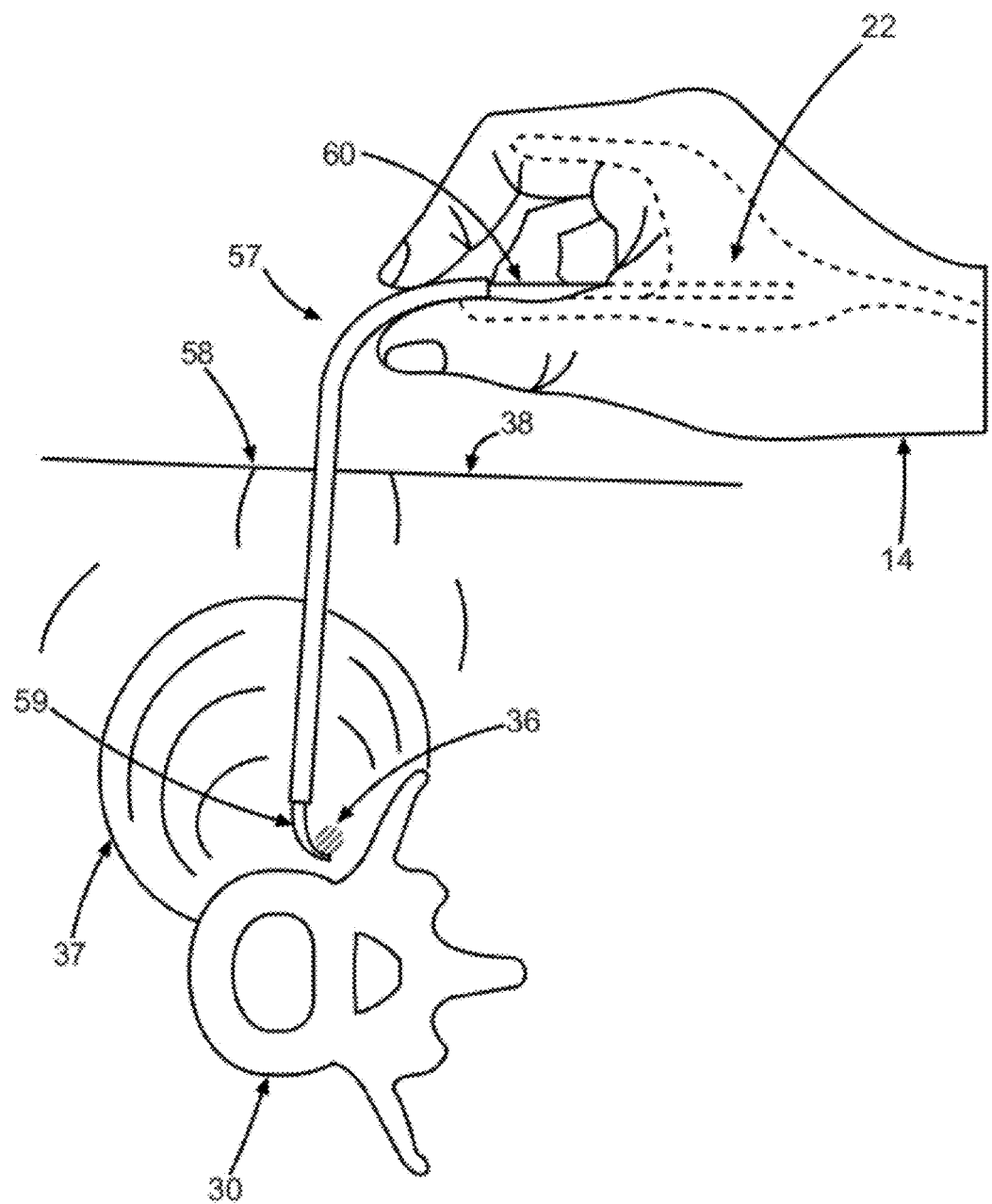
FIG. 12 is a side view of the electrifiable surgical glove holding an electrifiable wireless retractor to protect a nerve near the vertebrae.

In FIG. 12, the electrifiable surgical glove 14 holds an electrically conductive wireless surgical retractor 57 that is used to determine the relative proximity and location of a nervous system component 36 and then to retract and protect this nervous system component. By being placed just next to this nervous system component, the retractor avoids any other instruments from coming into contact with it. The retractor is inserted through an incision 39 in the skin 38 of the patient and then through the soft-tissues 37 surrounding the vertebrae 30. A stimulating current flows from the glove electrical conductive open contact surface 22, to the retractor electrical contact 60, to the isolated portion of the retractor 58, to the end effector 59 and finally into the nervous system component 36. An electrical stimulation current sent from the retractor into the patient's body, affects the readings of the neuromonitoring modalities. The variation of those modalities informs the IONM specialist on the relative proximity and health status of the nervous system component 36. In another preferred embodiment, the variations of modalities are treated by a computer algorithm in relation with the stimulation current and direct information on relative proximity, location and health status is displayed on the remote screen 4. Pre-defined threshold values can be set in the system and color lights are displayed on the remote screen or sounds can signal to indicate the relative proximity between the retractor end effector 59 and the nervous system component.

Figure 13:
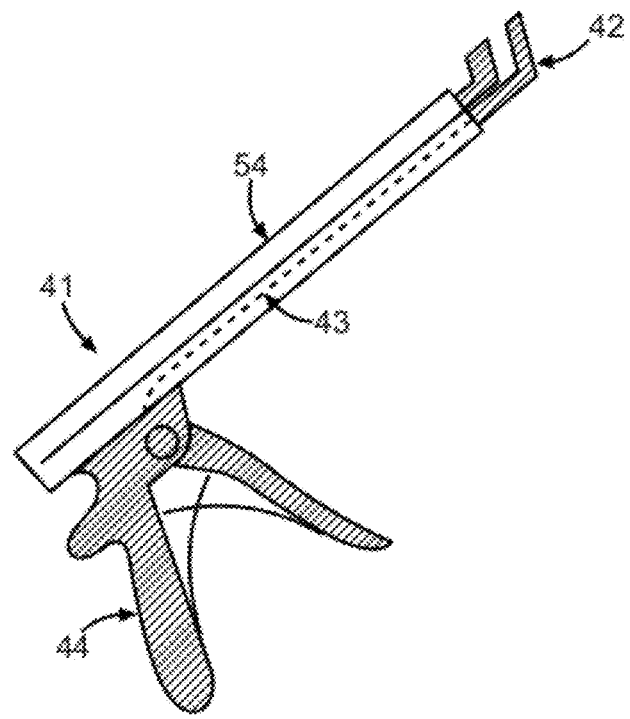
FIG. 13 is an isometric view of an electrifiable wireless rongeur.

In FIG. 13, an electrically conductive wireless rongeur 41 is shown. The rongeur has an electrically conductive handle 44 that is connected to the end effector 42 of the rongeur via the conductive core 43 that is isolated by the core insulator 54. In the preferred embodiment, the conductive core 43 is the structural elongated portion of the rongeur and this portion is coated with a core insulator 54. The end effector 42 of the rongeur is used to send a stimulation current into the patient's body and the readings of the neuromonitoring modalities inform the IONM specialist on the relative proximity of this rongeur to a nervous system component. In another embodiment, the structural elongated portion of the rongeur is the core insulator 54 in which a conductive core 43 is inserted.

Figure 14:
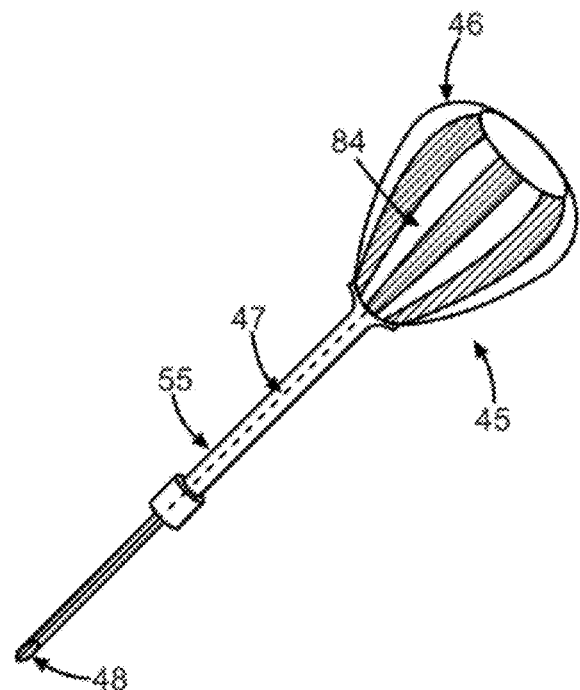
FIG. 14 is an isometric view of an electrifiable wireless awl.

In FIG. 14, an electrically conductive wireless awl 45 is shown. In the preferred embodiment, the awl has a handle where electrically conductive sections 46 are alternated with gripping sections 84. The electrically conductive sections are connected to the end effector 48 of the awl via the conductive core 47 that is isolated by the core insulator 55. The conductive core 47 is the structural elongated portion of the awl and this portion is coated with a core insulator 55. The end effector 48 of the awl is used to send a stimulation current into the patient's body and the readings of the neuromonitoring modalities inform the IONM specialist on the relative proximity of this awl to a nervous system component. In another embodiment, the structural elongated portion of the awl is the core insulator 55 in which a conductive core 47 is inserted. In a different embodiment, the handle has only one electrically conductive zone.

All the handles of the surgical instruments described in the present invention can be made out of a non-conductive material like silicone or TPE loaded with an electrically conductive material. Silicone handles are particularly well appreciated by the surgeons for its comfortable tactile touch, its anti-slippery properties when hold with bloody gloves and its good resistance to high temperatures during autoclave sterilization. Electrically conductive handles are well known and have been made and used for a long time. Electrically conductive materials like silicone or TPE are very often used for electrostatic discharge protection (ESD) in the handles of multiple tools principally used for electronic circuit boards manipulation. However, those ESD materials are not suitable for use in the context of the present invention since their electrical resistivity is usually above 10 Kilo Ohms and would attenuate the stimulation current generated by the neuromonitoring system. The electrical resistivity of the surgical handles needs to be below 1000 Ohms in order to not affect the stimulation signal. These electrical conductivity properties can be obtained by loading the silicone or TPE with either metallic or non-metallic electrically conductive filler. Silver coated glass flakes, silver flakes, silver particles, stainless steel flakes or any other kind of metallic flakes or particles is suitable for making a conductive silicone or TPE. Carbon black is used as non-metallic filler. In order to keep acceptable mechanical properties of the conductive material, the lowest concentration of filler is wanted. This can be achieved by measuring electrical resistivity of the material at different concentration of filler and reporting the data on a graph. The resulting graph is called the percolation curve. Another series of experiments have been made by measuring the tensile strength of the conductive silicone at different concentration of filler and reporting the data on a graph. Both percolation curve and tensile strength curve are used to determine the optimal concentration of filler that gives good electrical resistivity and good mechanical properties. The best results were obtained by mixing silver flakes into silicone at a concentration between 25 and 45%. In a different embodiment, a physical vapor deposition (PVD) process can be use to coat a layer of electrically conductive material over a non-conductive handle. In still a different embodiment, a thin and flexible electrically conductive sock may be put on a non-conductive handle. The distal portion of the sock electrically contacts the distal end of the handle core in order to conduct the current into the instrument. This electrically conductive sock may be single use and disposed after use. This allows minimal modification of existing instrumentation in order to be used within the present invention.

Figure 15:
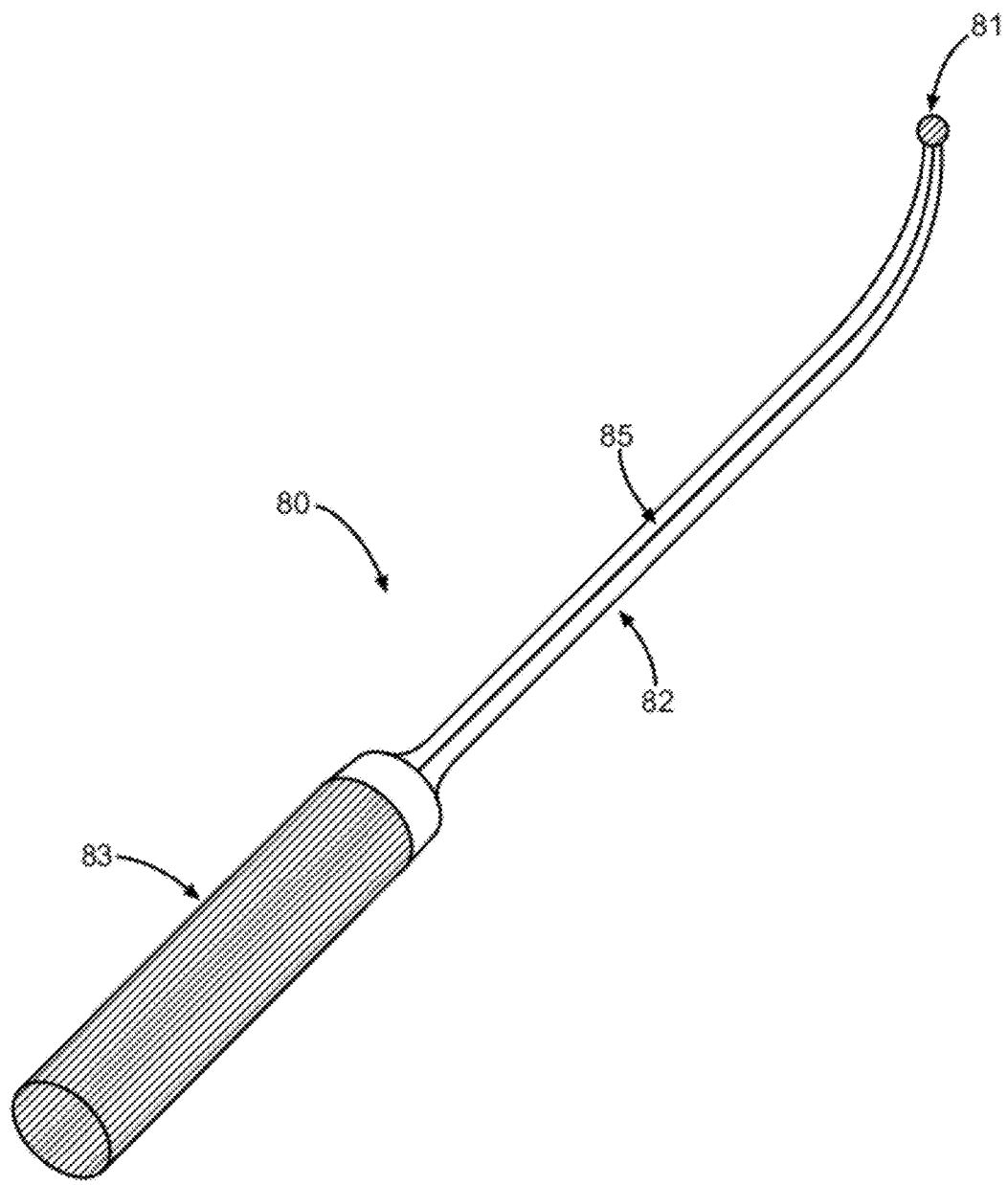
FIG. 15 is an isometric view of an electrifiable wireless surgical probe.

In FIG. 15, an electrically conductive wireless surgical probe 80 is shown. The probe has an electrically conductive handle 83 that is connected to the end effector 81 of the probe via the conductive core 85 that is isolated by the core insulator 82. In the preferred embodiment, the conductive core 85 is the structural elongated portion of the probe and this portion is coated with a core insulator 82. The end effector 81 of the probe is used to send a stimulation current into the patient's body and the readings of the neuromonitoring modalities inform the IONM specialist on the relative proximity of this probe to a nervous system component. In another embodiment, the structural elongated portion of the probe is the core insulator 82 in which a conductive core 85 is inserted.

Figure 16:
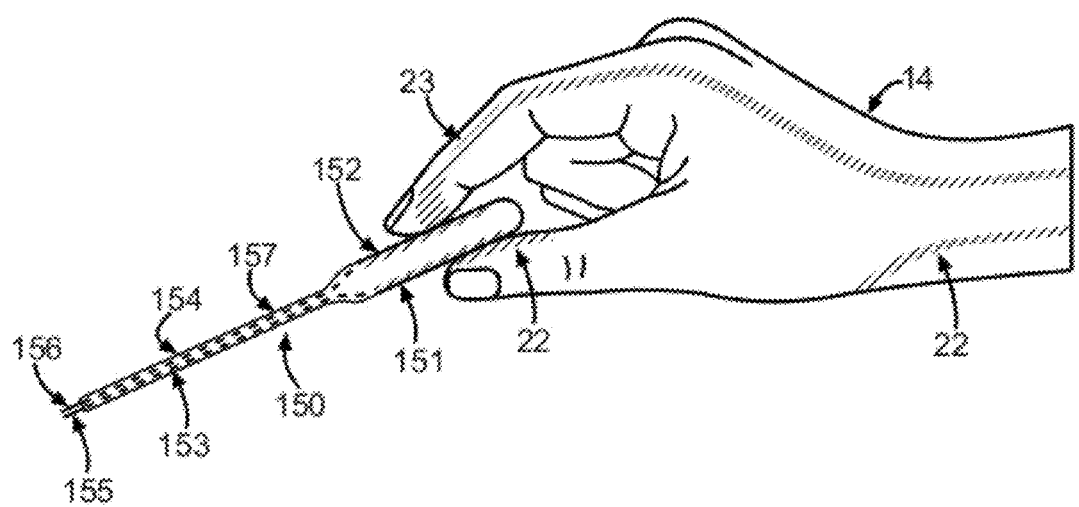
FIG. 16 is an isometric view of an electrifiable wireless bipolar surgical probe.

In FIG. 16, the electrifiable surgical glove 14 holds a bipolar electrically conductive wireless stimulation probe 150 that is used to locally stimulate tissues. As an example, the bipolar stimulation probe is very popular in brain surgery when removing a tumor. The bipolar probe allows the surgeon to locally stimulate small areas and distinguish the healthy tissues to the unhealthy tissue in order to remove it.

The stimulating current flows from the glove electrical conductive open contact surface 22, to the first probe electrical contact 151, to the first isolated conductor 153, to the end effector 155 and finally into the tissue. To close the electrical circuit, the second end effector 156 acts as the reference electrode. Unlike the previous cases where a monopolar stimulator was used, the current flows back to the second end effector 156, to the second isolated conductor 154, to the second probe electrical contact 152, to the second glove electrical conductive open contact surface 23 and then back to the main connection box 6 and neuromonitoring computer system 1. In this situation, the reference electrode 12 is deactivated. Not shown in the figure, an electrical insulating over-coating may partially cover the electrical open conductive surfaces 22 and 23 to limit the conductive areas. The local stimulation current affects the readings of the neuromonitoring modalities. The variation of those modalities informs the IONM specialist on the health of the tissue probed. In the preferred embodiment, the variations of modalities are treated by a computer algorithm in relation with the stimulation current and direct information on the health status is displayed on the remote screen 4. Pre-defined threshold values can be set in the system and color lights are displayed on the remote screen and on the electronic module 127. Sounds can also give information on the health of the tissue area probed. In a different application, the stimulations transmitted by the bipolar probe can produce twitches in tissues where nervous structure is present. Instead of the neuromonitoring equipment previously described in the present invention, a small portable battery operated single-use or reusable stimulator may be used in this case and directly located on the glove cuff or on the gown cuff. Frequently used during dissection, the surgeon knows which tissues can be cut without damaging nervous elements. It is understood that the bipolar wireless probe is used as an example only, without the intention of limiting the present invention. Any other instruments like bipolar scissors, bipolar forceps, bipolar knives, bipolar clamps, bipolar tweezers or the like having two end effectors and where the stimulation current flows from the first electrically conductive open contact surface of the glove to the first electrical contact on the instrument, to the first isolated conductor, to the first end effector, into the patient's body and then back to the second end effector, to the second isolated conductor, to the second electrical contact on the instrument and finally to the second electrically conductive open contact surface of the glove may be used without departing from the scope of the invention.

Figure 17:
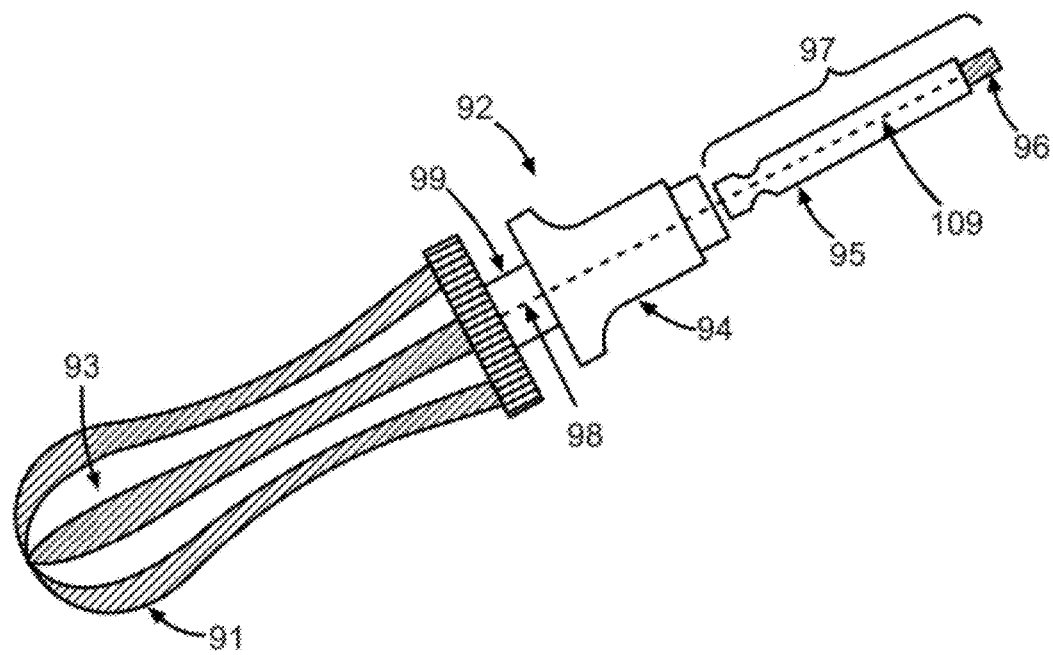
FIG. 17 is an isometric view of an electrifiable wireless screw driver handle.

In FIG. 17, an electrically conductive wireless ratcheting handle 92 with quick coupling 94 mounted with a screwdriver shaft 97 is shown. In the preferred embodiment, the ratchet mechanism is coupled to a handle where electrically conductive sections 91 are alternated with gripping sections 93. The electrically conductive sections 91 are connected to the end effector 96 of the screwdriver via the ratchet conductive core 98 that is isolated by the ratchet's core insulator 99 and the screwdriver shaft conductive core 109 that is isolated by the screwdriver shaft's core insulator 95. The ratchet's conductive core 98 and the screwdriver shaft's conductive core 95 are the structural elongated portion of those instruments and those portions are respectively coated with the ratchet's core insulator 99 and the screwdriver shaft's core insulator 95. The end effector 96 of the screwdriver shaft is used to send a stimulation current into the patient's body and the readings of the neuromonitoring modalities inform the IONM specialist on the relative proximity of this ratchet with quick-coupled screwdriver to a nervous system component. In another embodiment, the structural elongated portion of the ratchet is the core insulator 99 in which a conductive core 98 is inserted and the structural elongated portion of the screwdriver shaft is the core insulator 95 in which a conductive core 109 is inserted. In a different embodiment, the handle has only one electrically conductive zone. In a still different embodiment, the handle is made out of a conductive material. It is understood that the ratchet mechanism and the screwdriver shaft are used as examples only without the intention of limiting the present invention. Any other instruments like torque limiting handle, fixed handle or the like having a quick coupling function and any modular quick coupled shafts having a drilling, tapping, rasping function may be employed without departing from the scope of the invention.

For all of the instruments described, portions may be insulated by a variety of different methods including using isolative insulating coatings such as nylon, Teflon, silicone or all kind of dielectric coatings on certain parts of the instrument. Other materials may include anodizing or placing plastic covers over the component.

Figure 18:
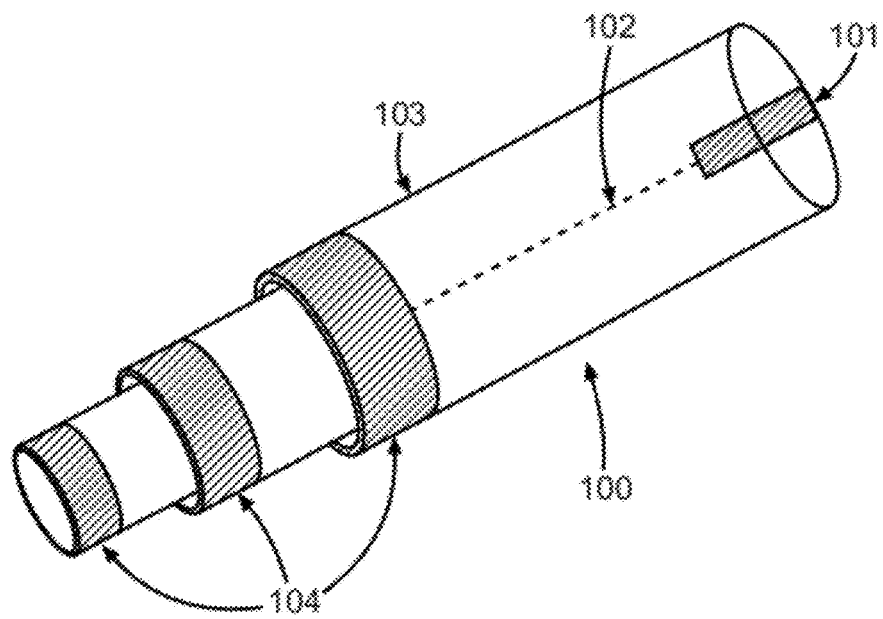
FIG. 18 is an isometric view of an assembly of electrifiable wireless cannulae retractors.

In FIG. 18, an assembly of three electrically conductive wireless cannulas 100 is shown. The cannulas have an electrically conductive holding tip 104 that are connected to the end effector 101 of the cannulas via the conductive cores 102 that are isolated by the core insulator 103. In the preferred embodiment, the conductive cores 102 are the structural elongated portion of the cannulas and are coated with a core insulator 103. The end effector 101 of the cannulas are used to send a stimulation current into the patient's body and the readings of the neuromonitoring modalities inform the IONM specialist on the relative proximity of these cannulas to a nervous system component. In order to determine the location of a nervous system component, the end effector 101 covers only a relatively small portion of the circumference of the cannula. By rotating the cannula on itself, the distance between the end effector and the nervous system component varies, as the intensity of the neuromonitoring modalities. The cannulas in the assembly are of three different diameters and can all be inserted together or one over the other in order to dilate tissues. Before placing the smallest cannula, a wireless K-wire having an electrically conductive holding tip, an electrically conductive core that is insulated and an electrically conductive end effector may be used to create the surgical access to the targeted site while avoiding the nervous structures and further guide the subsequent cannulas. In another embodiment, the structural elongated portion of the cannula is the core insulator 103 in which a conductive core 102 is inserted. In a different embodiment, the end effector 101 covers the full circumference of the cannula. In a different embodiment, the number of cannulas in the assembly can vary between one and five.

Figure 19:
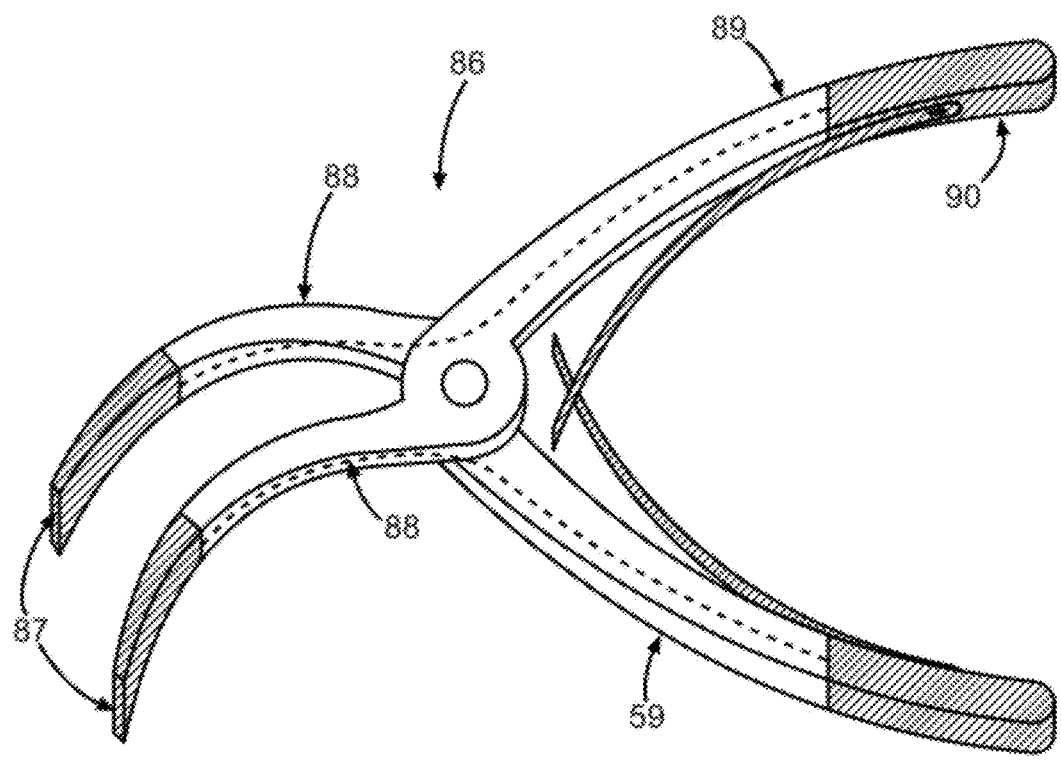
FIG. 19 is an isometric view of an electrifiable wireless distractor.

In FIG. 19, an electrically conductive wireless distractor 86 has an electrically conductive handle 90 that is connected to the end effector of the distractor 87 via the conductive core 88 that is isolated by the core insulator 89. In the preferred embodiment, the conductive core 88 is the structural elongated portion of the distractor and this portion is coated with a core insulator 89. The end effector 87 of the distractor is used to send a stimulation current into the patient's body and the readings of the neuromonitoring modalities inform the IONM specialist on the relative proximity of this distractor to a nervous system component. In another embodiment, the structural elongated portion of the distractor is the core insulator 89 in which a conductive core 88 is inserted. It is understood that the shape and design of the distractor is not limited to what is shown on the image and that any surgical instrument that is use to enlarge the access to a surgical site can be known as a distractor.

Figure 20:
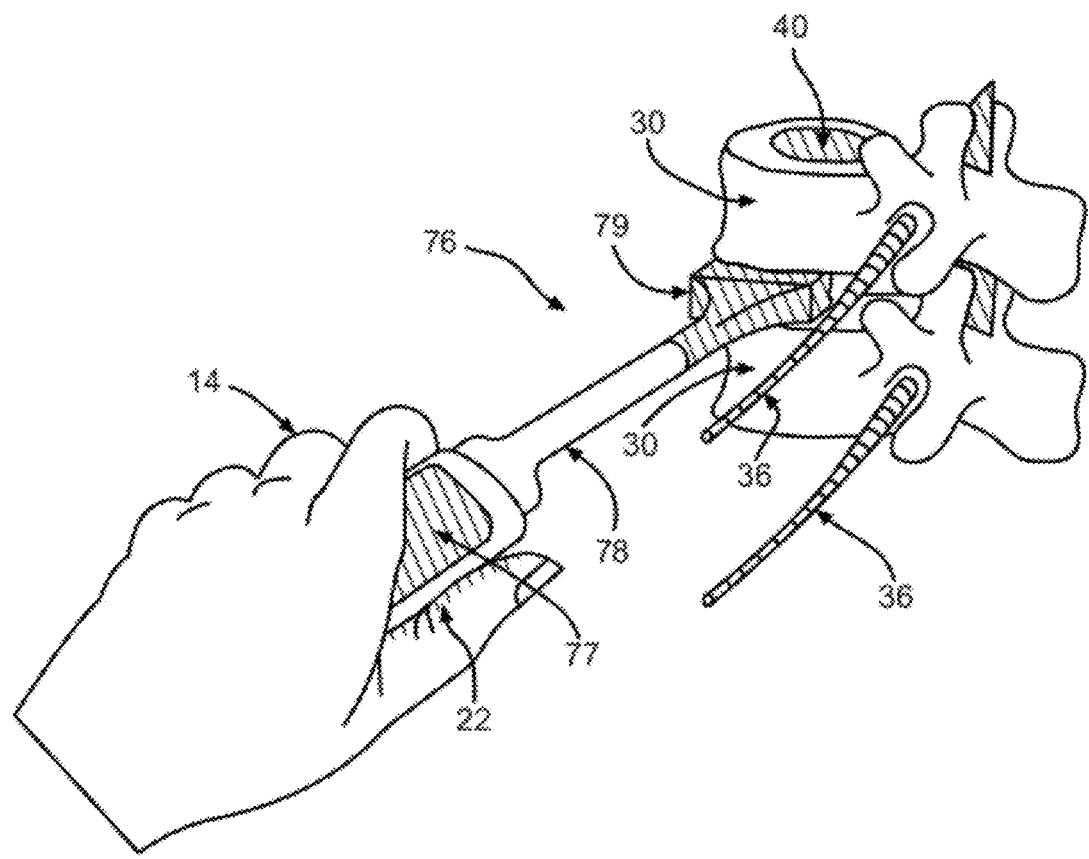
FIG. 20 is an isometric view of an electrifiable wireless implant trial instrument.

In FIG. 20, an electrically conductive wireless implant trial instrument 76 is inserted between the vertebrae 30. The stimulating current flows from glove electrical conductive open contact surface 22 of the glove 14, to the implant trial instrument electrical contact 77, to the isolated portion of the implant trial instrument 78, to the end effector 79 and finally to the nervous system component 36. The end effector 79 of the implant trial instrument is used to send a stimulation current into the patient's body and the readings of the neuromonitoring modalities inform the IONM specialist on the relative proximity of this implant trial instrument to a nervous system component. Alternatively, the end effector 79 of the implant instrument trial 76 could be quick-coupled to the isolated portion 78 of the implant trial instrument. The electrically conductive portion of end effector 79 may be of different pattern depending on which type of surgeries the instrument is used for. As example, only an edge of the implant trail may be electrically conductive and stimulating if the instrument is passing close to the motor nerve 36 during a posterior extracavitary lumbar interbody fusion approach. Multiple portions of the implant trial may be stimulating depending on the surgical approach and the nerves at risk during the surgery.

Figure 21:
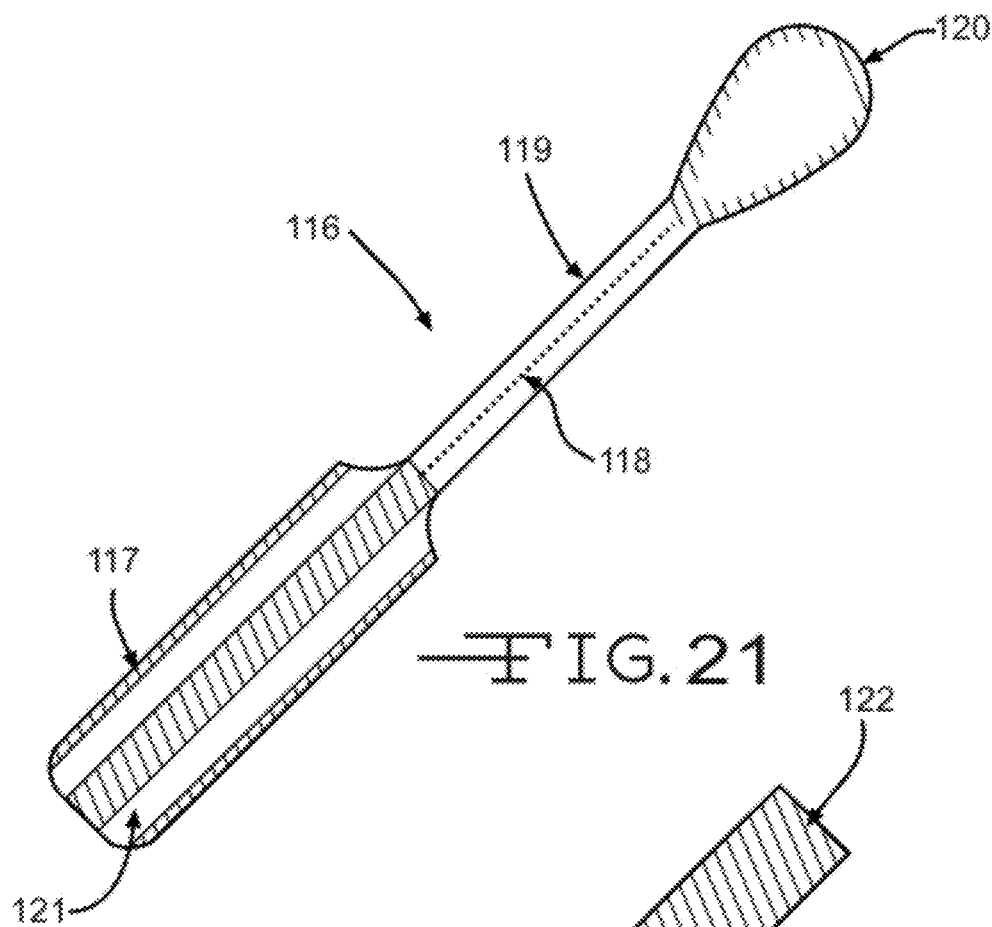
FIG. 21 is an isometric view of an electrifiable wireless curette.

In FIG. 21, an electrically conductive wireless curette 116 is shown. In the preferred embodiment, the curette has a handle where electrically conductive sections 117 are alternated with gripping sections 121. The electrically conductive sections are connected to the end effector 120 of the curette via the conductive core 118 that is isolated by the core insulator 119. The conductive core 118 is the structural elongated portion of the curette and this portion is coated with a core insulator 119. The end effector 120 of the curette is used to send stimulation current into the patient's body and the readings of the neuromonitoring modalities inform the IONM specialist on the relative proximity of this curette to a nervous system component. In another embodiment, the structural elongated portion of the curette is the core insulator 119 in which a conductive core 118 is inserted. In a different embodiment, the handle has only one electrically conductive zone. With the same principle of having a conductive handle, an insolated conductive core and an electrically conductive end effector, many other similar microsurgical instruments for brain or ENT surgeries like rhoton can be used with the electrifiable glove to transmit electrical stimulations into tissues.

Figure 22:
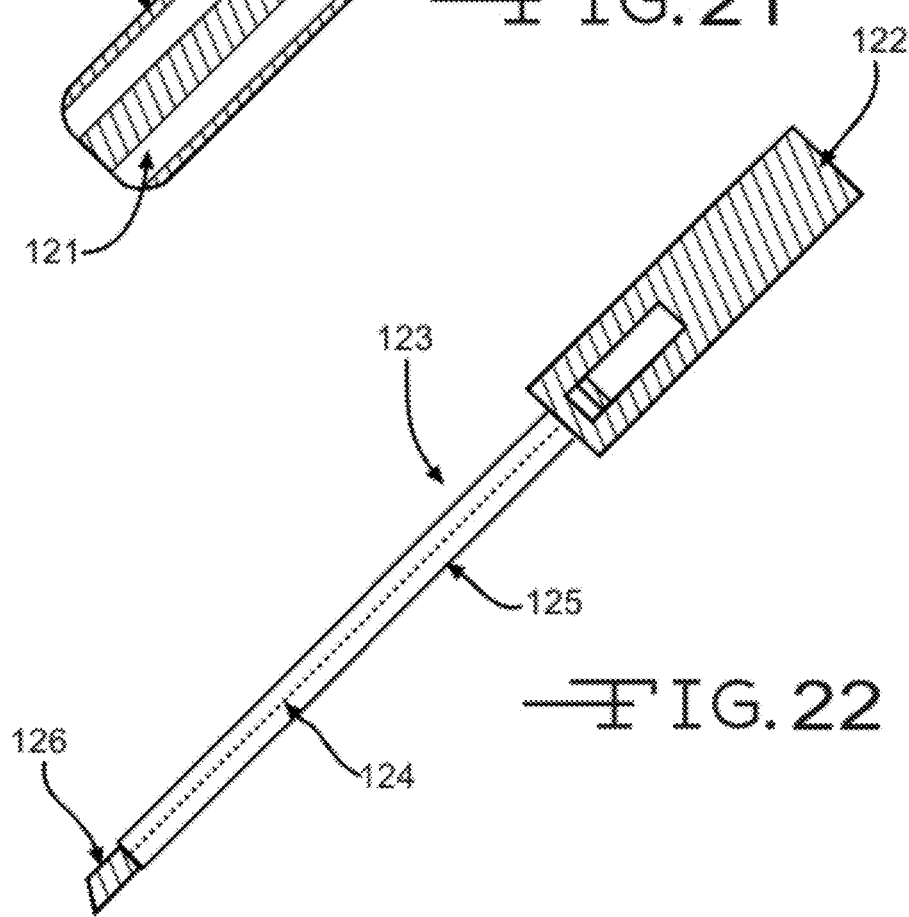
FIG. 22 is an isometric view of an electrifiable wireless annulotomy knife.

In FIG. 22, an electrically conductive wireless annulotomy knife 123 is shown. The electrically conductive handle 122 is connected to the end effector 126 of the annulotomy knife via the conductive core 124 that is isolated by the core insulator 125. The conductive core 124 is the structural elongated portion of the annulotomy knife and this portion is coated with a core insulator 125. The end effector 126 of the annulotomy knife is used to send stimulation current into the patient's body and the readings of the neuromonitoring modalities inform the IONM specialist on the relative proximity of this annulotomy knife to a nervous system component. In another embodiment, the structural elongated portion of the annulotomy knife is the core insulator 125 in which a conductive core 124 is inserted. In a different embodiment, the knife may also work as a bipolar instrument in the same manner as described in FIG. 16. In this way, stimulation of tissues may be performed while cutting.

Table 1 below shows an example of the electrically conductive compound formulation.

TABLE 1

| Material | Proportion (%) |
| --- | --- |
| SBR Pressure Sensitive Adhesive | 40-50% |
| Silver (Ag) Flake, 8-10 · m | 30-40% |
| Silver (Ag) Powder, 0.1-0.5 · m | 5-10% |
| Dispersant | 2-5% |
| Toluene | 10-20% |

Different experimentations have been conducted to show the electrical properties of different configurations of the conductive compound. In order to demonstrate the properties of the conductive compound described in Table 1, two different configurations (processes of application) are used and three different tests are performed for each configuration. In the two configurations, the conductive compound was applied on a cured film of neoprene rubber of 8 to 10 mils thickness. The first configuration is spraying where the conductive compound is atomized on the neoprene rubber film. The second configuration is dispensing where the conductive compound is applied on the neoprene rubber film using a syringe having a small needle that is sufficient to, for the most part, allow the conductive material to be released from the needle.

The first test performed is the measurement of the electrical resistance while stretching the conductive film to double its original length (100% elongation). The rate of stretch during the test is 0.1 mm/sec. The second test performed is the measurement of the electrical resistance while stretching the conductive film to 3.5 times its original length (250% elongation). The rate of stretch during the test is 0.05 mm/sec. The third test is performed to demonstrate the recovery of the conductive compound. The test is performed for 50 cycles of a 50% stretch of the conductive film. The rate of stretch during the test is 0.6 mm/sec.

Figure 23:
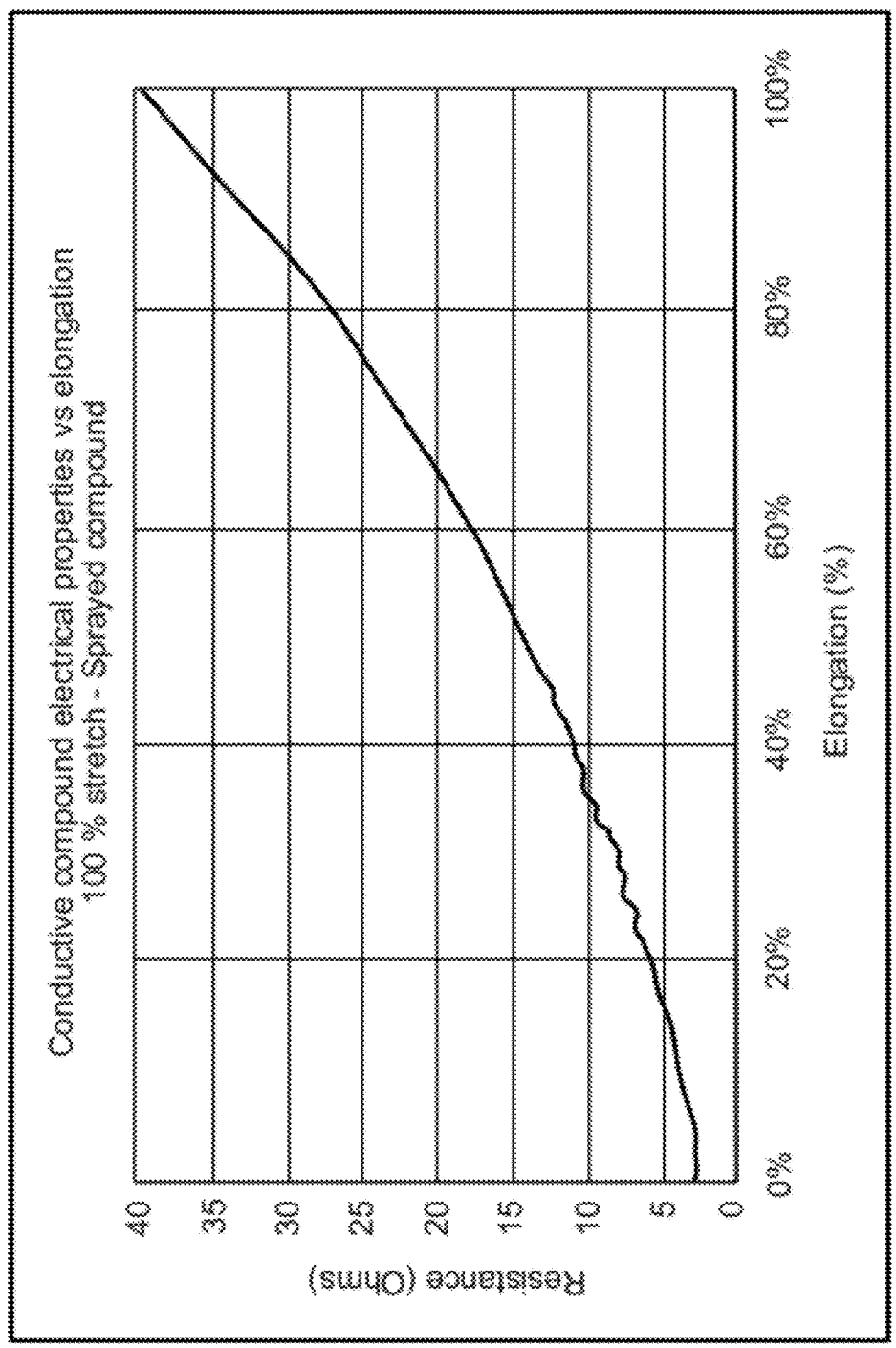
FIG. 23 shows a graph of the elongation vs. electrical resistance of the novel electrically conductive compound sprayed on a neoprene film.
Figure 24:
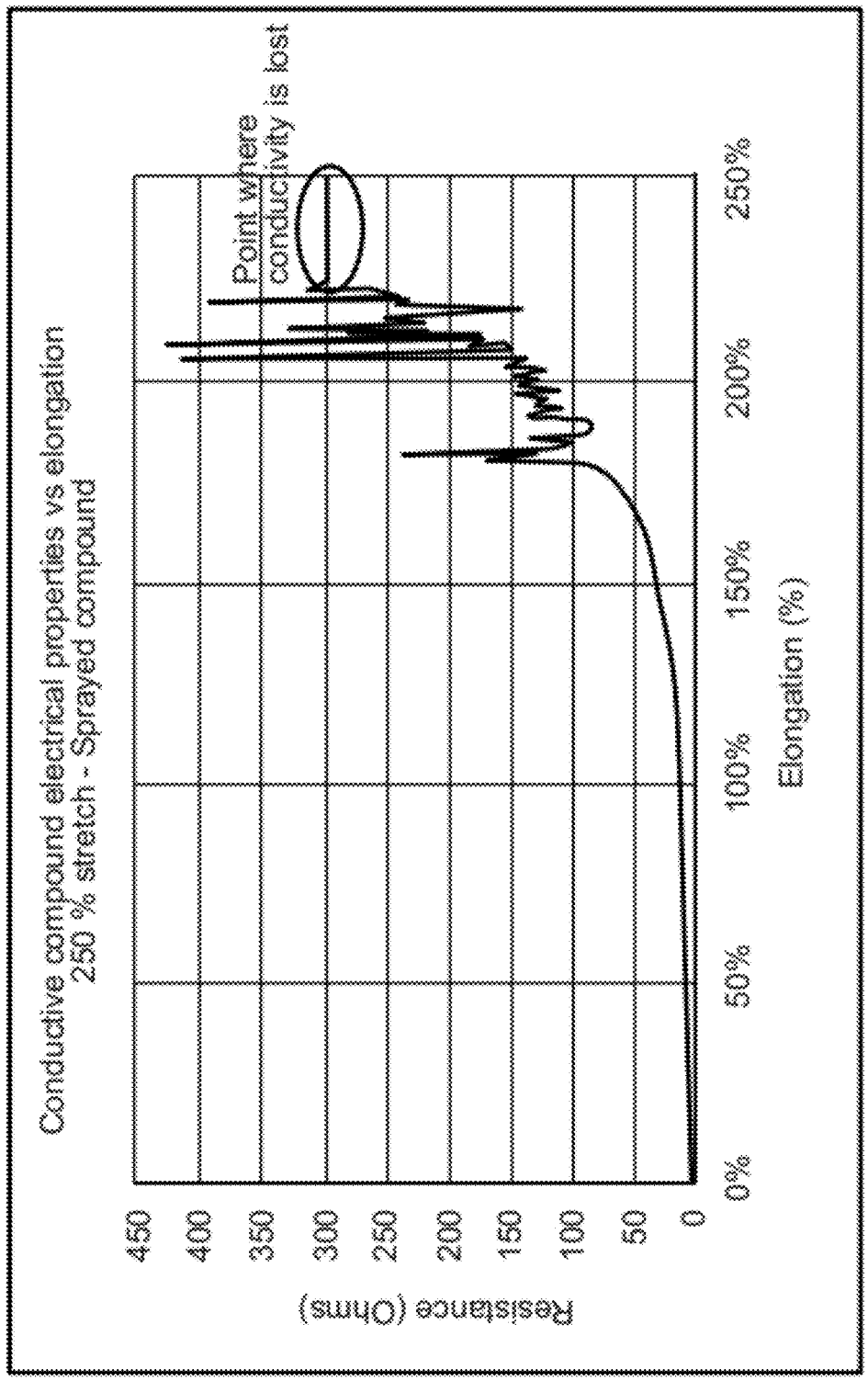
FIG. 24 shows a different graph of the elongation vs. electrical resistance of the novel electrically conductive compound sprayed on a neoprene film.
Figure 25:
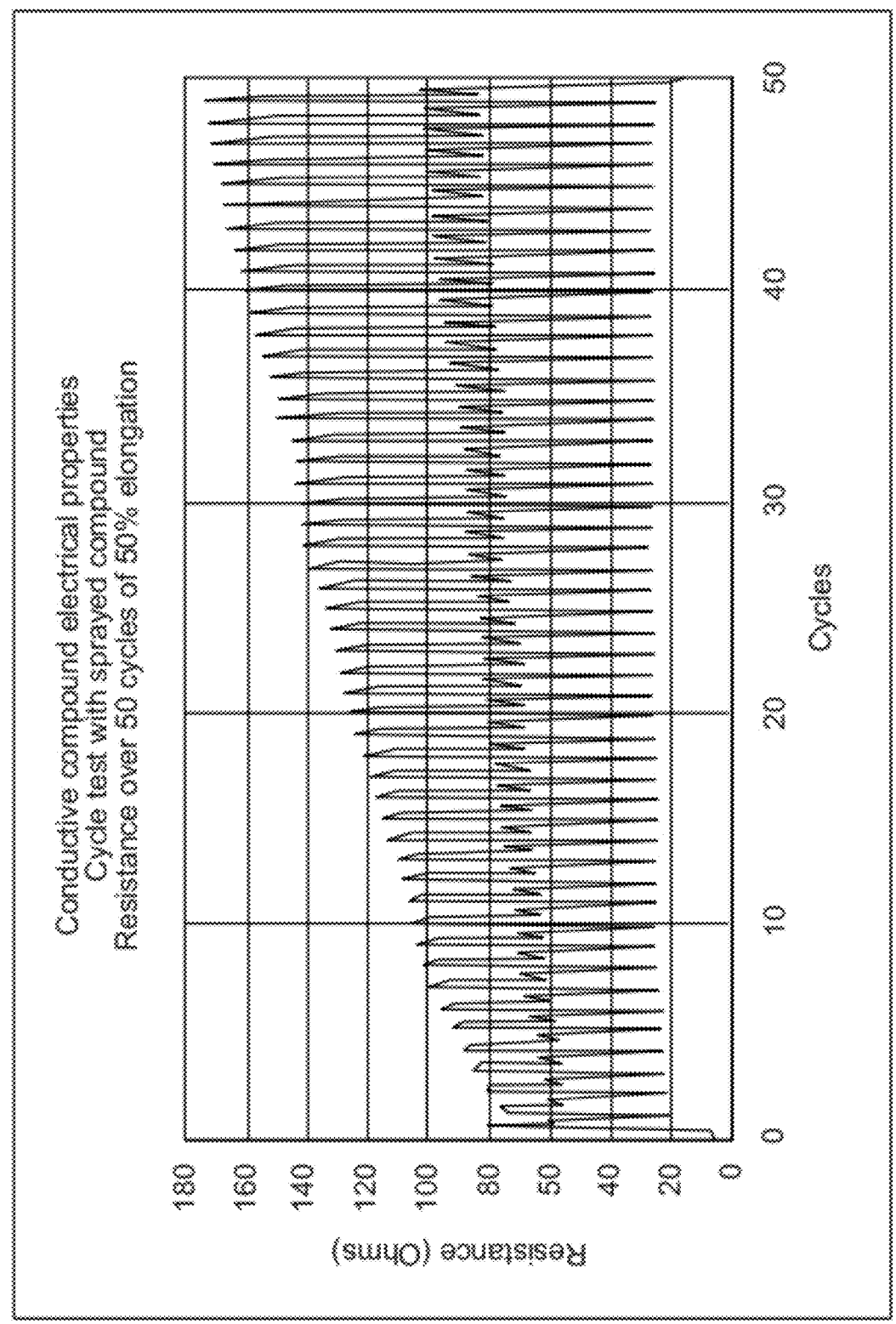
FIG. 25 shows a graph of the elongation vs. electrical resistance of the novel electrically conductive compound sprayed on a neoprene film during a cyclic test.

FIGS. 23, 24, 25 show the results of the three tests for the spraying configuration. The dimensions of path are 0.09 mm thickness×6.0 mm width×120 mm length.

Figure 26:
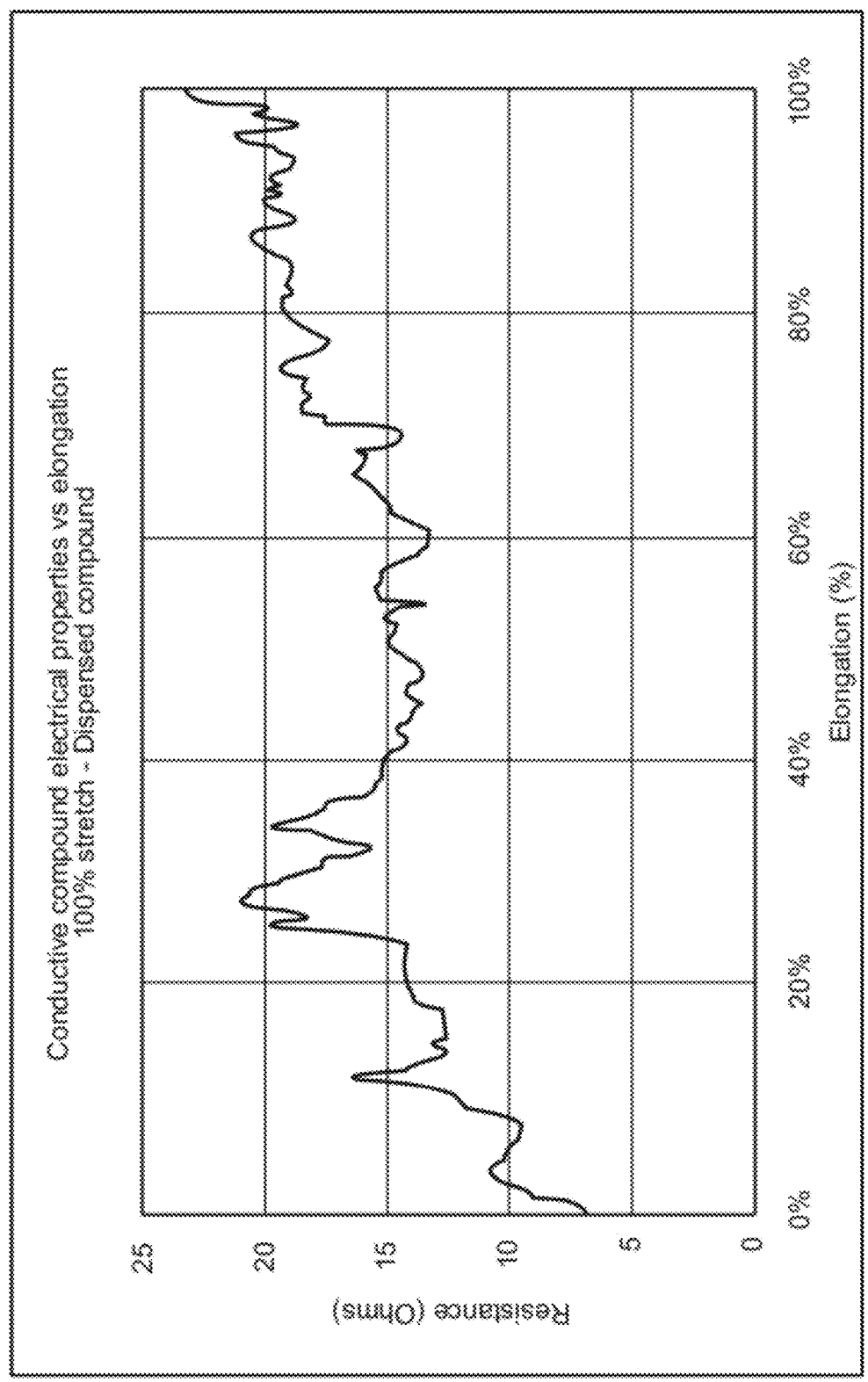
FIG. 26 shows a graph of the elongation vs. electrical resistance of the novel electrically conductive compound dispensed on a neoprene film.
Figure 27:
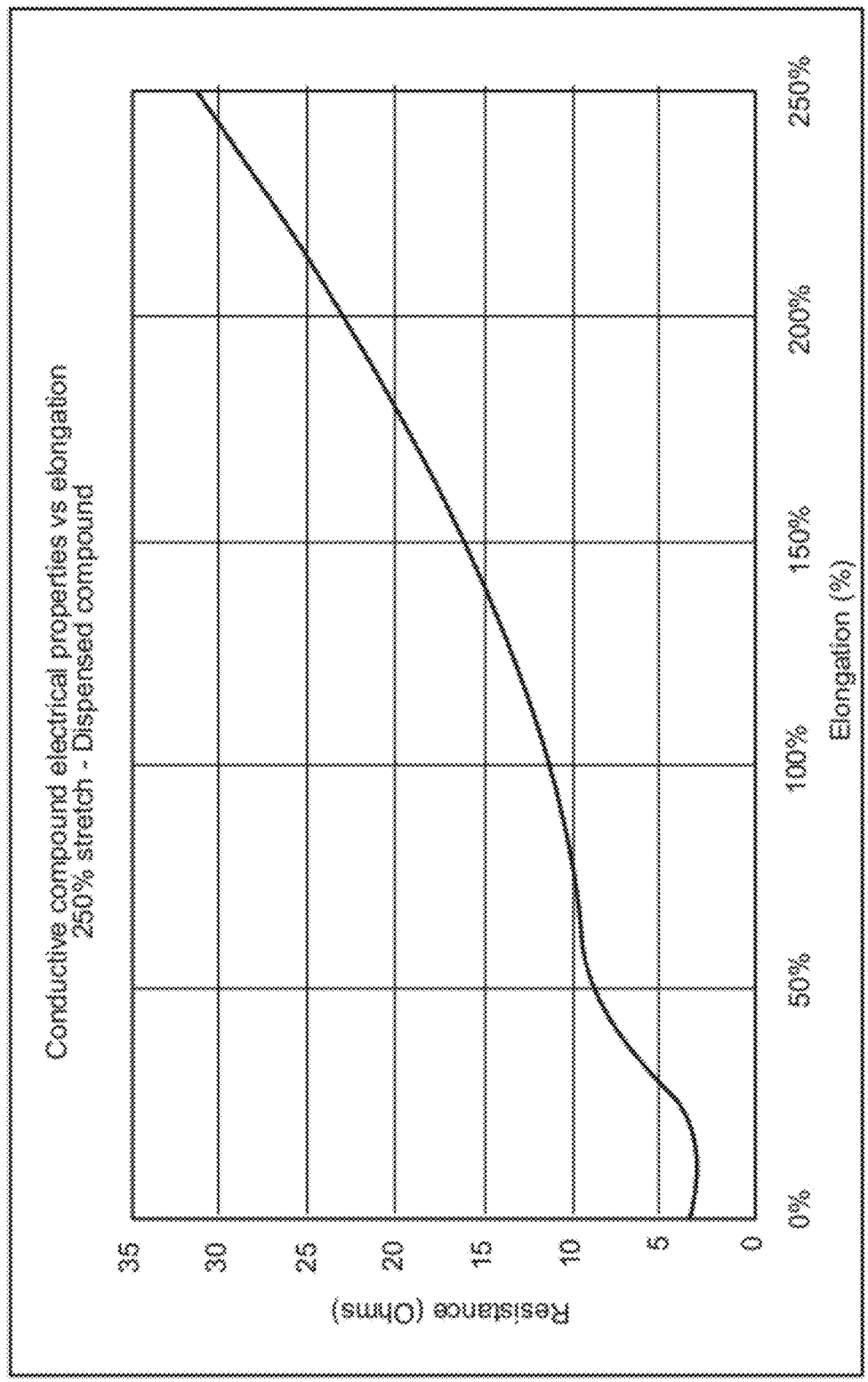
FIG. 27 shows a different graph of the elongation vs. electrical resistance of the novel electrically conductive compound dispensed on a neoprene film.
Figure 28:
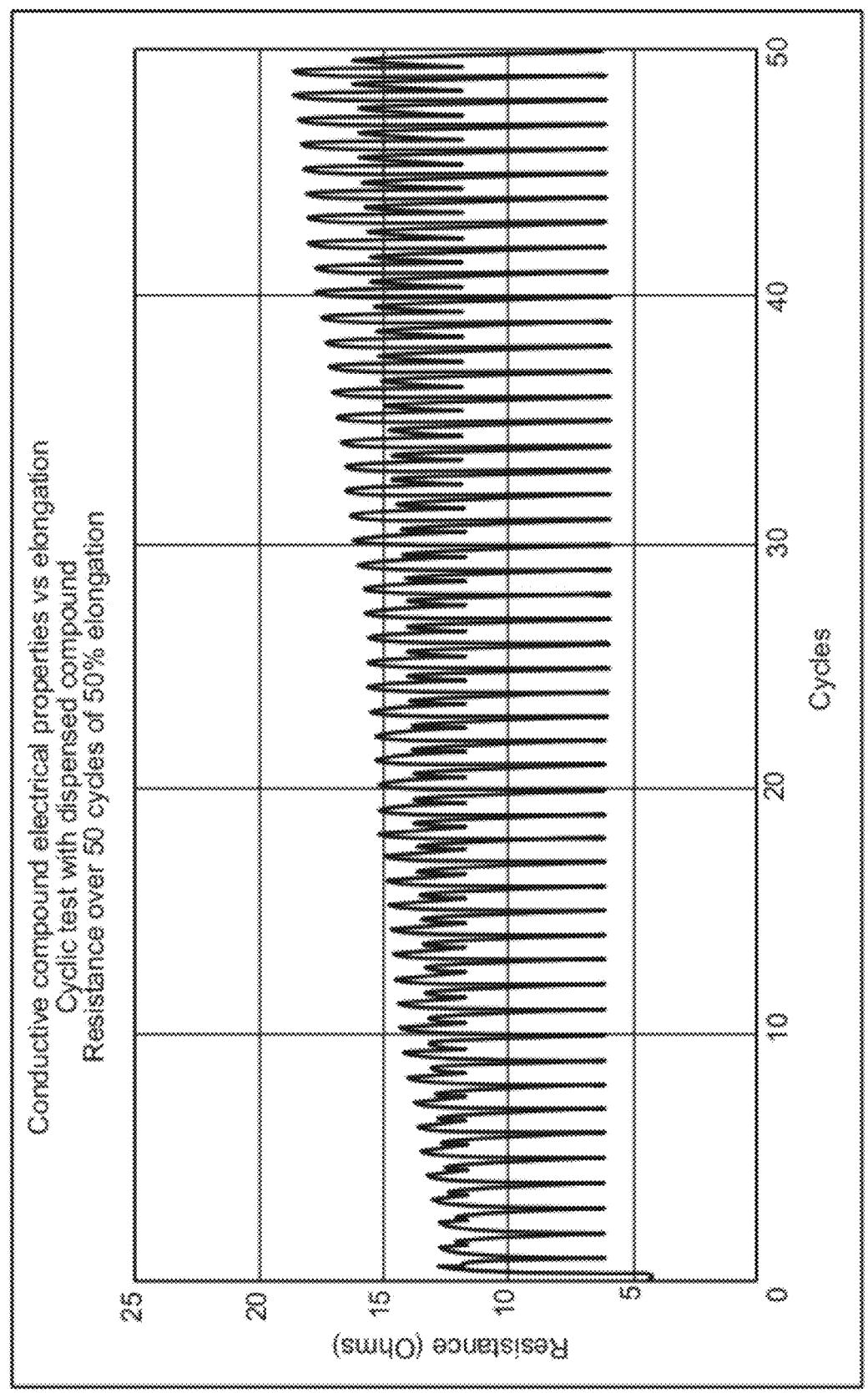
FIG. 28 shows a graph of the elongation vs. electrical resistance of the novel electrically conductive compound dispensed on a neoprene film during a cyclic test.

FIGS. 26, 27, 28 show the results of the tests for the dispensing configuration. The dimensions of path are 0.28 mm thickness×2.4 mm width×120 mm length. When comparing the spraying configuration in relation to the dispensing configuration, the dispensing configuration shows greater and superior electrical properties even after being extensively elongated. That being said, both configurations are substantially superior to conventional conductive glove embodiments that have poor electrical pathways when the glove is elongated 100% as suggested and disclosed in relation to the background of the invention.

Figure 29:
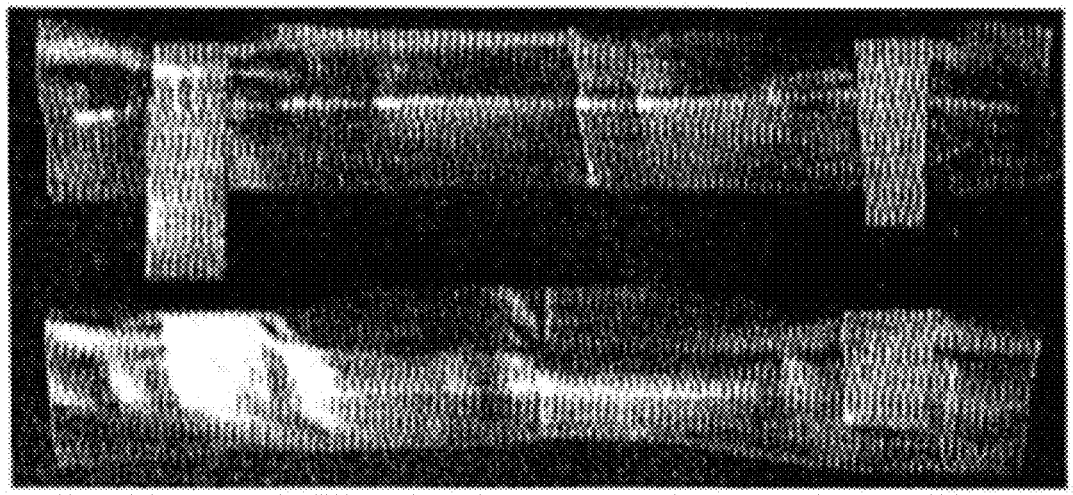
FIG. 29 shows a picture of the sprayed and dispensed electrically conductive compound on a neoprene film.
Figure 30:
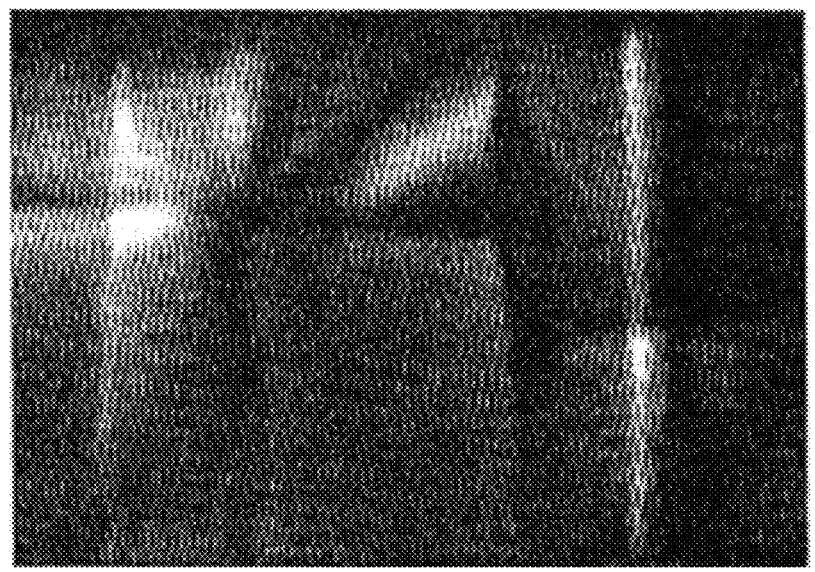
FIG. 30 shows a close-up picture of the sprayed and dispensed electrically conductive compound on a neoprene film.

FIG. 29 shows the pictures of the electrical pathways applied on the neoprene film. The line on the top of the picture is dispensed; the line on the bottom of the picture is sprayed. FIG. 30 shows a close-up of the same lines.

The graphs shown in FIGS. 23 to 28 demonstrate that the manufacturing process used to deposit the compound on the substrate has a direct influence on the quantity of material that is fixed to the substrate. Moreover, the process also has an effect on the shape of the cross section of the conductive compound. The results show the dispensed line has a better conductivity and the reason is due to its thickness. The conductive compound offers the option to be dispensed with a syringe type process or atomized with a spray process. With both processes, the novel electrically conductive compound offers great conductive properties under stretch that has never been created today.

Stretchable Electrically Conductive Wire

This section discloses the use of the electrically conductive compound described in the present invention with a novel method of making a stretchable electrically conductive wire.

In one embodiment, the electrically conductive compound is injected into a stretchable tube. The tube can be made of materials in the families of silicone, polyurethane, PVC, neoprene, natural or synthetic latex or the like. The silicone material is preferred for permanent implantable lead wire for medical applications. The liquid compound can be either injected into the tube from one extremity or vacuum into the tube with the source of aspiration being at the opposite end of the entry point of the compound. Both ways must insure an even repartition of the compound inside the tube without any void. The liquid compound is then dried in an oven or at room temperature until all the solvent is gone. In order to demonstrate the electrical properties of the stretchable wire, the following experiments have been conducted on a wire made of a silicone tube having an outside diameter of ⅛" and an inside diameter of 0.063".

Figure 31:
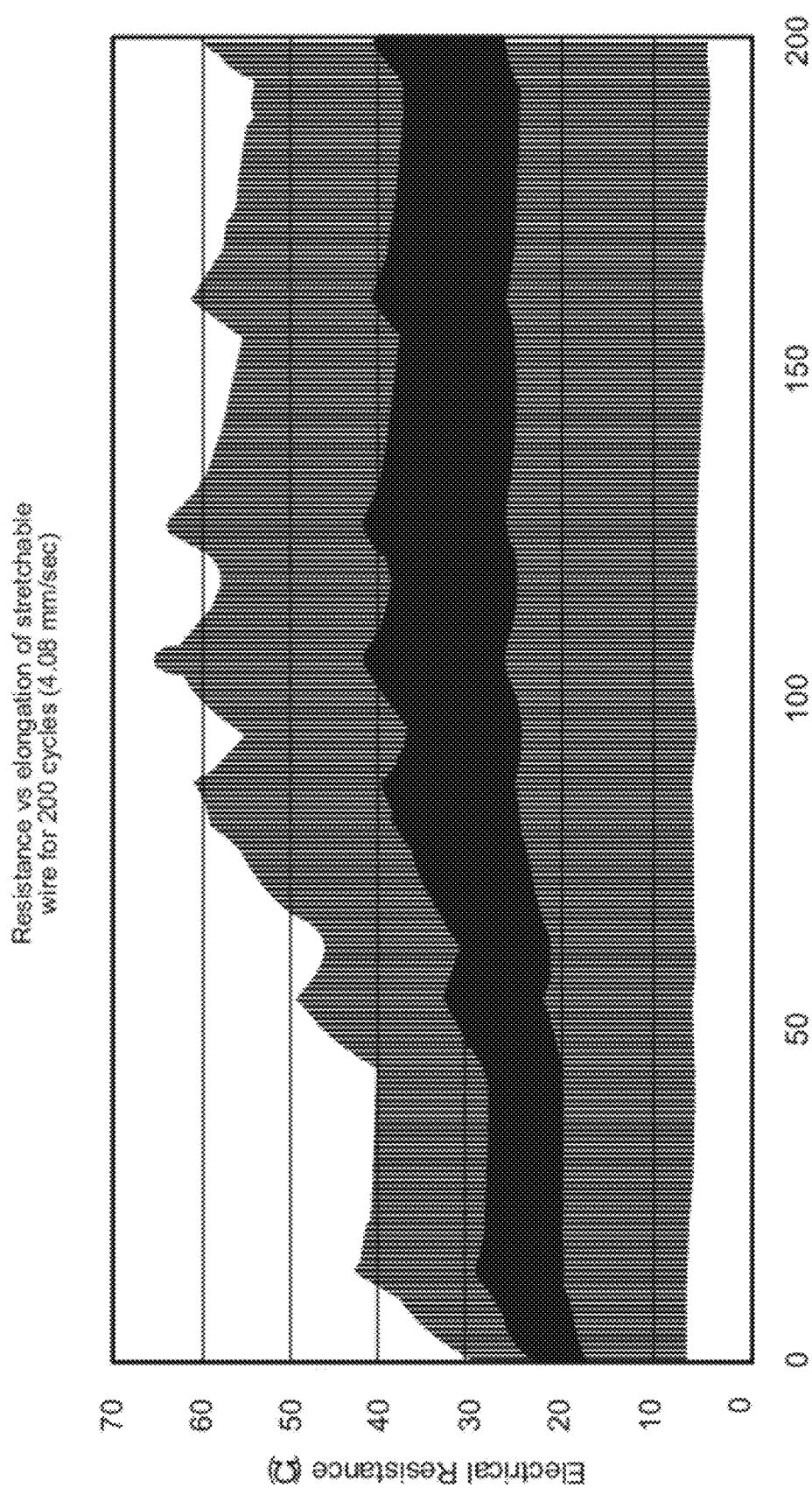
FIG. 31 shows the evolution of the electrical resistance of a novel stretchable wire made with a silicone tube having the electrically conductive compound in it during cyclic elongations.
Figure 32:
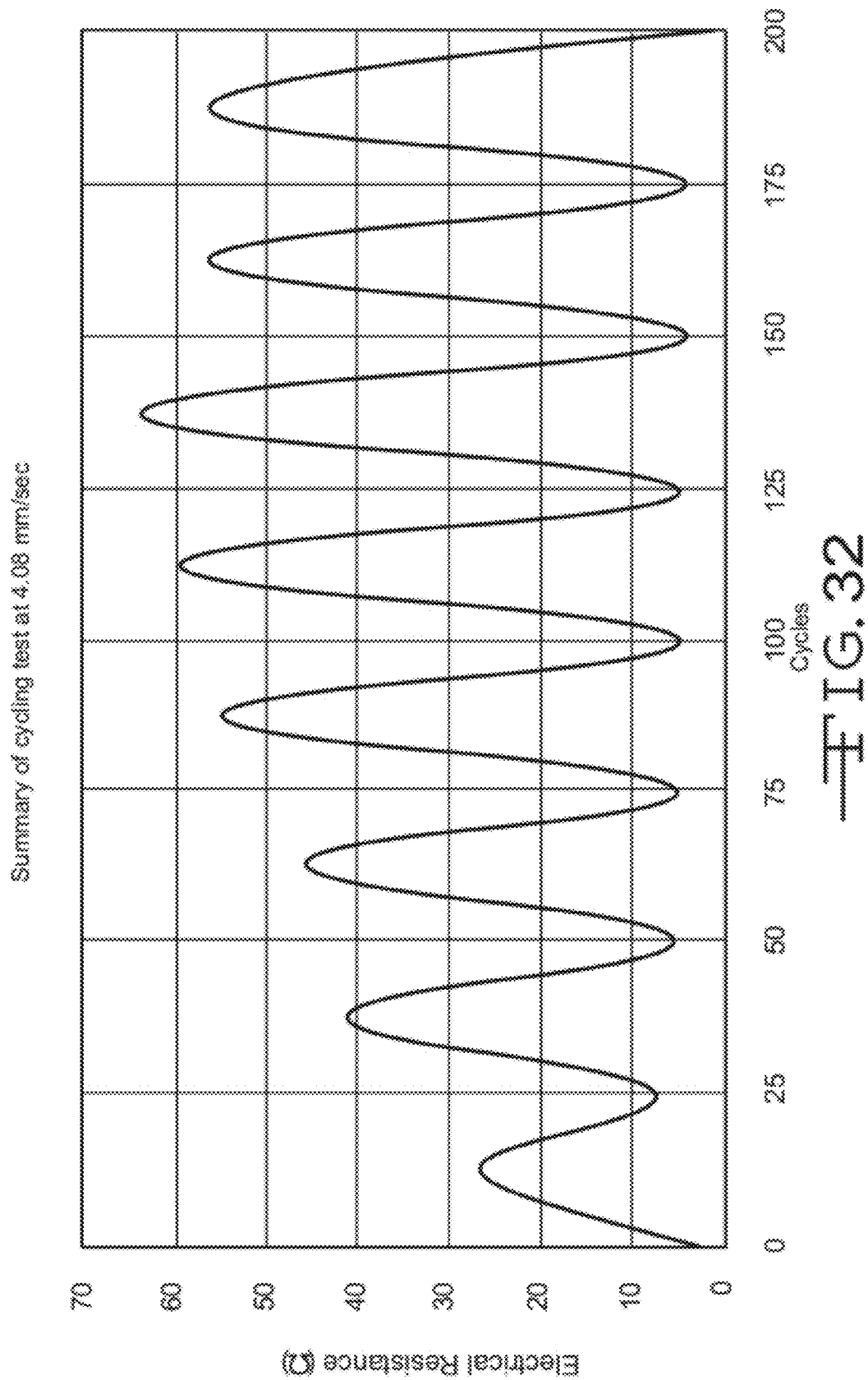
FIG. 32 shows the evolution of the electrical resistance of a stretchable wire made with a silicone tube having the electrically conductive compound in it during cyclic elongations.
Figure 33:
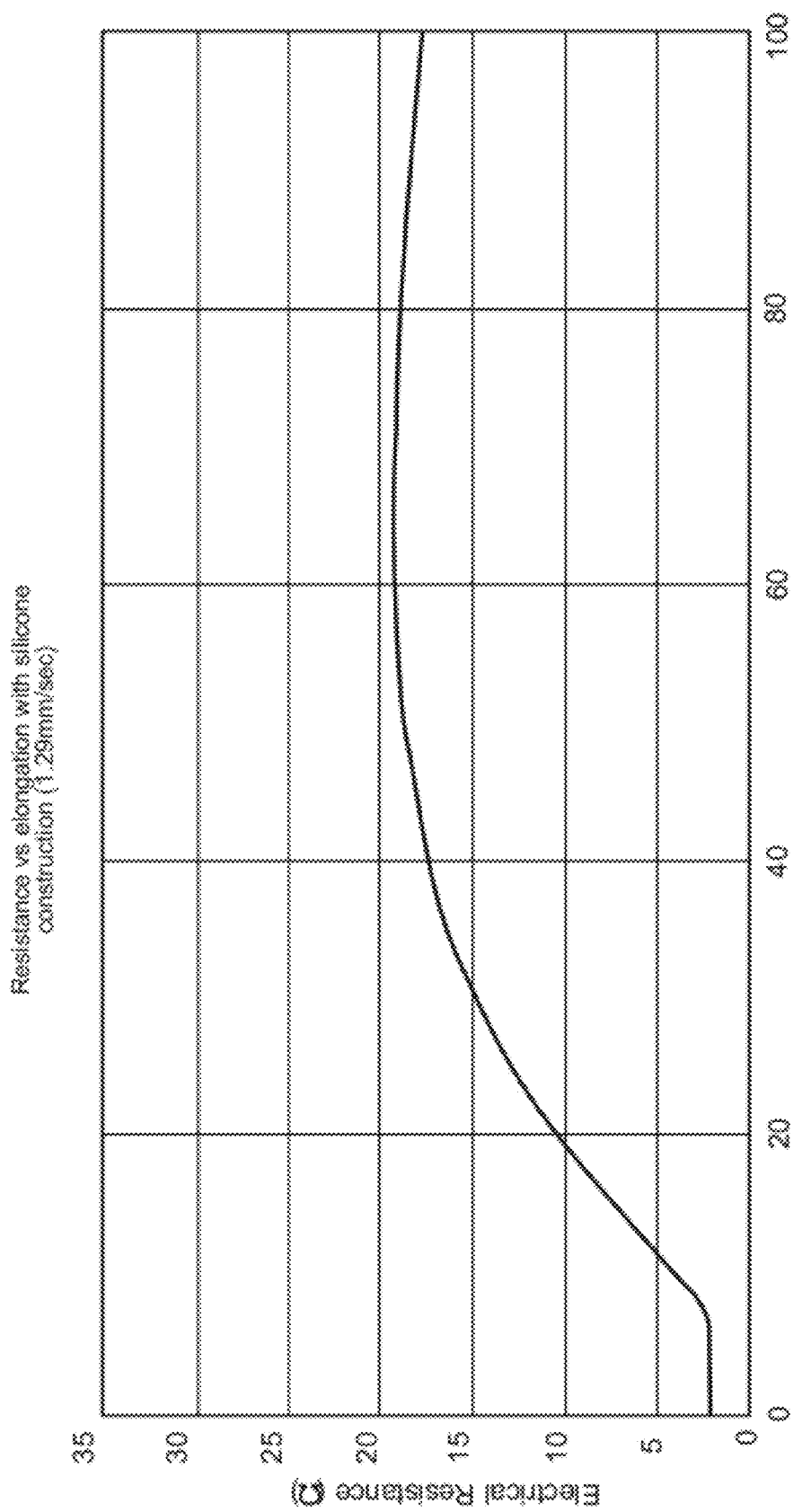
FIG. 33 shows a graph of the elongation vs. electrical resistance of a stretchable wire made with a silicone tube having the electrically conductive compound in it.
Figure 34:
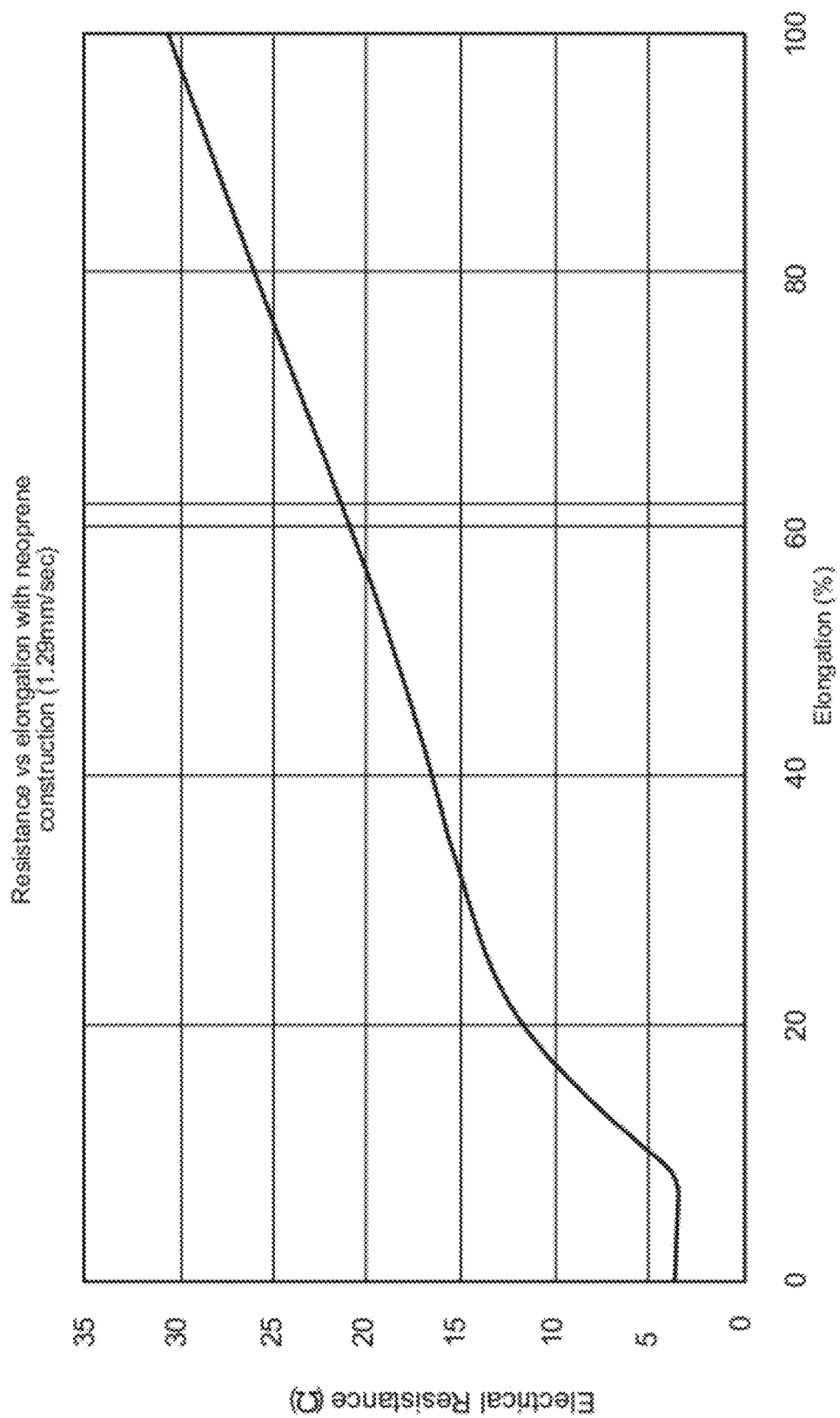
FIG. 34 shows a graph of the elongation vs. electrical resistance of a stretchable wire made with a neoprene film having the electrically conductive compound on it.

The conductive compound described in Table 1 was injected into the silicone tube on 6" length. Two cupper wires were placed on each ends of the tube to ease the measurements. FIG. 31 shows the evolution of the electrical resistance of the wire during cyclic elongation of 50%. FIG. 32 shows the same evolution of the electrical resistance of the wire during cyclic elongation of 50% with less measurement points. FIG. 33 shows the evolution of the electrical resistance during an elongation of 100% (double of the initial length), using the same sample as the one previously used during the cyclic testing. FIG. 34 shows the evolution of the electrical resistance during an elongation of 100%, using a film of neoprene having a line of the electrically conductive compound described in Table 1 applied with a paintbrush. All these experiments show the ability of the compound to remain electrically conductive during and after a high elongation.

Figure 41:
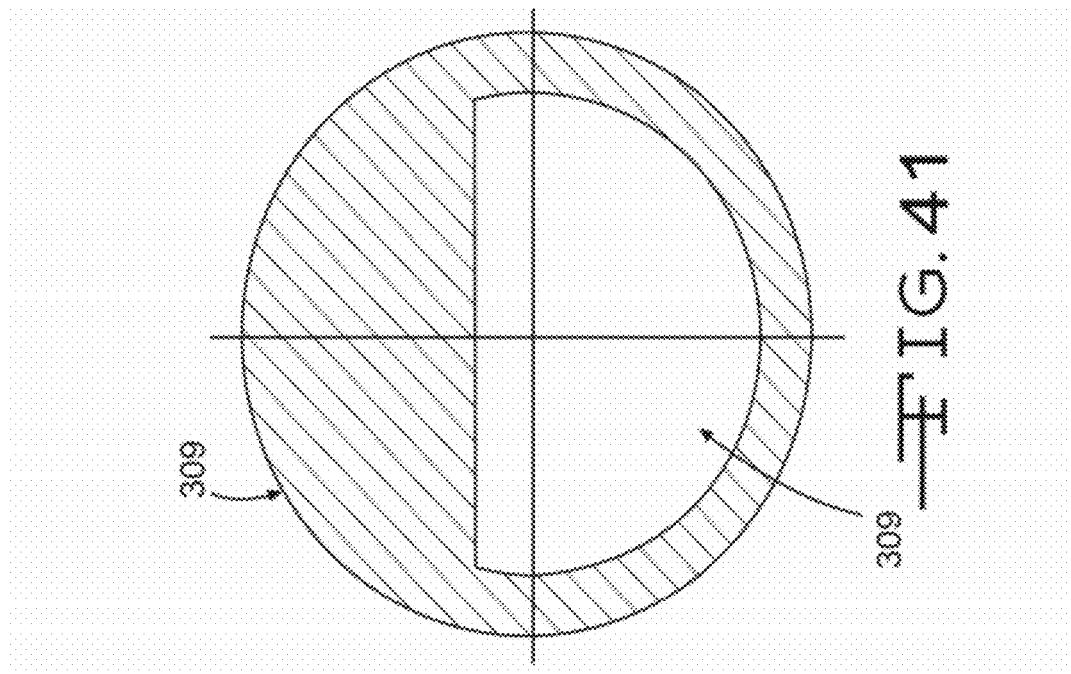
FIG. 41 shows the assembly of the two halves of a different stretchable wire.
Figure 40:
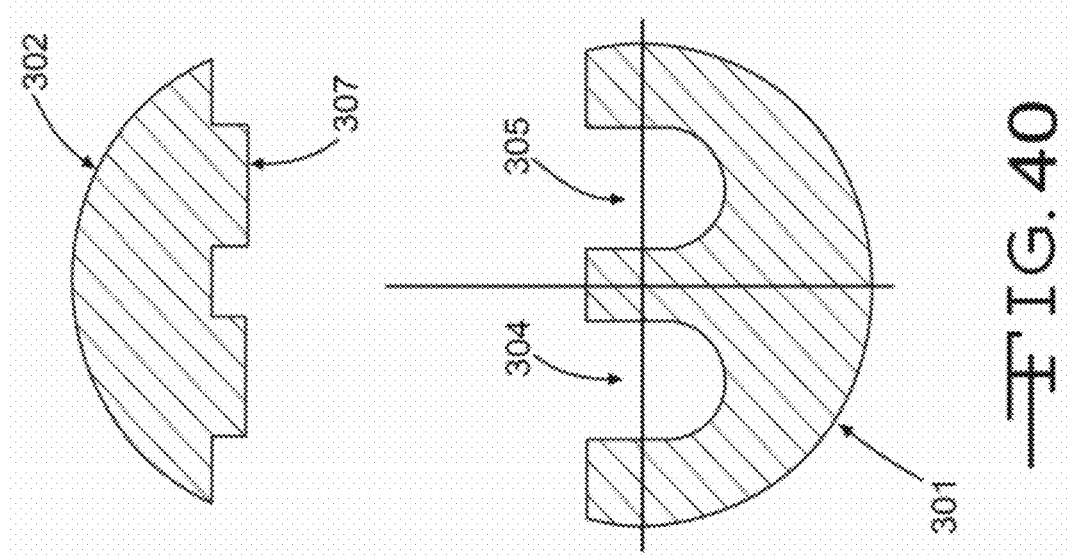
FIG. 40 shows the bottom and upper halves of a different stretchable wire.

FIG. 39 shows the preferred embodiment of the stretchable electrically conductive wire 303 and the method of making it. As shown in FIG. 35, the bottom half 301 of the stretchable wire has at least one groove 304 going from the first end of the wire up to the second end of the wire along its longitudinal axis. One or more groove 305 may be added in order to obtain more than one electrical path. The upper half 302 of the stretchable wire as shown in FIG. 36 is then assembled with the bottom half 301 in a subsequent operation, after the liquid electrically conductive compound has been dispensed into the at least one groove 304 and dried. FIGS. 37 and 38 show typical dimensions of such a wire. The bottom half wire 301 and the upper half wire 302 can be made of materials in the families of silicone, polyurethane, PVC, neoprene, natural or synthetic latex or the like. Similar material is preferred but not limited for making the bottom and upper half wires. The silicone material is preferred for permanent implantable lead wire for medical applications. The dispensing equipment used to put the liquid compound into the groove must insure an even repartition of it without any void in order to guarantee continuity of the electrical conductor. FIG. 40 shows a similar concept where the upper half of the wire 302 has a positive feature 307 that facilitates the positioning of the upper half with the bottom half 301 during assembling. FIG. 41 shows a different shape of wire that has only one lumen 309. It is understood by those skilled in the art that various changes in form, construction, number of conductive pathways, stretchable materials and dimensions maybe made therein without departing from the spirit and scope of the present invention.

Figure 42:
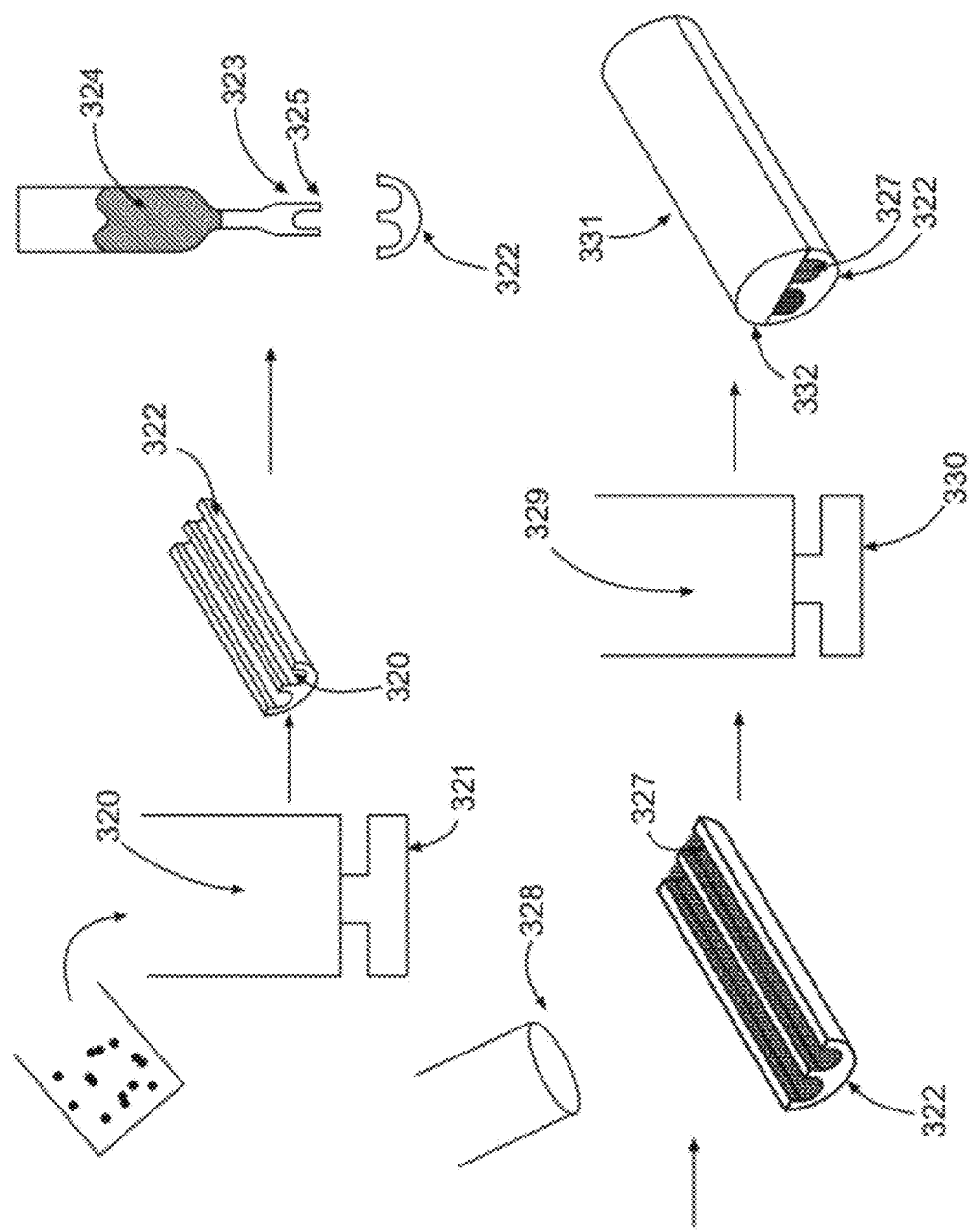
FIG. 42 shows a typical in-line manufacturing process of a stretchable wire.

FIG. 42 shows a typical installation that may be use to produce the stretchable electrically conductive wire 331 utilizing an in-line manufacturing process. The stretchable material 320 is loaded into an extruding machine and heated. The extrusion head 321 forms the bottom half 322 of the stretchable wire. At least one groove 326 is made in order to receive the electrically conductive pathway. In a continuous step, a dispensing station dispenses the electrically compound 324 in a liquid state into the groove 326. A dispensing head 323 controls the flow rate of the liquid compound in relationship to the speed of the bottom half wire exiting the extruding machine. At least one needle 325 insures precise dispensing of the compound into the groove. Still in a continuous step, a heating station 328 insures the drying of the conductive compound. Once dried, the bottom half wire with the electrically conductive pathway 327 enter into another extruding machine which contains a stretchable material 329. The extruding head 330 co-extrude the upper half 332 of the wire over the bottom half previously made.

In a sensorial application, the electrically conductive compound can be applied on the fingertips of a robotic hand to measure its tactile sensitivity. By applying a pressure on the fingertips, the electrical resistivity of the coating changes and information on the sensitivity can be transmitted to the CPU of the robot.

It will be understood that the particular method and devices embodying the invention are shown by way of illustration and not as a limitation of the invention. In general, the invention is contemplated to encompass all variations of constructions, wherein an electrical connection is made between a surgical glove and any instrument useful for stimulation for the purpose of intra-operatively neuromonitoring a patient's nervous and muscular systems. The scope also includes a novel neuromonitoring system with wireless interconnectivity and remote viewing options and a process of making an electrically conductive and stretchable coating on rubber. Therefore, the principles and features of this invention may be employed in various and numerous embodiments without departing from the scope of the invention. It is understood by those skilled in the art that various changes in form, construction and detail maybe made therein without departing from the spirit and scope of the invention as defined by the appended claims.

We claim:

1. An electrically, elongatable conductive medical glove comprising: an electrically insulated elastic glove body having an inner surface for intimately contacting a portion of a user's hand and an outer surface, wherein the material for the electrically insulated elastic glove body is selected from the group consisting of latex, nitrile, polyisoprene, polychloroprene, and vinyl; a portion of the outer surface of the glove body has an integral electrically conductive elastic coating, the integral electrically conductive elastic coating comprises a solvent-based polymer having electrically conductive flakes (i) wherein each flake has an average flake size between 5 and 15 microns, and (ii) positioned in the solvent-based polymer to remain conductive at 50% of stretch for the electrically insulated elastically expandable glove body, the integral electrically conductive elastic coating is on the portion that is an electrically, elongatable conductive path, the elasticity of the coating being selected to functionally match the elasticity of the electrically insulated elastic glove body; a water-based protective elastic coating, wherein a portion of the electrically, elongated conductive path is covered by the water-based protective elastic coating and maintains full integration with the electrically insulated elastic glove body to the elastic limit of the electrically insulated elastic glove body while being adapted to recover its initial shape when relaxed; wherein the electrically, elongatable conductive path maintains full integration with the electrically insulated elastic glove body to the elastic limit of the electrically insulated elastic glove body while maintaining conductivity after donning the electrically insulated elastic glove in an elastically expanded state wherein at least a section of the electrically, elongated conductive path is capable of being elongated between 100 and 250%, the electrically insulated elastic glove body thereby capable of recovering its initial shape when the electrically insulated elastic glove body is relaxed; where the elasticity of the integral electrically conductive elastic coating is functionally equivalent to the elasticity of the electrically insulated elastic glove body; wherein the electrically, elongatable conductive path maintains full integration with the electrically insulated elastic glove body and remains continuously conductive while elongated with a resistivity below 2000 Ohms and is capable of recovering its initial shape; wherein the solvent-based polymer used in the integral electrically conductive elastic coating is styrene and the integral electrically conductive elastic coating further comprises a dispersant agent; and the water-based protective elastic coating is urethane.

2. The device of claim 1, wherein the electrically conductive filler is silver flakes.

3. The device of claim 1, wherein the electrically conductive glove further comprises an electrical connector which is connected to a source of electrical stimulation.

4. The device of claim 1, wherein the thickness of the said electrically conductive elastic coating is between 1 and 3 mils (thousandth of an inch).

5. The device of claim 2, wherein the electrically conductive elastic coating is composed so as to be capable of temporary elongation of up to 300% while remaining conductive with a resistivity below 2000 Ohms after recovery of its initial shape and so as to remain electrically conductive with a resistivity below 2000 Ohms after temporary elongation up to 50%.

6. The device of claim 1, wherein the solvent in the solvent-based styrene polymer is a blend of toluene, methyl-ethyl-ketone and heptanes.

7. The device of claim 1, wherein the integral electrically conductive elastic coating is applied by (a) sprayed through an atomizer or (b) dispensed through a syringe.

8. The device of claim 3, further comprising an instrument, wherein the electrical stimulation is transferred from the source to the instrument through the electrically, elongatable conductive path.

9. The device of claim 3, wherein the source of electrical stimulation is fixed to the glove and in direct electrical contact with the electrically, elongatable conductive path.

10. The device of claim 3, wherein the electrical stimulation is transmitted to the electrically, elongatable conductive path through an electrical conductor mounted on a surgical gown.

11. The device of claim 1, wherein the protective elastic coating insulates the outside of the conductive path on the glove.

12. The device of claim 8, further comprising a second electrically elongatable conductive path.

13. The device of claim 8, wherein the instrument is one of a group of instruments consisting of a medical syringe, a medical needle, a tap, a drill bit, a screwdriver, a wrench, a retractor, a rongeur, an awl, a monopolar probe, a cannula, a K-wire, a distractor, a curette, a rasp, a chisel, a trial implant, an annulotomy knife, a scalpel, a rhoton, a suction device, an electrosurgical cutter/coagulation device, a ratcheting handle, a torque limiting handle, a torque measuring handle, a fixed handle, powered drill, and a quick coupling instrument.

14. The device of claim 8, wherein the second path is used for detecting the presence of the instrument in contact with the glove.

15. The device of claim 12, wherein the instrument is a bipolar instrument having two electrical conductors for connecting with the first and second electrically, elongatable conductive paths on the glove.

16. The system of claim 15, wherein the bipolar instrument is one of a group of bipolar instruments consisting of a bipolar probe, bipolar scissors, bipolar forceps, bipolar knife, a bipolar clamp, a bipolar rhoton, and bipolar tweezers.

17. An electrical conductor comprising: an electrically insulated elastically expandable member selected from the group consisting of latex, nitrile, polyisoprene, polychloroprene, and vinyl; a portion of the outer surface of the expandable member has an integral electrically conductive elastic coating, the integral electrically conductive elastic coating comprises a solvent-based polymer having electrically conductive flakes (i) wherein each flake has an average flake size between 5 and 15 microns and (ii) positioned in the solvent-based polymer to remain conductive at 50% of stretch for the electrically insulated elastically expandable member, the integral electrically conductive elastic coating is-on the portion that is an electrically, elongatable conductive path; a water-based protective elastic coating, wherein a portion of the electrically, elongatable conductive path is covered by the water-based protective elastic coating and maintains full integration with the electrically insulated elastically expandable member to the elastic limit of the electrically insulated elastically expandable member while being adapted to recover its initial shape when relaxed; where the elasticity of the integral electrically conductive elastic coating is functionally equivalent to the elasticity of the electrically insulated elastically expandable member; wherein the electrically, elongatable conductive path maintains full integration with the electrically insulated elastically expandable member and remains continuously conductive while elongated with a resistivity below 2000 Ohms and is capable of recovering its initial shape; wherein the solvent-based polymer used in the integral electrically conductive elastic coating is styrene and the integral electrically conductive elastic coating further comprises a dispersant agent; and the water-based protective elastic coating is urethane.

18. The electrical conductor of claim 17, wherein the electrically conductive filler is silver flakes.

19. The electrical conductor of claim 17, wherein the solvent in the solvent-based styrene polymer is a blend of toluene, methyl-ethyl-ketone and heptanes.

20. The electrical conductor of claim 17, wherein the protective elastic coating insulates the outside of the electrically, elongatable conductive path.

21. The electrical conductor of claim 17, wherein integral electrically conductive elastic coating is applied by (a) sprayed through an atomizer or (b) dispensed through a syringe.

* * * * *